United States Patent
Kim et al.

(10) Patent No.: US 8,283,057 B2
(45) Date of Patent: Oct. 9, 2012

(54) HETEROARYLAMINE COMPOUND AND ORGANIC LIGHT-EMITTING DEVICE INCLUDING THE SAME

(75) Inventors: Young-Kook Kim, Yongin (KR); Seok-Hwan Hwang, Yongin (KR); Yoon-Hyun Kwak, Yongin (KR); Hye-Jin Jung, Yongin (KR); Jong-Hyuk Lee, Yongin (KR); Jin-O Lim, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 133 days.

(21) Appl. No.: 12/830,646

(22) Filed: Jul. 6, 2010

(65) Prior Publication Data
US 2011/0049484 A1 Mar. 3, 2011

(30) Foreign Application Priority Data

Aug. 28, 2009 (KR) .................. 10-2009-0080701

(51) Int. Cl.
*H01L 51/54* (2006.01)
(52) U.S. Cl. ........ 428/690; 428/917; 313/504; 313/505; 313/506; 564/426; 564/434
(58) Field of Classification Search .................. 428/690, 428/917; 313/504, 505, 506; 548/440; 564/426, 564/434
See application file for complete search history.

(56) References Cited

U.S. PATENT DOCUMENTS

| 6,465,115 | B2 | 10/2002 | Shi et al. |
| 6,596,415 | B2 | 7/2003 | Shi et al. |
| 7,901,793 | B2 | 3/2011 | Kim et al. |
| 2007/0072002 | A1 | 3/2007 | Kim et al. |
| 2010/0033088 | A1 | 2/2010 | Hwang et al. |

FOREIGN PATENT DOCUMENTS

| JP | 10310574 | 11/1998 |
| JP | 2002148835 A | 5/2002 |
| JP | 2005093159 A | 4/2005 |
| JP | 2008133225 A | 6/2008 |
| KR | 10-2007-0034430 | 3/2007 |
| KR | 1020080112325 A | 12/2008 |

OTHER PUBLICATIONS

European Search Report dated Jan. 10, 2011, for corresponding European Patent application 10251513.7.
Korean Office action dated May 24, 2011, re Patent No. 10-2009-0080701; 6 pages.

*Primary Examiner* — Jennifer Chriss
*Assistant Examiner* — Gregory Clark
(74) *Attorney, Agent, or Firm* — Christie, Parker & Hale, LLP

(57) ABSTRACT

Embodiments of the present invention are directed to heteroarylamine compounds and organic light-emitting devices including the heteroarylamine compounds. The organic light-emitting devices using the heteroarylamine compounds have high-efficiency, low driving voltages, high luminance and long lifespans.

16 Claims, 2 Drawing Sheets

HETEROARYLAMINE COMPOUND AND ORGANIC LIGHT-EMITTING DEVICE INCLUDING THE SAME

CROSS-REFERENCE TO RELATED PATENT APPLICATION

This application claims priority to and the benefit of Korean Patent Application No. 10-2009-0080701, filed on Aug. 28, 2009, in the Korean Intellectual Property Office, the entire content of which is incorporated herein by reference.

BACKGROUND OF THE INVENTION

1. Field of the Invention

The present invention relates to heteroarylamine compounds and to organic light-emitting devices including the heteroarylamine compounds.

2. Description of the Related Art

Light-emitting devices are self-emission type display devices having wide viewing angles, high contrast ratios, and short response times. Due to these characteristics, light-emitting devices are drawing more attention. Such light-emitting devices can be roughly classified into inorganic light-emitting devices (which include emission layers containing inorganic compounds), and organic light-emitting devices (which include emission layers containing organic compounds). Specifically, organic light-emitting devices have higher luminance, lower driving voltages, and shorter response times than inorganic light-emitting devices, and can produce multi-colored displays. Thus, much research into organic light-emitting devices has been conducted.

Typically, an organic light-emitting device has a stacked structure including an anode, a cathode and an organic emission layer between the anode and cathode. However, a hole injection layer and/or a hole transport layer may be further stacked between the anode and the organic emission layer, and/or an electron transport layer may be further stacked between the organic emission layer and the cathode. In other words, an organic light-emitting device may have an anode/hole transport layer/organic emission layer/cathode stack structure or an anode/hole transport layer/organic emission layer/electron transport layer/cathode stack structure.

Known materials for the hole injection layer and/or hole transport layer of organic light-emitting devices do not have satisfactory lifespan, efficiency, and power consumption characteristics, thus leaving much room for improvement.

SUMMARY OF THE INVENTION

According to embodiments of the present invention, an organic layer material has improved electrical stability and charge transporting capability, high glass transition temperature, and improved ability to prevent crystallization. The organic layer material is suitable for fluorescent or phosphorescent organic light-emitting devices (OLEDs), including full-color OLEDs (which can generate all colors, including red, green, blue, and white).

In some embodiments of the present invention, an OLED includes an organic layer formed of the above-described material. The OLED has high efficiency, low driving voltage, and improved luminance. In other embodiments, a flat panel display device includes the OLED.

According to embodiments of the present invention, a heteroarylamine compound is represented by Formula 1 below:

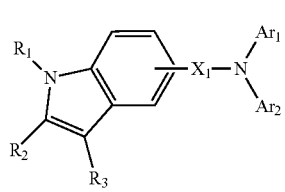

Formula 1

In Formula 1, each of $Ar_1$ and $Ar_2$ is independently selected from substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. $X_1$ is selected from substituted and unsubstituted $C_6$-$C_{30}$ arylene groups, substituted and unsubstituted $C_4$-$C_{30}$ heteroarylene groups, and substituted and unsubstituted $C_6$-$C_{30}$ condensed polycyclic groups. Each of $R_1$, $R_2$ and $R_3$ is independently selected from hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_6$-$C_{60}$ condensed polycyclic group, halogen atoms, cyano groups, hydroxyl groups, and carboxyl groups.

According to other embodiments of the present invention, an organic light-emitting device includes a first electrode, a second electrode, and an organic layer between the first electrode and the second electrode. The organic layer includes at least one organic layer containing the heteroarylamine compound described above.

According to still other embodiments of the present invention, a flat panel display device comprises the organic light-emitting device described above, in which the first electrode of the organic light-emitting device is electrically connected to a source electrode or a drain electrode of a thin film transistor.

According to yet other embodiments of the present invention, an organic light-emitting device includes a first electrode, a second electrode, and an organic layer between the first electrode and the second electrode. The organic layer includes at least one layer including the heteroarylamine compound described above, and the at least one layer is formed using a wet process.

BRIEF DESCRIPTION OF THE DRAWINGS

The above and other features and advantages of the present invention will become more apparent by reference to the following detailed description when considered in conjunction with the attached drawing in which.

DETAILED DESCRIPTION OF THE INVENTION

Figure 1:
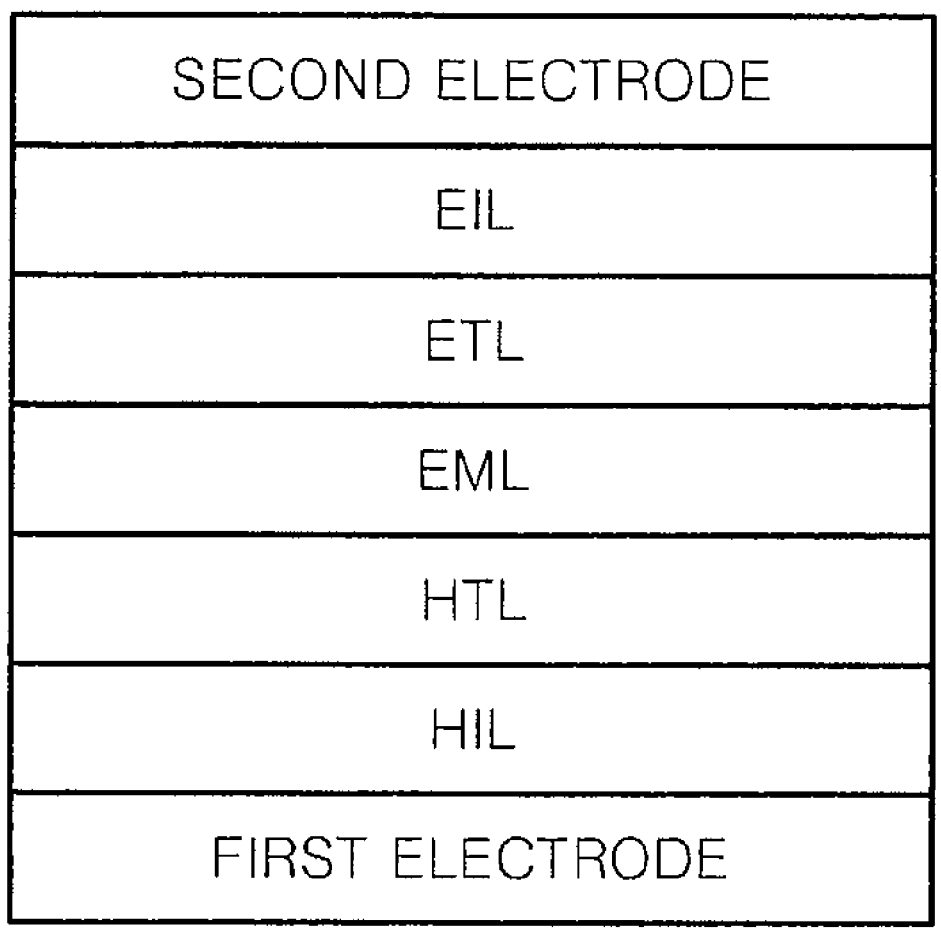
FIG. 1 is a schematic view of an organic light-emitting device according to an embodiment of the present invention.

According to embodiments of the present invention, a heteroarylamine compound is represented by Formula 1 below.

In some embodiments, the heteroarylamine compound may be used to form an organic layer of an organic light-emitting device (OLED).

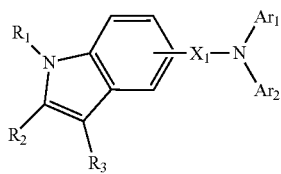

Formula 1

In Formula 1, each of $Ar_1$ and $Ar_2$ is independently selected from substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. $X_1$ may be selected from substituted and unsubstituted $C_6$-$C_{30}$ arylene groups (for example, $C_6$-$C_{18}$ arylene groups), substituted and unsubstituted $C_4$-$C_{30}$ heteroarylene groups (for example, $C_5$-$C_{20}$ heteroarylene groups), and substituted and unsubstituted $C_6$-$C_{20}$ condensed polycyclic groups. Each of $R_1$, $R_2$ and $R_3$ may be independently selected from hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_6$-$C_{60}$ condensed polycyclic groups, halogen atoms, cyano groups, hydroxyl groups, and carboxyl groups.

Nonlimiting examples of the arylene group or heteroarylene group (represented by $X_1$) include phenylene groups, 1-naphthylene groups, 2-naphthylene groups, 1-anthrylene groups, 2-anthrylene groups, 9-anthrylene groups, 1-phenanthrylene groups, 2-phenanthrylene groups, 3-phenanthrylene groups, 4-phenanthrylene groups, 9-phenanthrylene groups, 1-naphthacenylene groups, 2-naphthacenylene groups, 9-naphthacenylene groups, 1-pyrenylene groups, 2-pyrenylene groups, 4-pyrenylene groups, 2-biphenylene groups, 3-biphenylene groups, 4-biphenylene groups, p-terphenyl-4-ylene groups, p-terphenyl-3-ylene groups, p-terphenyl-2-ylene groups, m-terphenyl-4-ylene groups, m-terphenyl-3-ylene groups, m-terphenyl-2-ylene groups, o-tolylene groups, m-tolylene groups, p-tolylene groups, p-t-butylphenylene groups, p-(2-phenylpropyl)phenylene groups, 3-methyl-2-naphthylene groups, 4-methyl-1-naphthylene groups, 4-methyl-1-anthrylene groups, 4'-methylbiphenylyl groups, 4''-t-butyl-p-terphenyl-4-ylene groups, fluoranthenylene groups, fluorenylene groups, 1-pyrrolene groups, 2-pyrrolene groups, 3-pyrrolene groups, pyrazinylene groups, 2-pyridinylene groups, 3-pyridinylene groups, 4-pyridinylene groups, 1-indolylene groups, 2-indolylene groups, 3-indolylene groups, 4-indolylene groups, 5-indolylene groups, 6-indolylene groups, 7-indolylene groups, 1-isoindolylene groups, 2-isoindolylene groups, 3-isoindolylene groups, 4-isoindolylene groups, 5-isoindolylene groups, 6-isoindolylene groups, 7-isoindolylene groups, 2-furylene groups, 3-furylene groups, 2-benzofuranylene groups, 3-benzofuranylene groups, 4-benzofuranylene groups, 5-benzofuranylene groups, 6-benzofuranylene groups, 7-benzofuranylene groups, 1-isobenzofuranylene groups, 3-isobenzofuranylene groups, 4-isobenzofuranylene groups, 5-isobenzofuranylene groups, 6-isobenzofuranylene groups, 7-isobenzofuranylene groups, quinolylene groups, 3-quinolylene groups, 4-quinolylene groups, 5-quinolylene groups, 6-quinolylene groups, 7-quinolylene groups, 8-quinolylene groups, 1-isoquinolylene groups, 3-isoquinolylene groups, 4-isoquinolylene groups, 5-isoquinolylene groups, 6-isoquinolylene groups, 7-isoquinolylene groups, 8-isoquinolylene groups, 2-quinoxalinylene groups, 5-quinoxalinylene groups, 6-quinoxalinylene groups, 1-carbazolylene groups, 2-carbazolylene groups, 3-carbazolylene groups, 4-carbazolylene groups, 9-carbazolylene groups, 1-phenanthridinylene groups, 2-phenanthridinylene groups, 3-phenanthridinylene groups, 4-phenanthridinylene groups, 6-phenanthridinylene groups, 7-phenanthridinylene groups, 8-phenanthridinylene groups, 9-phenanthridinylene groups, 10-phenanthridinylene groups, 1-acridinylene groups, 2-acridinylene groups, 3-acridinylene groups, 4-acridinylene groups, 9-acridinylene groups, 1,7-phenanthroline-2-ylene groups, 1,7-phenanthroline-3-ylene groups, 1,7-phenanthroline-4-ylene groups, 1,7-phenanthroline-5-ylene groups, 1,7-phenanthroline-6-ylene groups, 1,7-phenanthroline-8-ylene groups, 1,7-phenanthroline-9-ylene groups, 1,7-phenanthroline-10-ylene groups, 1,8-phenanthroline-2-ylene groups, 1,8-phenanthroline-3-ylene groups, 1,8-phenanthroline-4-ylene groups, 1,8-phenanthroline-5-ylene groups, 1,8-phenanthroline-6-ylene groups, 1,8-phenanthroline-7-ylene groups, 1,8-phenanthroline-9-ylene groups, 1,8-phenanthroline-10-ylene groups, 1,9-phenanthroline-2-ylene groups, 1,9-phenanthroline-3-ylene groups, 1,9-phenanthroline-4-ylene groups, 1,9-phenanthroline-5-ylene groups, 1,9-phenanthroline-6-ylene groups, 1,9-phenanthroline-7-ylene groups, 1,9-phenanthroline-8-ylene groups, 1,9-phenanthroline-10-ylene groups, 1,10-phenanthroline-2-ylene groups, 1,10-phenanthroline-3-ylene groups, 1,10-phenanthroline-4-ylene groups, 1,10-phenanthroline-5-ylene groups, 2,9-phenanthroline-1-ylene groups, 2,9-phenanthroline-3-ylene groups, 2,9-phenanthroline-4-ylene groups, 2,9-phenanthroline-5-ylene groups, 2,9-phenanthroline-6-ylene groups, 2,9-phenanthroline-7-ylene groups, 2,9-phenanthroline-8-ylene groups, 2,9-phenanthroline-10-ylene groups, 2,8-phenanthroline-1-ylene groups, 2,8-phenanthroline-3-ylene groups, 2,8-phenanthroline-4-ylene groups, 2,8-phenanthroline-5-ylene groups, 2,8-phenanthroline-6-ylene groups, 2,8-phenanthroline-7-ylene groups, 2,8-phenanthroline-9-ylene groups, 2,8-phenanthroline-10-ylene groups, 2,7-phenanthroline-1-ylene groups, 2,7-phenanthroline-3-ylene groups, 2,7-phenanthroline-4-ylene groups, 2,7-phenanthroline-5-ylene groups, 2,7-phenanthroline-6-ylene groups, 2,7-phenanthroline-8-ylene groups, 2,7-phenanthroline-9-ylene groups, 2,7-phenanthroline-10-ylene groups, 1-phenazinylene groups, 2-phenazinylene groups, 1-phenothiazinylene groups, 2-phenothiazinylene groups, 3-phenothiazinylene groups, 4-phenothiazinylene groups, 10-phenothiazinylene groups, 1-phenoxazinylene groups, 2-phenoxazinylene groups, 3-phenoxazinylene groups, 4-phenoxazinylene groups, 10-phenoxazinylene groups, 2-oxazolylene groups, 4-oxazolylene groups, 5-oxazolylene groups, 2-oxadiazolylene groups, 5-oxadiazolylene groups, 3-furazanylene groups, 2-thienylene groups, 3-thienylene groups, 2-methylpyrrol-1-ylene groups, 2-methylpyrrol-3-ylene groups, 2-methylpyrrol-4-ylene groups, 2-methylpyrrol-5-ylene groups, 3-methylpyrrol-1-ylene groups, 3-methylpyrrol-2-ylene groups, 3-methylpyrrol-4-ylene groups, 3-methylpyrrol-5-ylene groups, 2-t-butylpyrrol-4-ylene groups, 3-(2-phenylpropyl)pyrrol-1-ylene groups, 2-methyl-1-indolylene groups, 4-methyl-1-indolylene groups, 2-methyl-3-indolylene groups, 4-methyl-3-indolylene groups, 2-t-butyl-1-indolylene groups, 4-t-butyl-1-indolylene groups, 2-t-butyl-3-indolylene groups, and 4-t-butyl-3-indolylene groups.

Nonlimiting examples of the arylene group represented by $X_1$ include phenylene groups, biphenylene groups, terphenylene groups, quaterphenylene groups, naphthylene groups, anthracenylene groups, phenanthrylene groups, chrysenylene groups, pyrenylene groups, perylenylene groups, and a fluorenylene groups. For example, the arylene group may be selected from phenylene groups, biphenylene groups, naphthylene groups, anthracenyl groups, phenanthrylene groups, and fluorenylene groups.

Nonlimiting examples of the heteroarylene group represented by $X_1$ include thiophenylene groups, 1-phenylthiophenylene groups, 1,4-diphenylthiophenylene groups, benzothiophenylene groups, 1-phenylbenzothiophenylene groups, 1,8-diphenylbenzothiophenylene groups, furylene groups, 1-phenyldibenzothiophenylene groups, 1,8-diphenylthiophenylene groups, dibenzofuranylene groups, 1-phenyldibenzofuranylene groups, 1,8-diphenyldibenzofuranylene groups, and benzothiazolyl groups. For example, the heteroarylene group may be selected from 1-phenylthiophenyl groups, 1-phenylbenzothiophenyl groups, 1-phenyldibenzofuranyl groups, and benzothiazolyl groups.

In Formula 1, $X_1$ functions as a linker. When the heteroarylamine compound is used as a material for injecting and transporting holes, the linker stabilizes radical cations generated during voltage application, and thus increases the lifetime of the device. However, when a single benzene ring (such as in m-MTDATA [4,4',4"-tris (3-methylphenylphenylamino)triphenylamine], TDATA, or 2-TNATA) includes two nitrogen atoms directly substituted in para-position on the benzene ring without a linker (such as $X_1$), the device may not have a satisfactory lifetime. Nonlimiting examples of the linker may include bivalent organic groups represented by the following formulae.

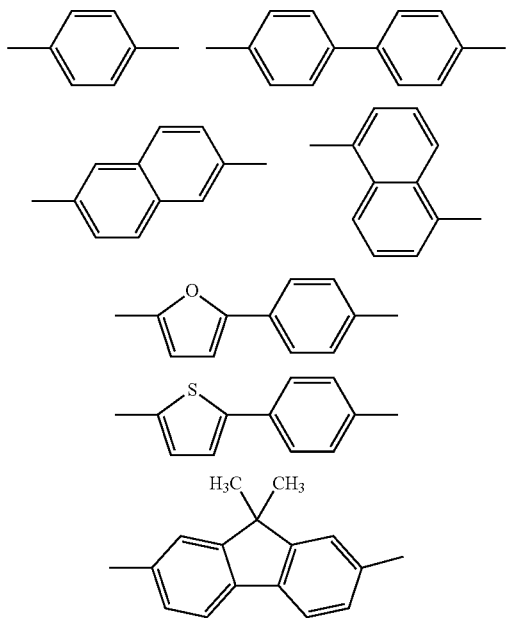

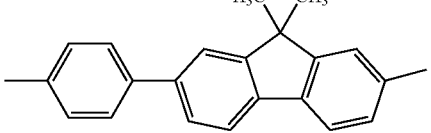

In Formula 1 above, each of $Ar_1$ and $Ar_2$ may be independently selected from unsubstituted and substituted C6-C60 aryl groups (for example, aryl groups having from 6 to 18 carbon atoms forming an aromatic ring), and unsubstituted and substituted C4-C60 heteroaryl groups (for example, aryl groups having 5 to 20 carbon atoms forming an aromatic ring).

Nonlimiting examples of the aryl group represented by $Ar_1$ or $Ar_2$ include phenyl groups, 1-naphthyl groups, 2-naphthyl groups, 1-anthracenyl groups, 2-anthracenyl groups, 9-anthracenyl groups, 1-phenanthryl groups, 2-phenanthryl groups, 3-phenanthryl groups, 4-phenanthryl groups, 9-phenanthryl groups, 1-naphthacenyl groups, 2-naphthacenyl groups, 9-naphthacenyl groups, 1-pyrenyl groups, 2-pyrenyl groups, 4-pyrenyl groups, 2-biphenylyl groups, 3-biphenylyl groups, 4-biphenylyl groups, p-terphenyl-4-yl groups, p-terphenyl-3-yl groups, p-terphenyl-2-yl groups, m-terphenyl-4-yl groups, m-terphenyl-3-yl groups, and m-terphenyl-2-yl groups.

Nonlimiting examples of the heteroaryl group represented by $Ar_1$ or $Ar_2$ include thiophenyl groups, 1-phenylthiophenyl groups, 1,4-diphenylthiophenyl groups, benzothiophenyl groups, 1-phenylbenzothiophenyl groups, 1,8-diphenylbenzothiophenyl groups, furyl groups, 1-phenyldibenzothiophenyl groups, 1,8-diphenylthiophenyl groups, dibenzofuranyl groups, 1-phenyldibenzofuranyl groups, 1,8-diphenyldibenzofuranyl groups, and benzothiazolyl groups.

In Formula 1 above, $R_1$ may be selected from substituted and unsubstituted $C_6$-$C_{60}$ aryl group (for example, aryl groups having 6 to 18 carbon atoms forming an aromatic ring).

Nonlimiting examples of the aryl group represented by $R_1$ include phenyl groups, 1-naphthyl groups, 2-naphthyl groups, 1-anthracenyl groups, 2-anthracenyl groups, 9-anthracenyl groups, 1-phenanthryl groups, 2-phenanthryl groups, 3-phenanthryl groups, 4-phenanthryl groups, 9-phenanthryl groups, 1-naphthacenyl groups, 2-naphthacenyl groups, 9-naphthacenyl groups, 1-pyrenyl groups, 2-pyrenyl groups, 4-pyrenyl groups, 2-biphenylyl groups, 3-biphenylyl groups, 4-biphenylyl groups, p-terphenyl-4-yl groups, p-terphenyl-3-yl groups, p-terphenyl-2-yl groups, m-terphenyl-4-yl groups, m-terphenyl-3-yl groups, m-terphenyl-2-yl groups, o-tolyl groups, m-tolyl groups, p-tolyl groups, p-t-butylphenyl groups, p-(2-phenylpropyl)phenyl groups, 3-methyl-2-naphthyl groups, 4-methyl-1-naphthyl groups, 4-methyl-1-anthryl groups, 4'-methylbiphenylyl groups, and 4"-t-butyl-p-terphenyl-4-yl groups. For example, the aryl group may be selected from phenyl groups, 1-naphthyl groups, 2-naphthyl groups, 4-biphenylyl groups, and p-terphenyl-4-yl groups. In some embodiments, the aryl group may be selected from phenyl groups, biphenylyl groups, terphenylyl groups, α-naphthyl groups, β-naphthyl groups, and phenanthryl groups.

In Formula 1 above, each of $R_2$ and $R_3$ may be independently selected from hydrogen atoms, heavy hydrogen atoms, substituted and unsubstituted C6-C60 aryl groups (for example, C6-C30 aryl groups), substituted and unsubstituted C1-C50 alkyl groups (for example, C1-C20 alkyl groups), substituted and unsubstituted C1-C50 alkoxy groups (for example, C1-C20 alkoxy groups), substituted and unsubstituted C1-C50 alkoxycarbonyl groups (for example, C1-C20 alkoxycarbonyl groups), substituted and unsubstituted C5-C50 aryloxy groups (for example, C6-C20 aryloxy groups), substituted and unsubstituted C5-C50 arylthio groups (for example, C6-C20 arylthio groups), amino groups substituted with at least one substituted or unsubstituted C5-C50 aryl group (for example, a C6-C20 aryl group), halogen atoms, cyano groups, nitro groups, hydroxyl groups, and carboxyl groups.

In Formula 1 above, $R_2$ or $R_3$ may be a substituted or unsubstituted C6-C60 aryl group linked to the 2- or 3-position of an indole backbone, wherein the aryl group forms an aromatic ring.

Nonlimiting examples of the aryl group represented by $R_2$ or $R_3$ include phenyl groups, 1-naphthyl groups, 2-naphthyl groups, 1-anthracenyl groups, 2-anthracenyl groups, 9-anthracenyl groups, 1-phenanthryl groups, 2-phenanthryl groups, 3-phenanthryl groups, 4-phenanthryl groups, 9-phenanthryl groups, 1-naphthacenyl groups, 2-naphthacenyl groups, 9-naphthacenyl groups, 1-pyrenyl groups, 2-pyrenyl groups, 4-pyrenyl groups, 2-biphenylyl groups, 3-biphenylyl groups, 4-biphenylyl groups, p-terphenyl-4-yl groups, p-terphenyl-3-yl groups, p-terphenyl-2-yl groups, m-terphenyl-4-yl groups, m-terphenyl-3-yl groups, m-terphenyl-2-yl groups, o-tolyl groups, m-tolyl groups, p-tolyl groups, p-t-butylphenyl groups, p-(2-phenylpropyl)phenyl groups, 3-methyl-2-naphthyl groups, 4-methyl-1-naphthyl groups, 4-methyl-1-anthryl groups, 4'-methylbiphenylyl groups, 4"-t-butyl-p-terphenyl 4-yl groups, and fluorenyl groups. For example, the aryl group may be selected from phenyl groups, 1-naphthyl groups, 2-naphthyl groups, 4-biphenylyl groups, p-terphenyl-4-yl groups, p-tolyl groups, and fluorenyl groups.

Nonlimiting examples of the aryloxy group represented by $R_2$ or $R_3$ include phenyloxy groups, 1-naphthyloxy groups, 2-naphthyloxy groups, 4-biphenylyloxy groups, p-terphenyl-4-yloxy groups, and p-tolyloxy groups. For example, the aryloxy group may be selected from phenyloxy groups and 2-naphthyloxy groups.

Nonlimiting examples of the arylthio group represented by $R_2$ or $R_3$ include phenylthio groups, 1-naphthylthio groups, 2-naphthylthio groups, 4-biphenylylthio groups, p-terphenyl-4-ylthio groups, and p-tolylthio groups. For example, the arylthio group may be selected from phenylthio groups and 2-naphthylthio groups.

Nonlimiting examples of the alkoxycarbonyl group represented by $R_2$ or $R_3$ include methoxycarbonyl groups, ethoxycarbonyl groups, n-propoxycarbonyl groups, iso-propoxycarbonyl groups, n-butoxycarbonyl groups, and tert-butoxycarbonyl groups. For example, the alkoxycarbonyl group may be selected from methoxycarbonyl groups and ethoxycarbonyl groups.

Nonlimiting examples of the aryl group as a substituent of the amino group, and the aryl group represented by $R_2$ or $R_3$, include those groups listed above in connection with the aryl group represented by $R_1$.

In Formula 1 above, nonlimiting examples of the halogen atom include fluorine atoms, chlorine atoms, bromine atoms, and iodine atoms.

Each of the groups described above may be further substituted, and in some embodiments, may include at least two substituents which may be the same or different. The at least two substituents may be interconnected to form a ring.

Nonlimiting examples of the substituents for $Ar_1$, $Ar_2$, $R_1$, $R_2$ and $R_3$ include alkyl groups, alkenyl groups, alkynyl groups, amino groups, alkoxy groups, aryloxy groups, acyl groups, alkoxycarbonyl groups, aryloxycarbonyl groups, acyloxy groups, acylamino groups, alkoxycarbonylamino groups, aryloxycarbonylamino groups, sulfonylamino groups, sulfamoyl groups, carbamoyl groups, alkylthio groups, arylthio groups, sulfonyl groups, sulfinyl groups, ureide groups, phosphoricamide groups, hydroxyl groups, mercapto groups, halogen atoms, cyano groups, sulfo groups, carboxyl groups, nitro groups, hydroxamic acid groups, sulfino groups, hydrazino groups, imino groups, heterocyclic groups, and silyl groups. These substituents may be further substituted. In some embodiments, for example, $Ar_1$, $Ar_2$, $R_1$, $R_2$ and $R_3$ may each include at least two substituents which may be the same or different. The at least two substituents may be interconnected to form a ring.

Nonlimiting examples of the alkyl group include C1-C20 alkyl groups. In some embodiments for example, the alkyl group is selected from C1-C12 alkyl groups. In other embodiments, the alkyl group is selected from C1-C8 alkyl groups. Nonlimiting examples of suitable alkyl groups include methyl groups, ethyl groups, iso-propyl groups, tert-butyl groups, n-octyl groups, n-decyl groups, n-hexadecyl groups, cyclopropyl groups, cyclopentyl groups, and cyclohexyl groups.

Nonlimiting examples of the alkenyl group include C2-C20 alkenyl groups. In some embodiments, for example, the alkenyl group is selected from C2-C12 alkenyl groups. In other embodiments, the alkenyl group is selected from C2-C8 alkenyl groups. Nonlimiting examples of the alkenyl group include vinyl groups, allyl groups, 2-butenyl groups, and 3-pentenyl groups.

Nonlimiting examples of the alkynyl group include C2-C20 alkynyl group. In some embodiments, for example, the alkynyl group is a C2-C12 alkynyl group. In other embodiment, the alkynyl group is selected from C2-C8 alkynyl groups. A nonlimiting example of the alkynyl group is a 3-pentynyl group.

Nonlimiting examples of the amino group include C0-C20 amino groups. In some embodiments, for example, the amino group is a C0-C12 amino group. In other embodiments, the amino group is selected from C0-C6 amino groups. Nonlimiting examples of the amino group include amino groups, methylamino groups, dimethylamino groups, diethylamino groups, diphenylamino groups, and dibenzylamino groups.

Nonlimiting examples of the alkoxy group include C1-C20 alkoxy groups. In some embodiments, for example, the alkoxy group is a C1-C12 alkoxy group. In other embodiments, the alkoxy group is selected from C1-C8 alkoxy groups. Nonlimiting examples of the alkoxy group include methoxy groups, ethoxy groups, and butoxy groups.

Nonlimiting examples of the aryloxy group include C6-C20 aryloxy groups. In some embodiments, for example, the aryloxy group is a C6-C16 aryloxy group. In other embodiments, the aryloxy group is selected from C6-C12 aryloxy groups. Nonlimiting examples of the aryloxy group include phenyloxy groups, and 2-naphthyloxy groups.

Nonlimiting examples of the acyl group include C1-C20 acyl groups. In some embodiments, for example, the acyl group is a C1-C16 acyl group. In other embodiments, the acyl group is selected from C1-C12 acyl groups. Nonlimiting examples of the acyl group include acetyl groups, benzoyl groups, formyl groups, and pivaloyl groups.

Nonlimiting examples of the alkoxycarbonyl group include C2-C20 alkoxycarbonyl groups. In some embodiments, for example, the alkoxycarbonyl group is a C2-C16 alkoxycarbonyl group. In other embodiments, the alkoxycarbonyl group is selected from C2-C12 alkoxycarbonyl groups.

Nonlimiting examples of the alkoxycarbonyl group include methoxycarbonyl groups, and ethoxycarbonyl groups.

Nonlimiting examples of the aryloxycarbonyl group include C7-C20 aryloxycarbonyl groups. In some embodiments, for example, the aryloxycarbonyl group is a C7-C16 aryloxycarbonyl group. In other embodiments, the aryloxycarbonyl group is selected from C7-C10 aryloxycarbonyl groups. A nonlimiting example of the aryloxycarbonyl group is a phenyloxycarbonyl group.

Nonlimiting examples of the acyloxy group include C2-C20 acyloxy groups. In some embodiments, for example, the acyloxy group is a C2-C16 acyloxy group. In other embodiments, the acyloxy group is selected from C2-C10 acyloxy groups. Nonlimiting examples of the acyloxy group include acetoxy groups and benzoyloxy groups.

Nonlimiting examples of the acylamino group include C2-C20 acylamino groups. In some embodiments, for example, the acylamino group is a C2-C16 acylamino group. In other embodiments, the acylamino group is selected from C2-C10 acylamino groups. Nonlimiting examples of the acylamino group include acetylamino groups, and benzoylamino groups.

Nonlimiting examples of the alkoxycarbonylamino group include C2-C20 alkoxycarbonylamino groups. In some embodiments, for example, the alkoxycarbonylamino group is a C2-C16 alkoxycarbonylamino group. In other embodiments, the alkoxycarbonylamino group is selected from C2-C12 alkoxycarbonylamino groups. A nonlimiting example of a alkoxycarbonylamino group is a methoxycarbonylamino group.

Nonlimiting examples of the aryloxycarbonylamino group include C7-C20 aryloxycarbonylamino groups. In some embodiments, for example, the aryloxycarbonylamino group is a C7-C16 aryloxycarbonylamino group. In other embodiments, the aryloxycarbonylamino group is selected from C7-C12 aryloxycarbonylamino groups. One nonlimiting example of an aryloxycarbonylamino group is a phenyloxycarbonylamino group.

Nonlimiting examples of the sulfonylamino group include C1-C20 sulfonylamino groups. In some embodiments, for example, the sulfonylamino group is a C1-C16 sulfonylamino group. In other embodiments, the sulfonylamino group is selected from C1-C12 sulfonylamino groups. Nonlimiting examples of the sulfonylamino group include methanesulfonylamino groups, and benzenesulfonylamino groups.

Nonlimiting examples of the sulfamoyl group include C0-C20 sulfamoyl groups. In some embodiments, for example, the sulfamoyl group is a C0-C16 sulfamoyl group. In other embodiments, the sulfamoyl group is selected from C0-C12 sulfamoyl groups. Nonlimiting examples of the sulfamoyl group include sulfamoyl groups, methylsulfamoyl groups, dimethylsulfamoyl groups, and phenylsulfamoyl groups.

Nonlimiting examples of the carbamoyl group include C1-C20 carbamoyl groups. In some embodiment, for example, the carbamoyl group is a C1-C16 carbamoyl group. In other embodiments, the carbamoyl group is selected from C1-C12 carbamoyl groups. Nonlimiting examples of the carbamoyl group include carbamoyl groups, methylcarbamoyl groups, diethylcarbamoyl groups, and phenylcarbamoyl groups.

Nonlimiting examples of the alkylthio group include C1-C20 alkylthio groups. In some embodiments, for example, the alkylthio group is a C1-C16 alkylthio group. In other embodiments, the alkylthio group is selected from C1-C12 alkylthio groups. Nonlimiting examples of the alkylthio group include methylthio groups, and ethylthio groups.

Nonlimiting examples of the arylthio group include C6-C20 arylthio groups. In some embodiments, for example, the arylthio group is a C6-C16 arylthio group. In other embodiments, the arylthio group is selected from C6-C12 arylthio groups. One nonlimiting example of the arylthio group is a phenylthio group.

Nonlimiting examples of the sulfonyl group include C1-C20 sulfonyl groups. In some embodiments, for example, the sulfonyl group is a C1-C16 sulfonyl group. In other embodiments, the sulfonyl group is selected from C1-C12 sulfonyl groups. Nonlimiting examples of the sulfonyl group include mesyl groups, and tosyl groups.

Nonlimiting examples of the sulfinyl group include C1-C20 sulfinyl groups. In some embodiments, for example, the sulfinyl group is a C1-C16 sulfinyl group. In other embodiments, the sulfinyl group is selected from C1-C12 sulfinyl groups. Nonlimiting examples of the sulfinyl group include methanesulfinyl groups, and benzenesulfinyl groups.

Nonlimiting examples of the ureide group include C1-C20 ureide groups. In some embodiments, for example, the ureide group is a C1-C16 ureide group. In other embodiments, the ureide group is selected from C1-C12 ureide groups. Nonlimiting examples of the ureide group include ureide groups, methylureide groups, and phenylureide groups.

Nonlimiting examples of the phosphoricamide group include C1-C20 phosphoricamide group. In some embodiments, for example, the phosphoricamide group is a C1-C16 phosphoricamide group. In other embodiments, the phosphoricamide group is selected from C1-C12 phosphoricamide groups. Nonlimiting examples of the phosphoricamide group include diethylphosphoricamide groups, and phenylphosphoricamide groups.

Nonlimiting examples of the halogen atom include fluorine atoms, chlorine atoms, bromine atoms and iodine atoms.

The heterocyclic group may be a C1-C30 heterocyclic group. In some embodiments, for example, the heterocyclic group is a C1-C15 heterocyclic group. Nonlimiting examples of the heterocyclic group include imidazolyl groups, pyridyl groups, quinolyl groups, furyl groups, thienyl groups, piperidyl groups, morpholino groups, benzoxazolyl groups, benzimidazolyl groups, benzothiazolyl groups, and carbazolyl groups, in which the hetero atom may be nitrogen, oxygen, or sulfur.

Nonlimiting examples of the silyl group include C3-C40 silyl groups. In some embodiments, for example, the silyl group is a C3-C30 silyl group. In other embodiments, the silyl group is selected from C3-C24 silyl groups. Nonlimiting examples of the silyl group include trimethylsilyl groups and triphenylsilyl groups.

In some embodiments of the present invention, the heteroarylamine compound of Formula 1 may include a compound represented by any of Formulae 2 through 6 below.

Formula 2

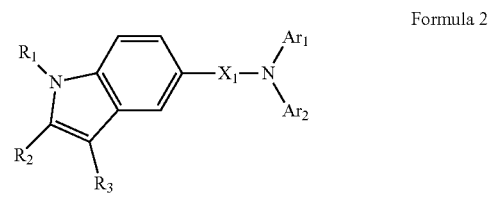

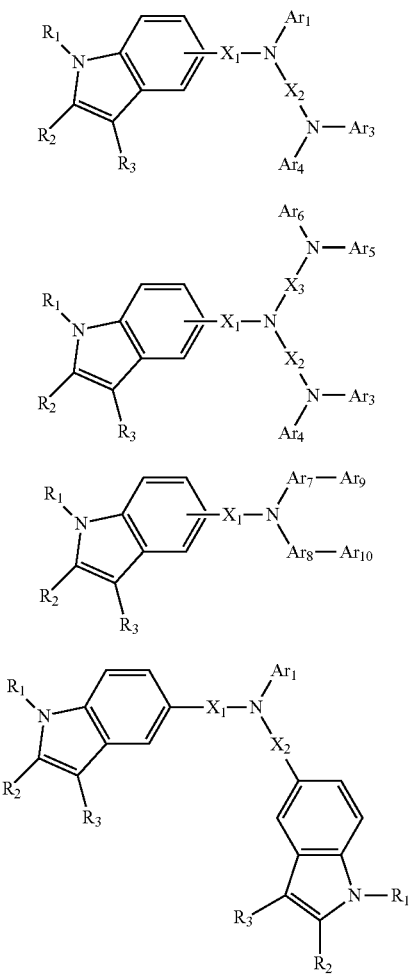

Formula 3

Formula 4

Formula 5

Formula 6

In Formulae 2 through 6, each of $Ar_1$ through $Ar_{10}$ is independently selected from substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. Each of $X_1$ through $X_3$ is independently selected from substituted and unsubstituted $C_6$-$C_{30}$ arylene groups, substituted and unsubstituted $C_4$-$C_{30}$ heteroarylene groups, and substituted and unsubstituted $C_6$-$C_{30}$ condensed polycyclic groups. Each of $R_1$, $R_2$ and $R_3$ is independently selected from hydrogen atoms, heavy hydrogen atoms, substituted and unsubstituted $C_1$-$C_{50}$ alkyl groups, substituted and unsubstituted $C_1$-$C_{50}$ alkoxy groups, substituted and unsubstituted $C_1$-$C_{50}$ alkoxycarbonyl groups, substituted and unsubstituted $C_6$-$C_{60}$ aryl groups, substituted and unsubstituted $C_5$-$C_{50}$ aryloxy groups, substituted and unsubstituted $C_5$-$C_{50}$ arylthio groups, amino groups substituted with at least one substituted or unsubstituted $C_5$-$C_{50}$ aryl group, substituted and unsubstituted $C_3$-$C_{50}$ carbon rings, substituted and unsubstituted $C_4$-$C_{60}$ heteroaryl groups, substituted and unsubstituted $C_5$-$C_{60}$ condensed polycyclic groups, halogen atoms, cyano groups, hydroxyl groups, and carboxyl groups.

In Formulae 2 through 6, each of $Ar_1$ through $Ar_{10}$ may be independently selected from monocyclic to tricyclic aryl groups. Nonlimiting examples of suitable monocyclic to tricyclic aryl groups include phenyl groups, naphthyl groups, biphenyl groups, terphenyl groups, fluorenyl groups, and carbazolyl groups. The monocyclic to tricyclic aryl group may be substituted with from one to three substituents. Nonlimiting examples of these substituents include $C_1$-$C_5$ alkyl groups, $C_1$-$C_5$ alkoxy groups, cyano groups, amino groups, phenoxy groups, phenyl groups, and halogen atoms.

Nonlimiting examples of the arylene group represented by $X_1$ through $X_3$ include phenylene groups, biphenylene groups, terphenylene groups, quaterphenylene groups, naphthylene groups, anthracenylene groups, phenanthrylene groups, chrysenylene groups, pyrenylene groups, perylenylene groups, and fluorenylene groups. In some embodiments, for example, the arylene group may be selected from phenylene groups, biphenylene groups, naphthylene groups, anthracenyl groups, phenanthrylene groups, and fluorenylene groups.

Nonlimiting examples of the heteroarylene group represented by $X_1$ through $X_3$ include thiophenylene groups, 1-phenylthiophenylene groups, 1,4-diphenylthiophenylene groups, benzothiophenylene groups, 1-phenylbenzothiophenylene groups, 1,8-diphenylbenzothiophenylene groups, furylene groups, 1-phenyldibenzothiophenylene groups, 1,8-diphenylthiophenylene groups, dibenzofuranylene groups, 1-phenyldibenzofuranylene groups, 1,8-diphenyldibenzofuranylene groups, and benzothiazolylene groups. In some embodiments, for example, the heteroarylene group may be selected from 1-phenylthiophenyl groups, 1-phenylbenzothiophenyl groups, 1-phenyldibenzofuranyl groups, and benzothiazolyl groups.

In Formulae 1 through 6, or Formulae 2 through 6, each of $R_1$ through $R_3$ is independently an aryl group. In some embodiments, for example, each of $R_1$ through $R_3$ may be independently selected from phenyl groups, 4-fluorophenyl groups, naphthalene groups, and biphenyl groups.

In Formulae 1 through 6 or Formulae 2 through 6, nonlimiting examples of bivalent organic groups represented by $X_1$ through $X_3$ include those represented by the following formulae. Each of $X_1$ through $X_3$ may be independently selected from these bivalent organic groups, but are not limited thereto.

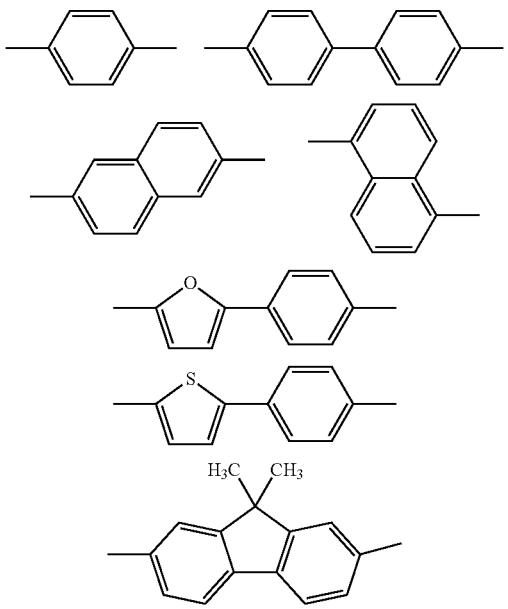

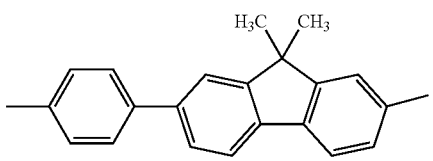
In Formulae 1 through 6 or Formulae 2 through 6, each of $Ar_1$ through $Ar_{10}$ may be independently selected from one of the monovalent organic groups represented by the following formulae.
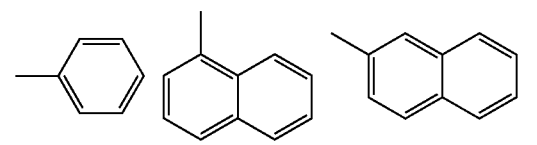
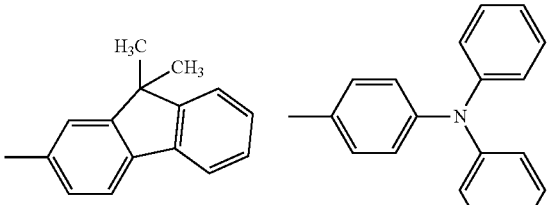
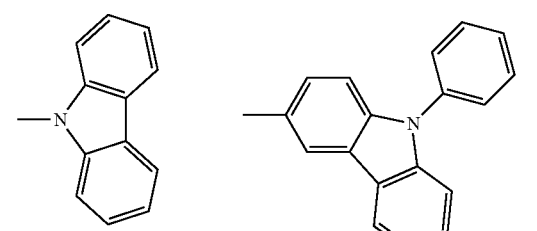
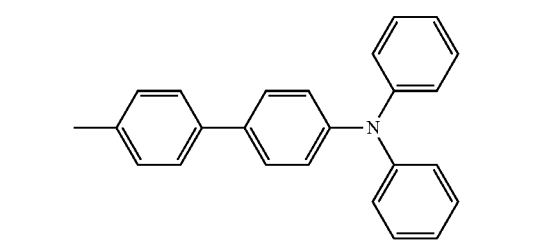
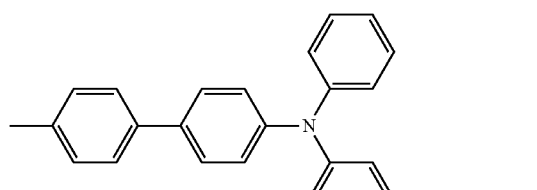
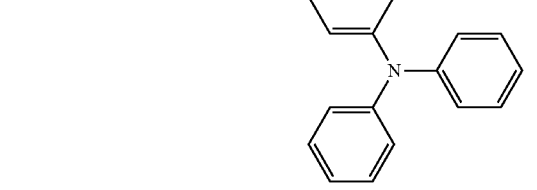
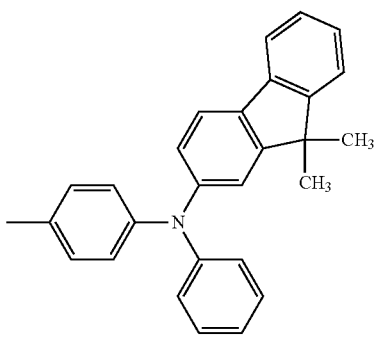
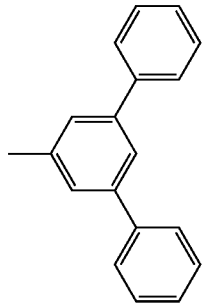
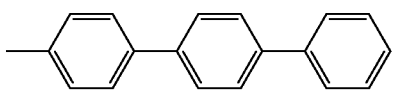
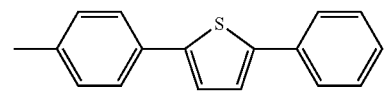
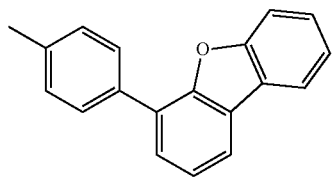
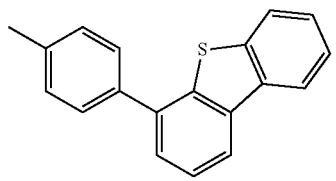
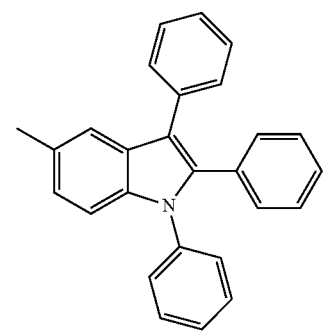

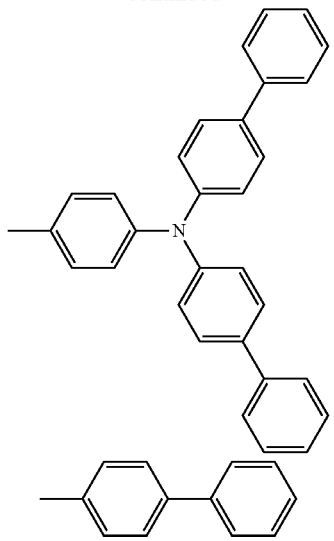

Hereinafter, substituents described with reference to Formulae 1 through 6 will be described.

The unsubstituted $C_1$-$C_{50}$ alkyl group may be linear or branched. Nonlimiting examples of the alkyl group include methyl groups, ethyl groups, propyl groups, isobutyl groups, sec-butyl groups, pentyl groups, iso-amyl groups, hexyl groups, heptyl groups, octyl groups, nonanyl groups, and dodecyl groups. At least one hydrogen atom of the alkyl group may be substituted with a substituent selected from heavy hydrogen atoms, halogen atoms, hydroxyl groups, nitro groups, cyano groups, amino groups, amidino groups, hydrazines, hydrazones, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups.

The unsubstituted $C_3$-$C_{50}$ carbon ring refers to a $C_3$-$C_{50}$ cycloalkyl group where at least one hydrogen atom in the carbon ring may be substituted with the substituents described above in connection with the $C_1$-$C_{50}$ alkyl group.

The unsubstituted $C_4$-$C_{60}$ heterocyclic group refers to a $C_4$-$C_{60}$ cycloalkyl group including one, two or three hetero atoms selected from N, O, P and S, where at least one hydrogen atom in the heterocyclic group may be substituted with the substituents described above in connection with the $C_1$-$C_{50}$ alkyl group.

The unsubstituted $C_1$-$C_{50}$ alkoxy group is a group having a —OA structure where A is an unsubstituted $C_1$-$C_{50}$ alkyl group as described above. Nonlimiting examples of the alkoxy group include methoxy groups, ethoxy groups, propoxy groups, isopropyloxy groups, butoxy groups, and pentoxy groups. At least one hydrogen atom of the alkoxy group may be substituted with the substituents described above in connection with the $C_1$-$C_{50}$ alkyl group.

The unsubstituted $C_6$-$C_{60}$ aryl group refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with the substituents described above in connection with the $C_1$-$C_{50}$ alkyl group.

Nonlimiting examples of the substituted or unsubstituted $C_6$-$C_{60}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$alkyl biphenyl groups, $C_1$-$C_{10}$ alkoxybiphenyl groups, o-, m-, and p-toryl groups, o-, m-, and p-cumenyl groups, mesityl groups, phenoxyphenyl groups, (α,α-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_4$-$C_{60}$heteroaryl group includes one, two or three hetero atoms selected from N, O, P and S. At least two rings may be fused to each other or linked to each other by a single bond. Nonlimiting examples of the unsubstituted $C_4$-$C_{60}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. At least one hydrogen atom in the heteroaryl group may be substituted with the substituents described above in connection with the $C_1$-$C_{50}$ alkyl group.

The unsubstituted $C_6$-$C_{60}$ condensed polycyclic group refers to a substituent including at least two rings where at least one aromatic ring and/or at least one non-aromatic ring are fused to each other. The unsubstituted $C_6$-$C_{60}$ polycyclic condensed group may include some of the substituents described in connection with the aryl group or the heteroaryl group.

The heteroarylamine compound of Formula 1 may be used as an organic layer material having at least one of hole-injecting capability, hole-transporting capability, and light-emitting capability.

The heteroarylamine compound of Formula 1 has a heterocyclic group in the molecule, and therefore has a high glass transition temperature (Tg) or melting point due to the introduction of the heterocyclic group. Thus, the heteroarylamine compound has high heat resistance against Joule's heat generated in an organic layer, between organic layers, or between an organic layer and a metallic electrode when light emission occurs. The heteroarylamine compound also has high durability in a high-temperature environment. An organic light-emitting device manufactured using the heteroarylamine compound has high durability when stored or operated.

Nonlimiting examples of the heteroarylamine compound of Formula 1 include the following Compounds 1-83:
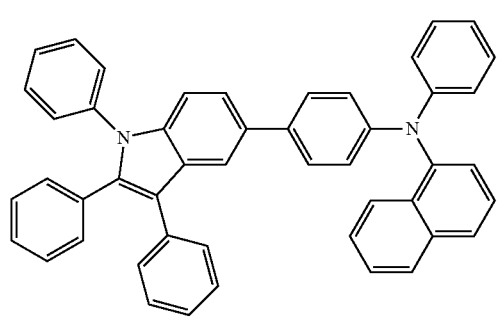
1
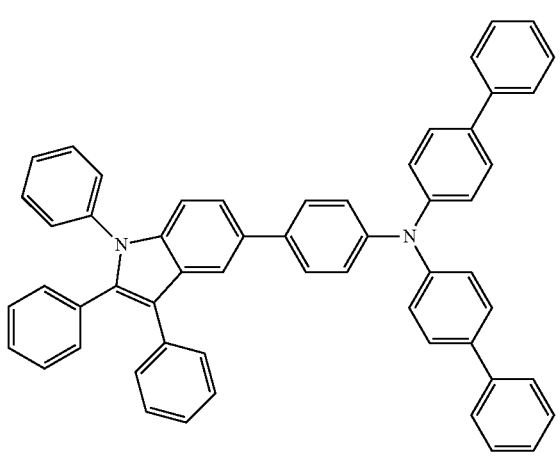
2
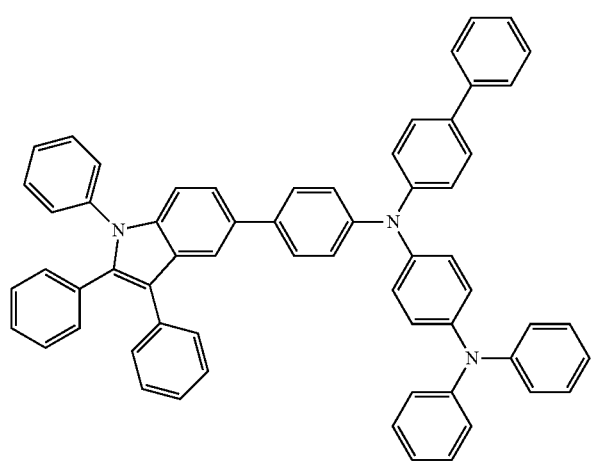
3
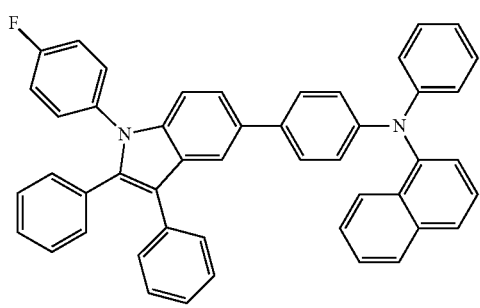
4
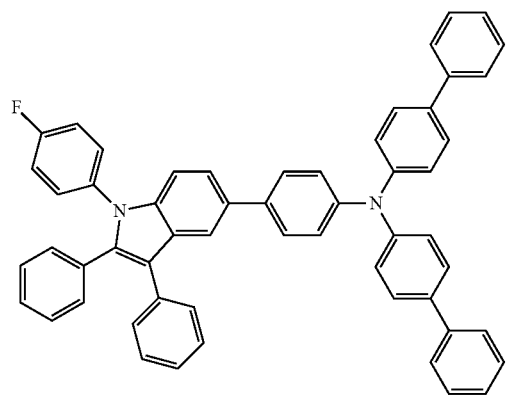
5
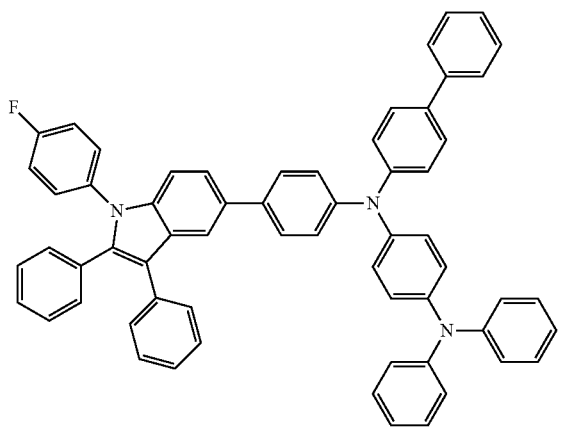
6

7
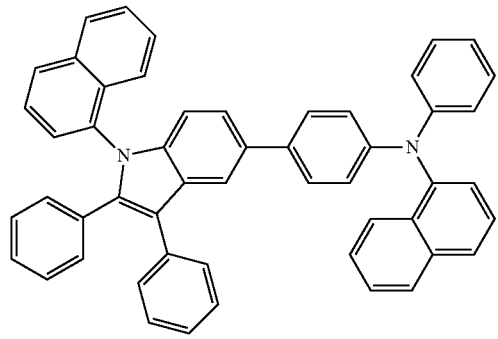
8
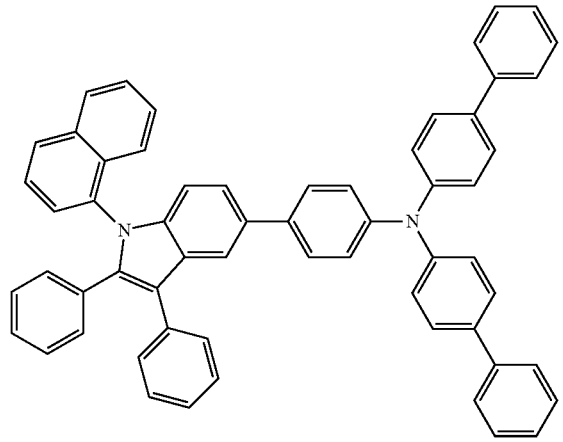
9
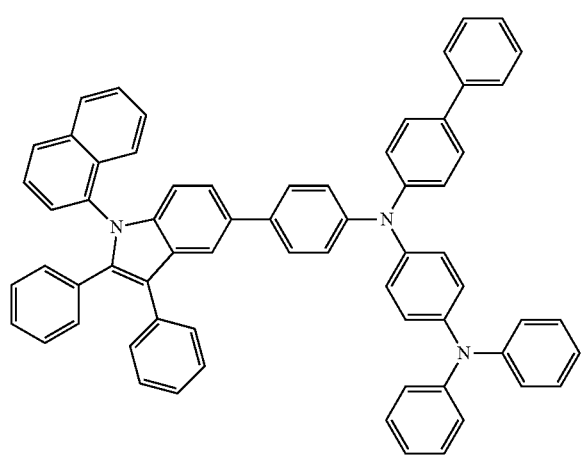
10
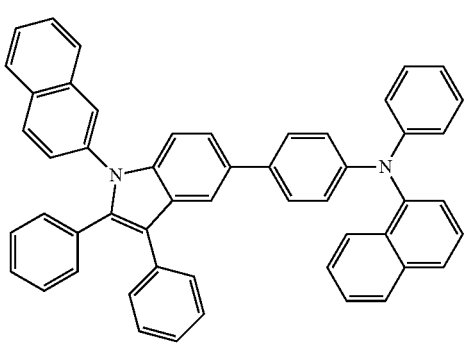
11
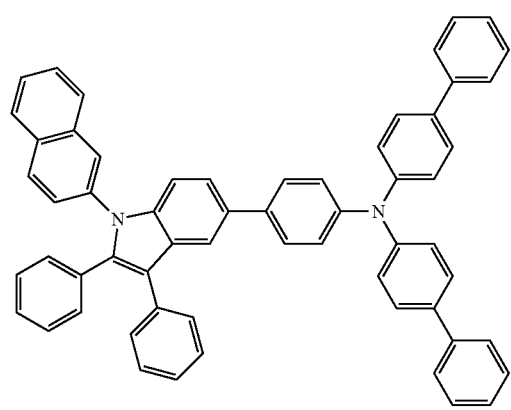
12
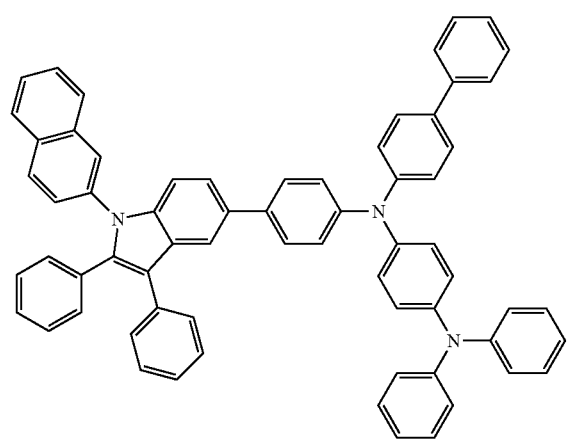

-continued
13
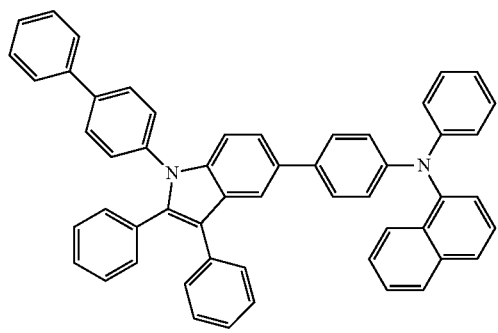
14
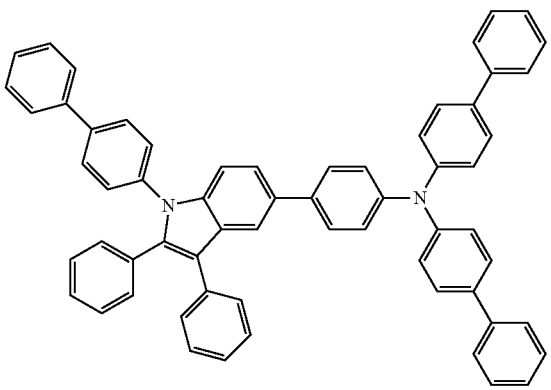
15
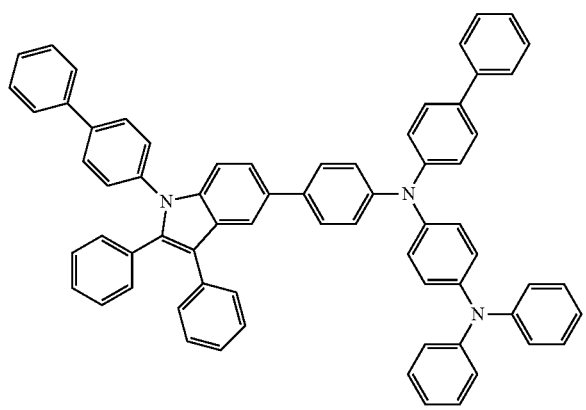
16
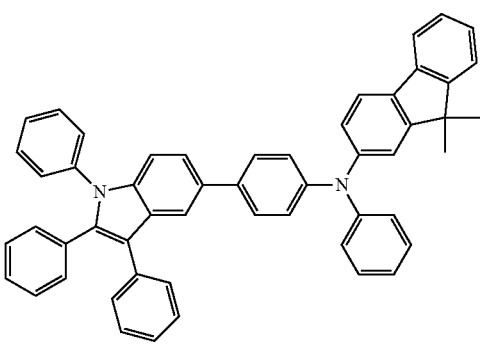
17
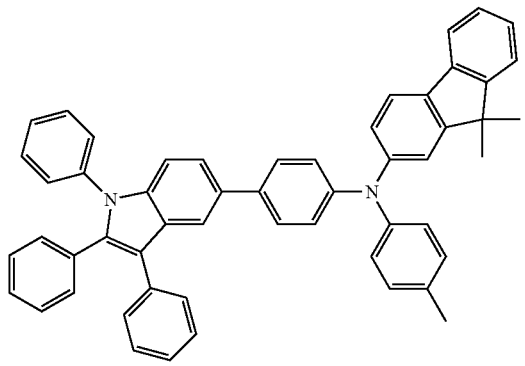
18
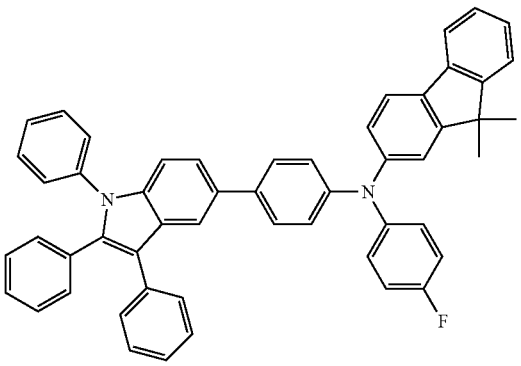
19
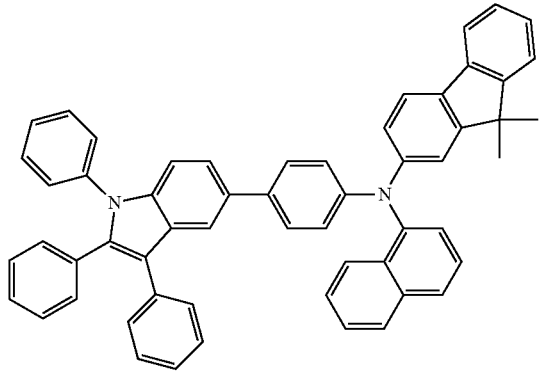
20
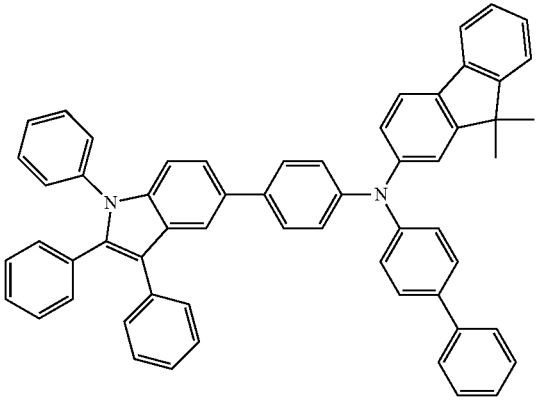

-continued
21
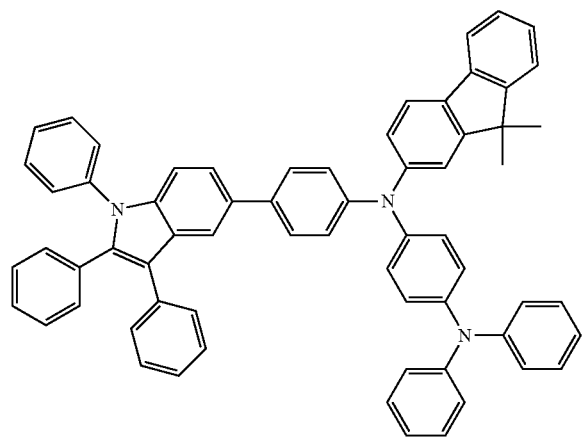
22
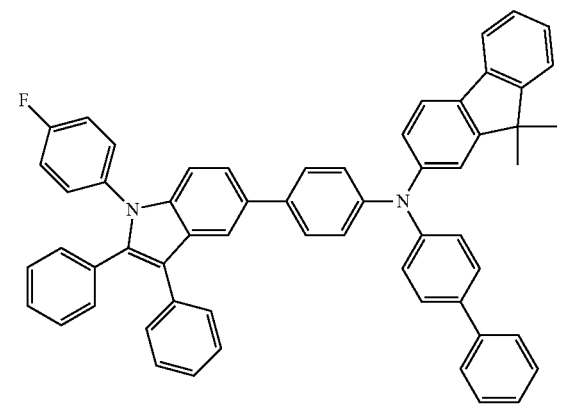
23
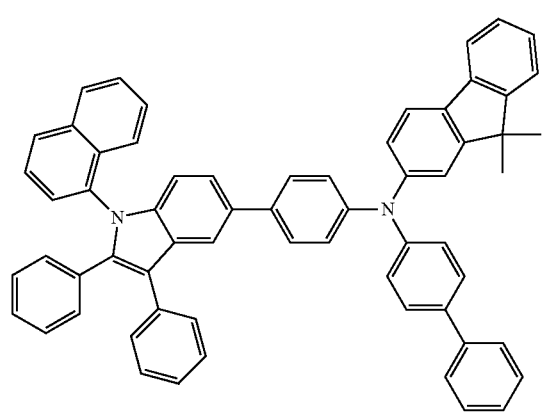
24
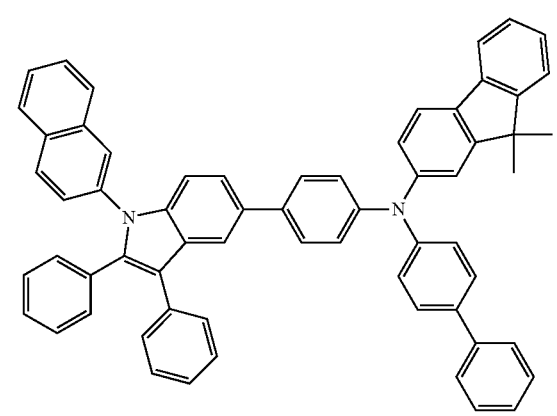
25
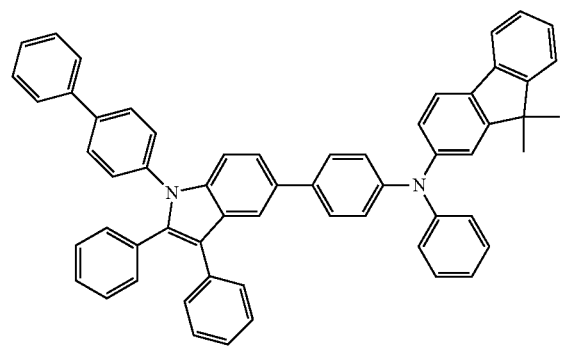
26
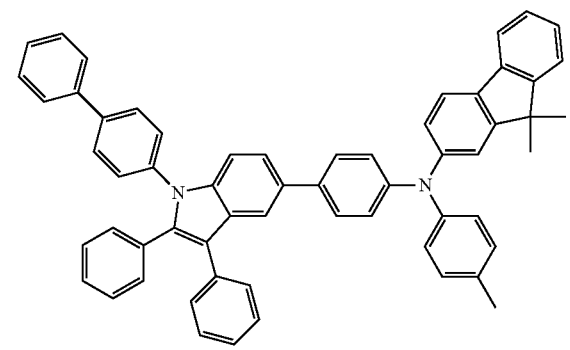
27
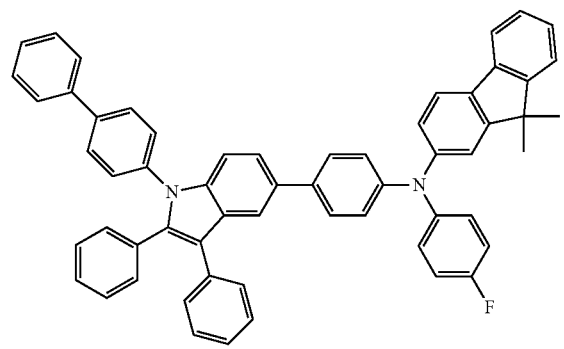
28
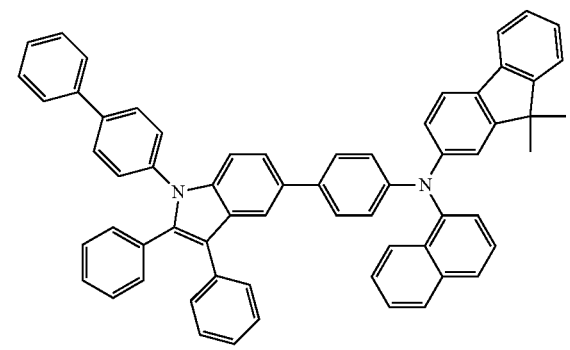

-continued
29
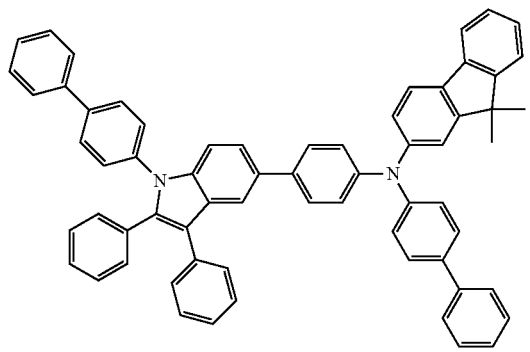
30
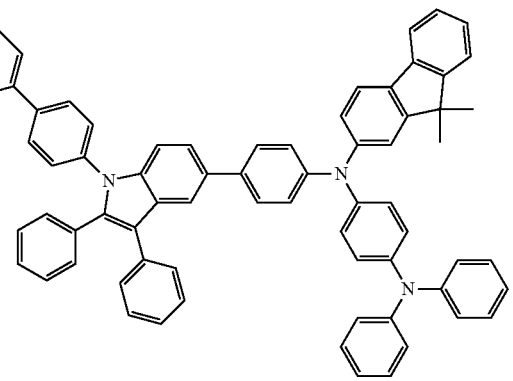
31
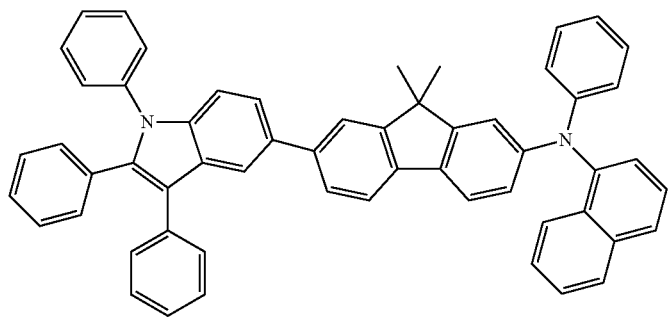
32
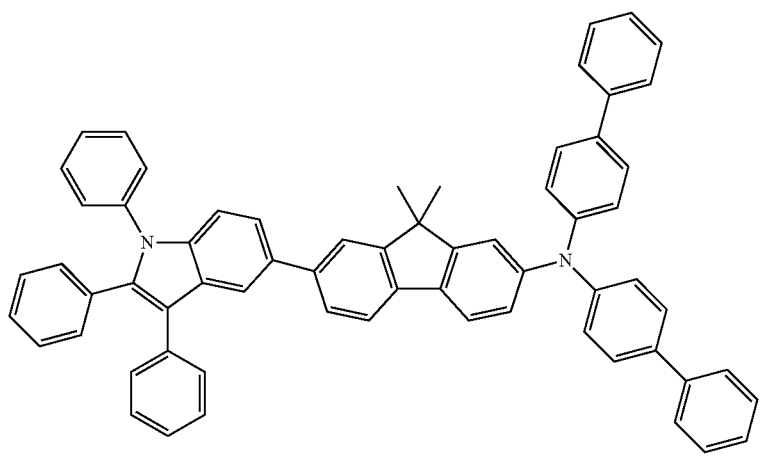

-continued
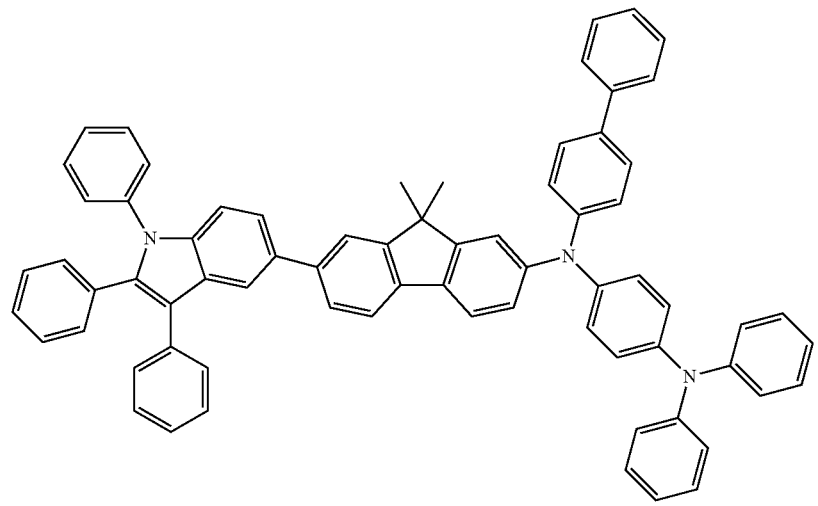
33
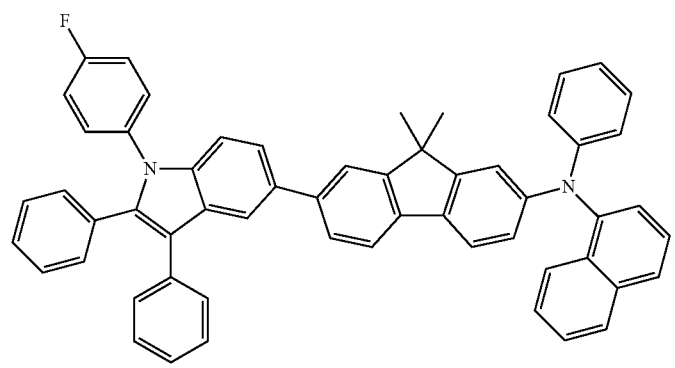
34
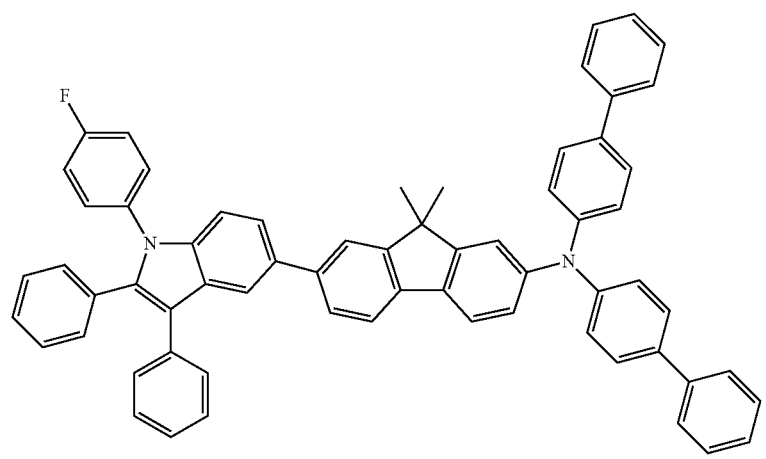
35

-continued
36
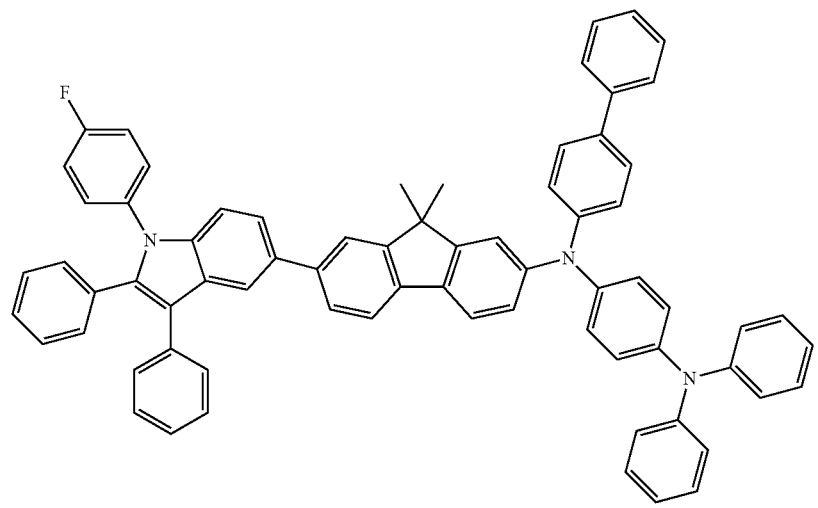
37
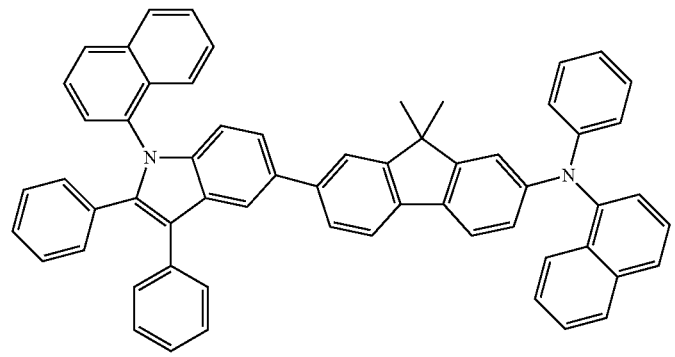
38
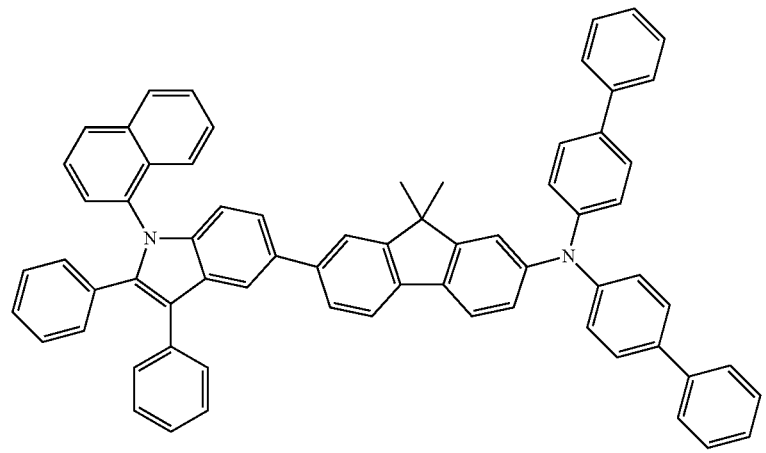

39
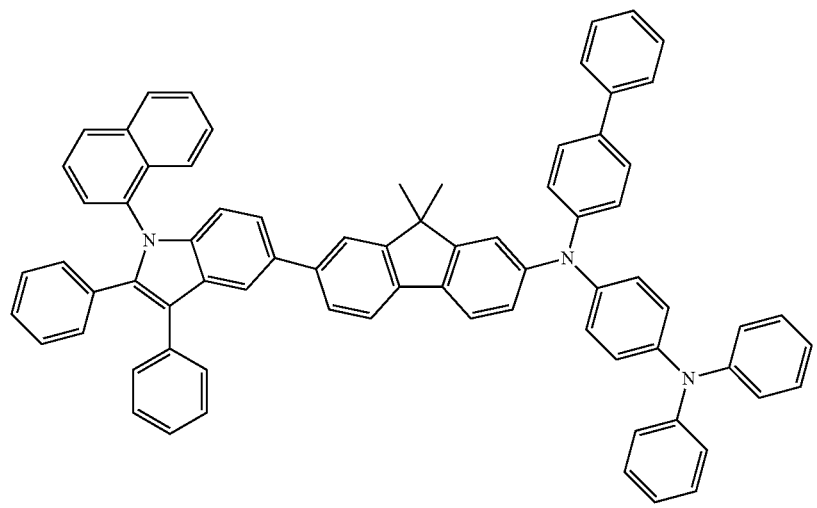
40
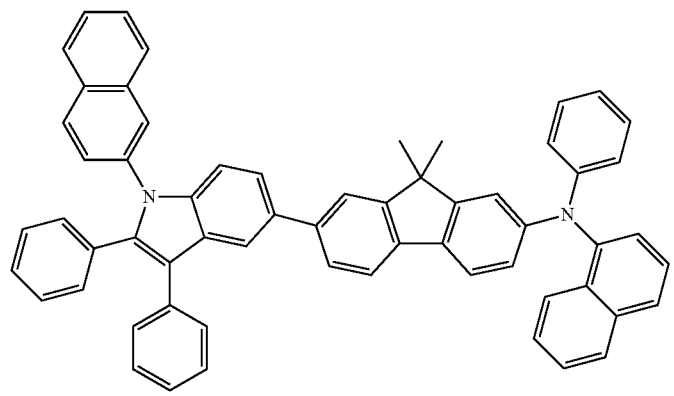
41
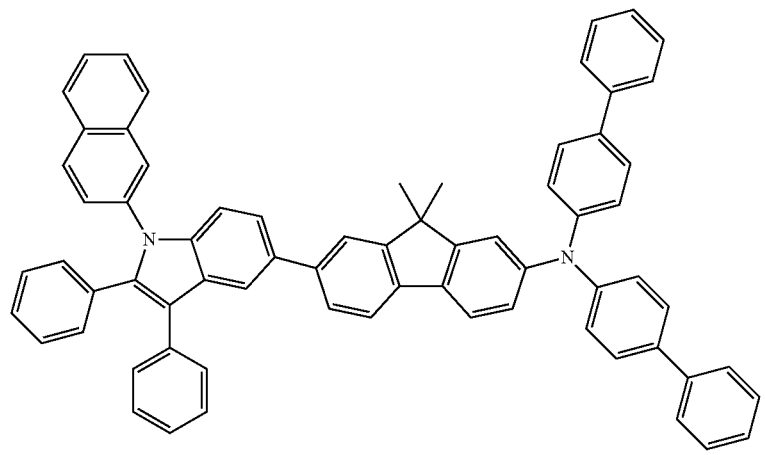

-continued
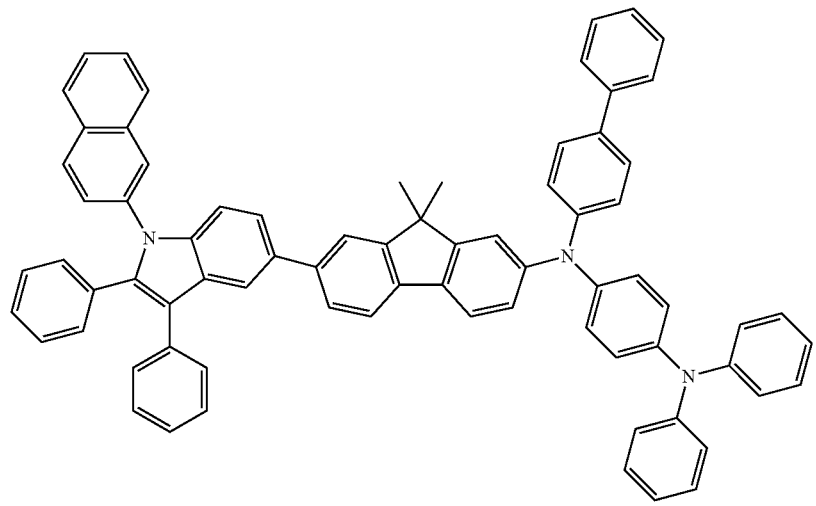
42
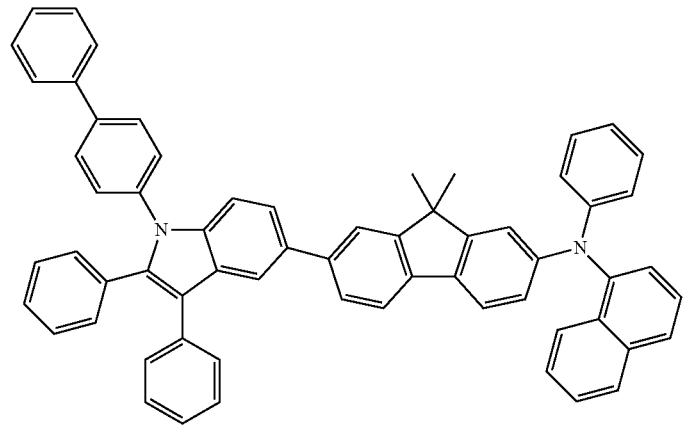
43
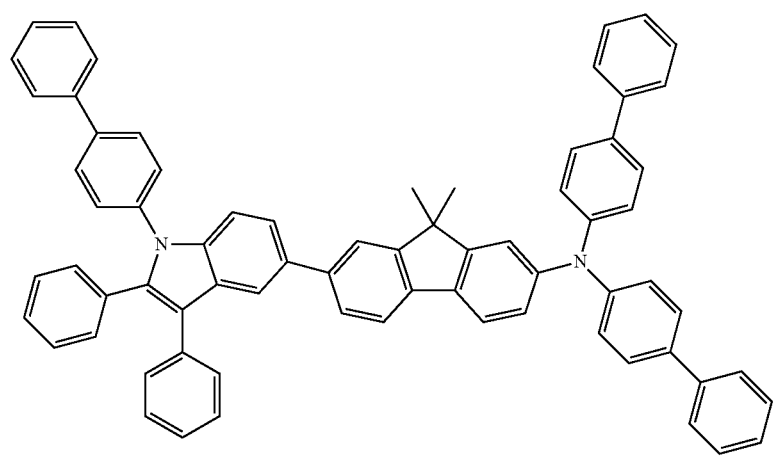
44

45
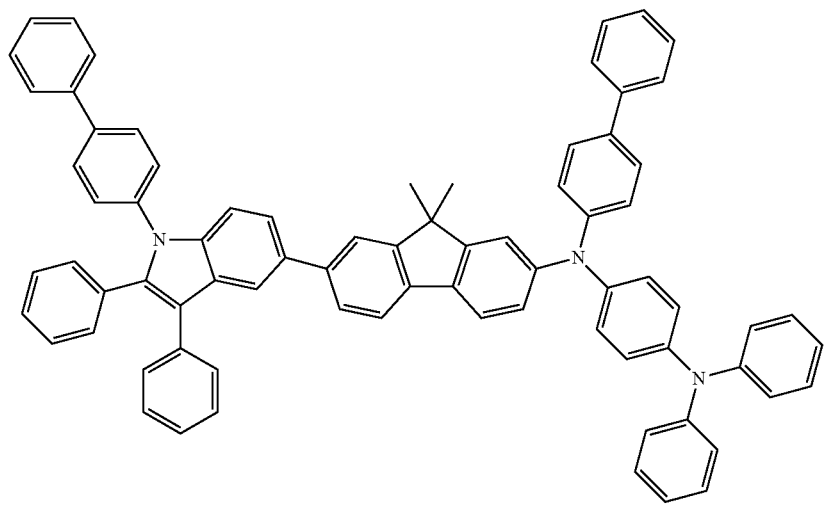
46
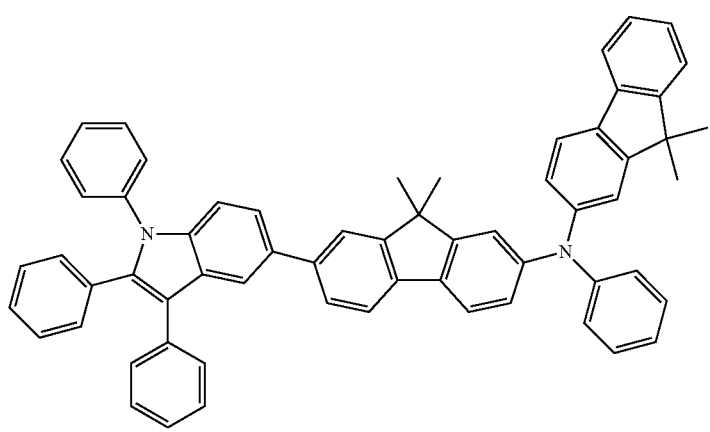
47
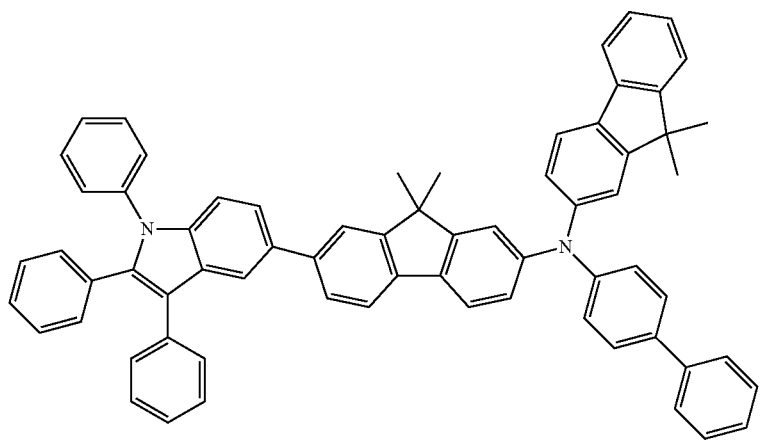

-continued
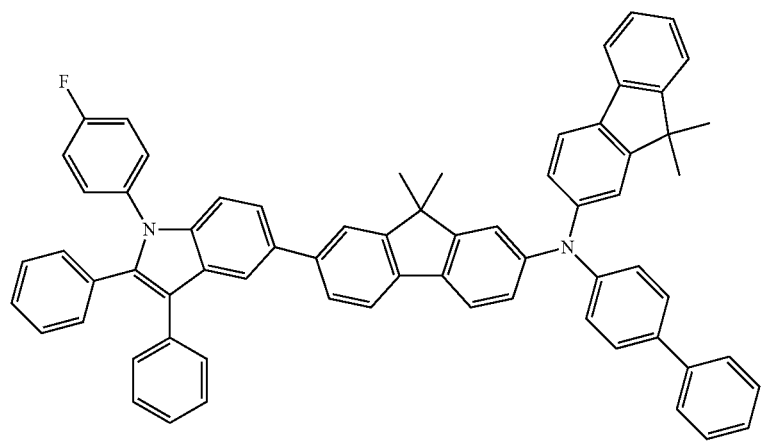
48
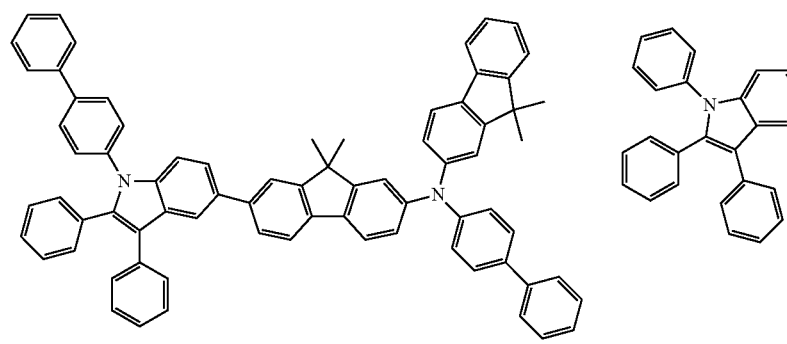
49 50
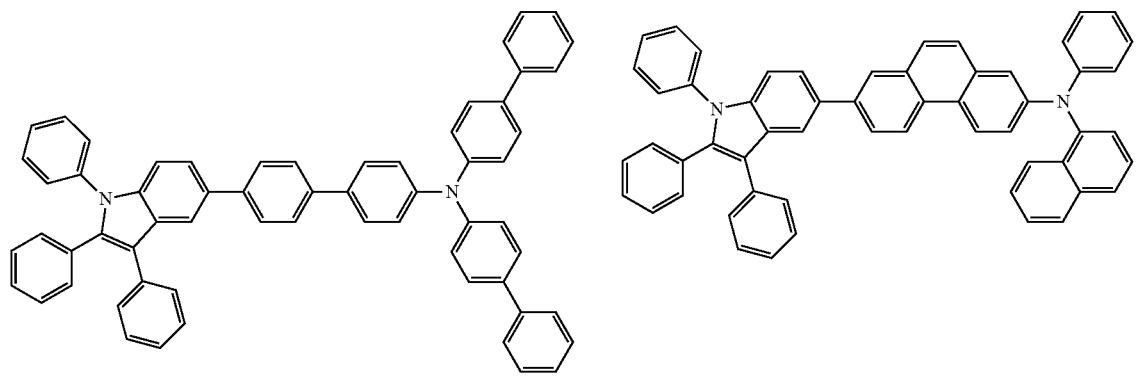
51 52
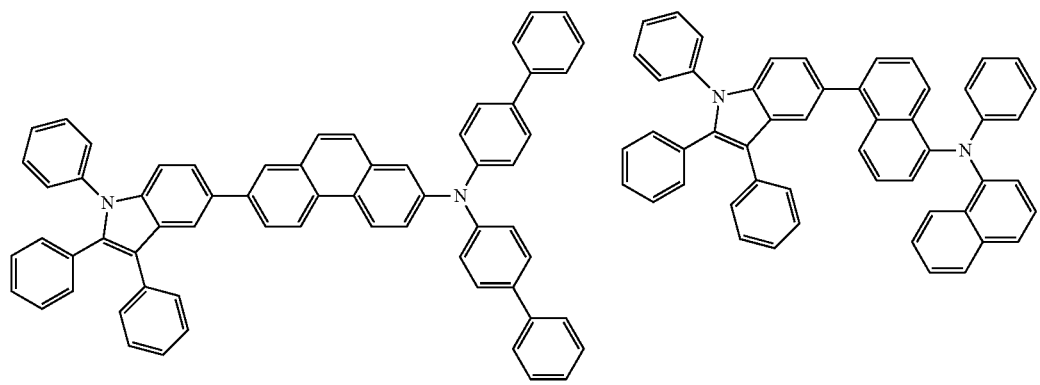
53 54

-continued
55
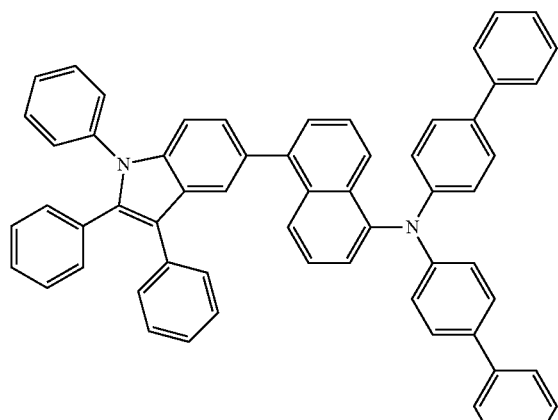
56
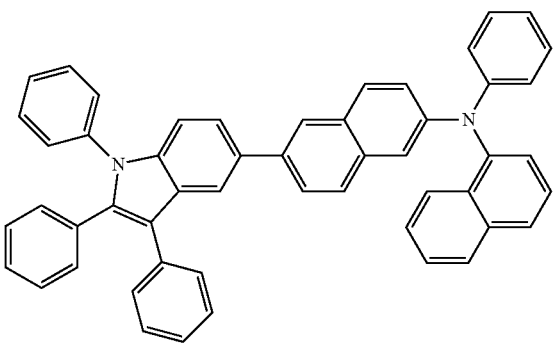
57
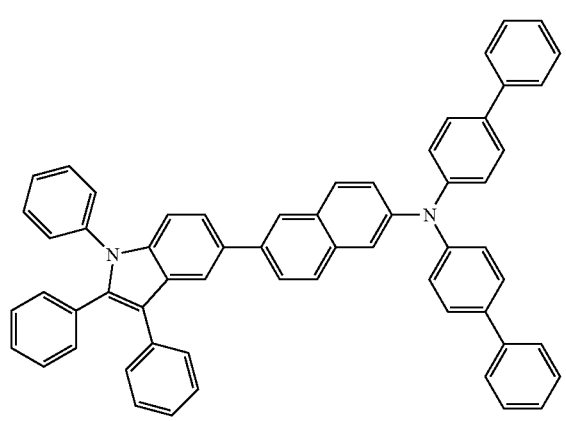
58
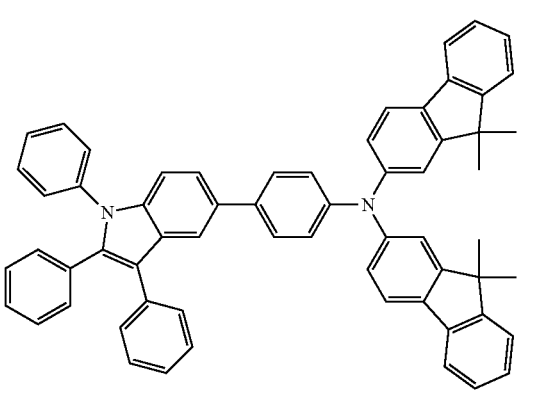
59
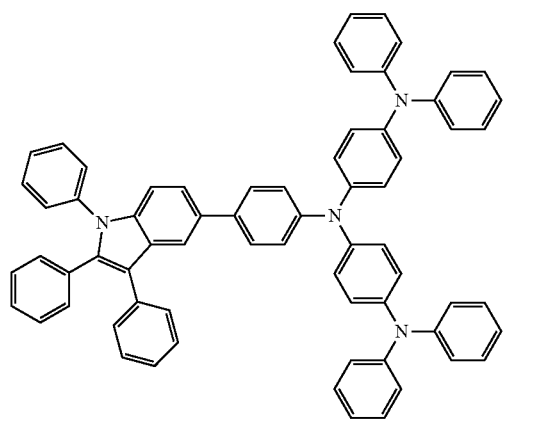
60
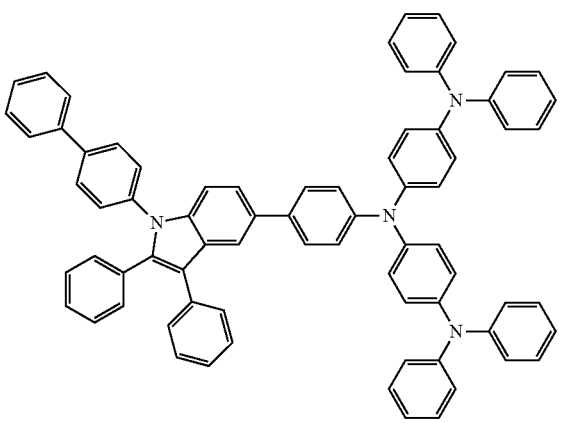
61
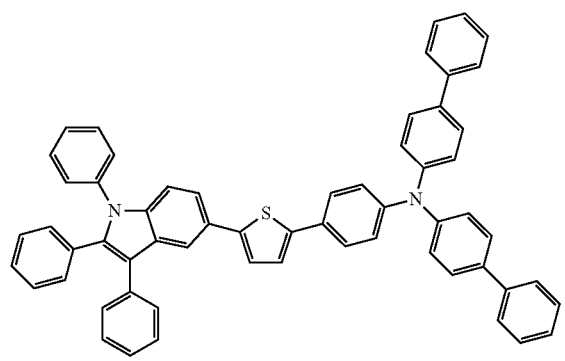
62
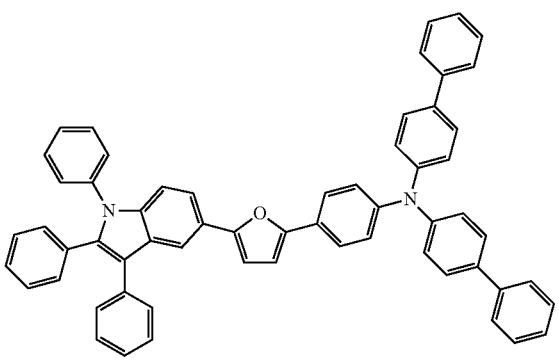

63
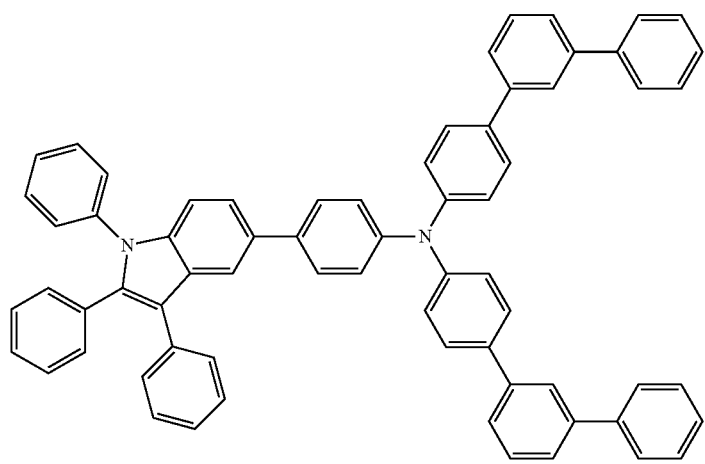
64
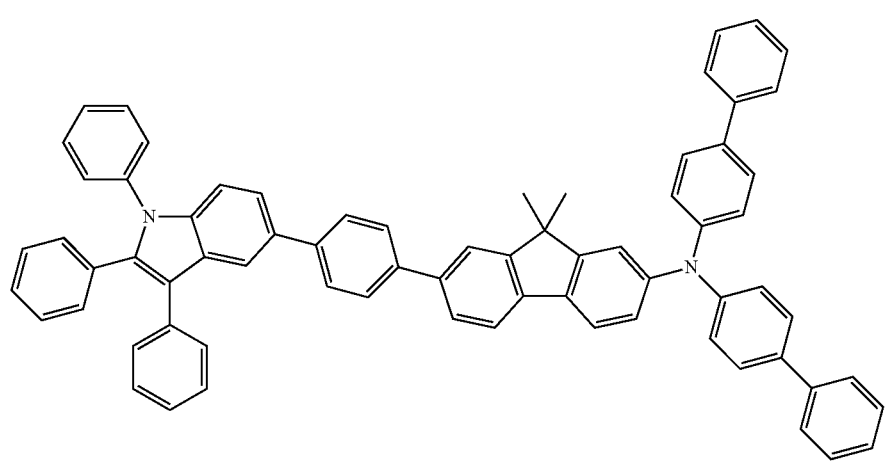
65
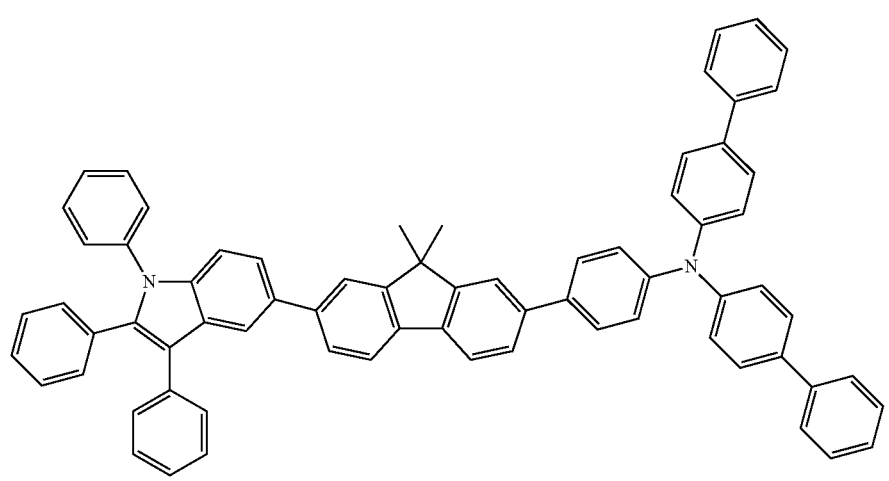

-continued
66
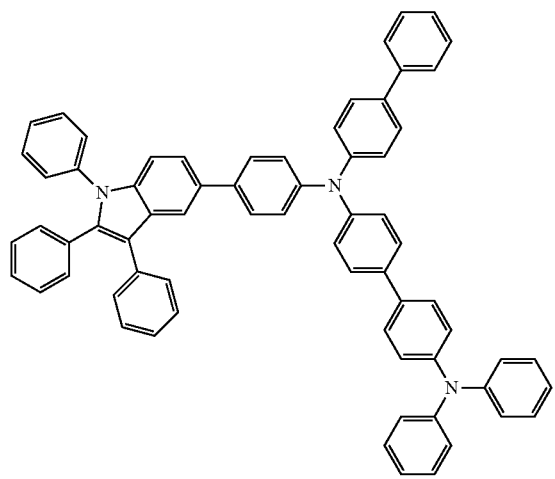
67
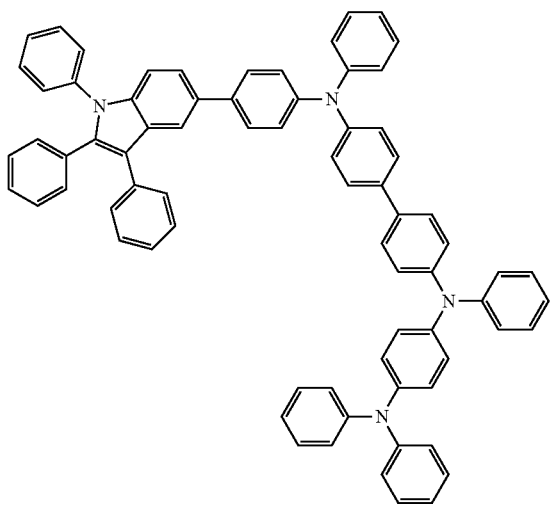
68
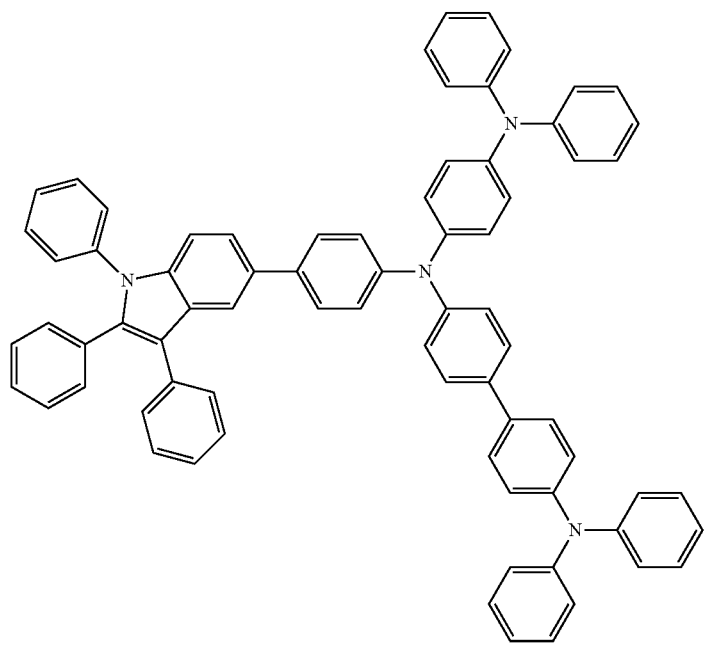
69
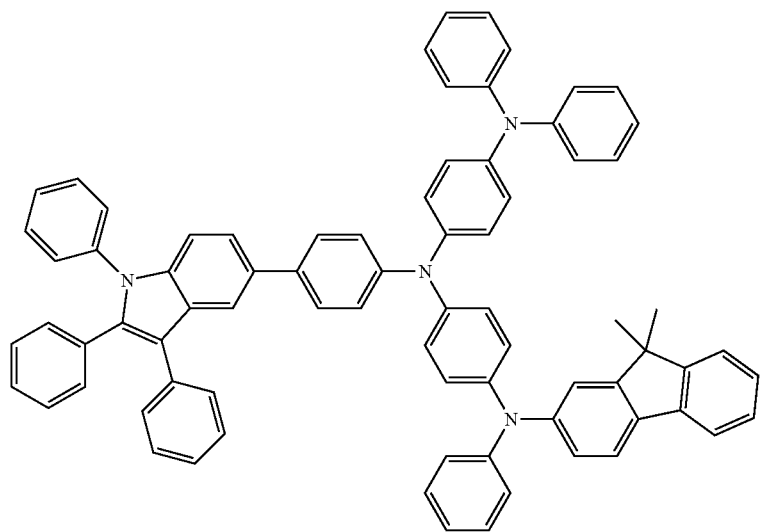

-continued
70
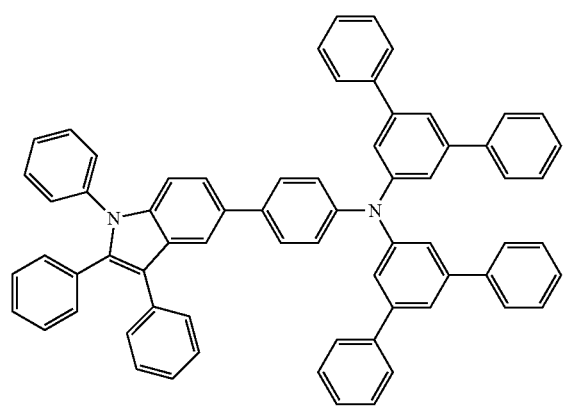
71
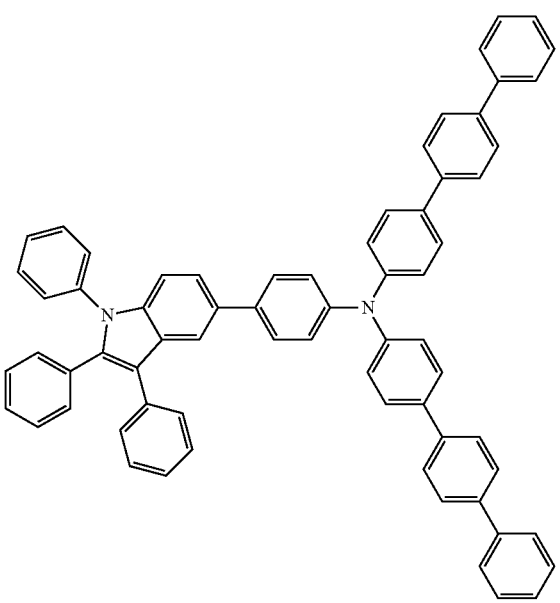
72
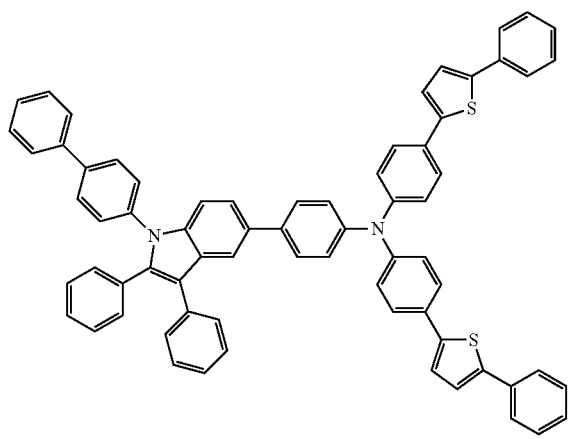
73
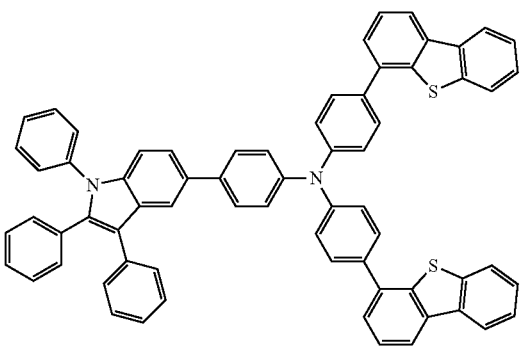
74
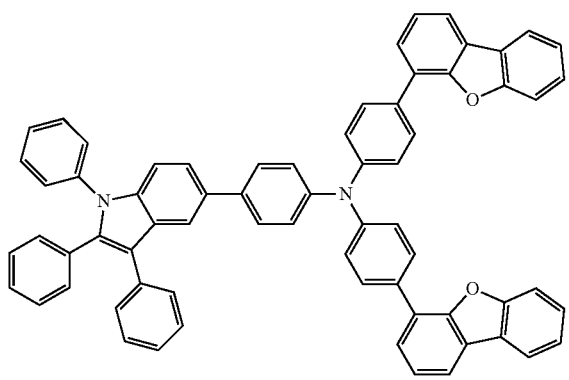
75
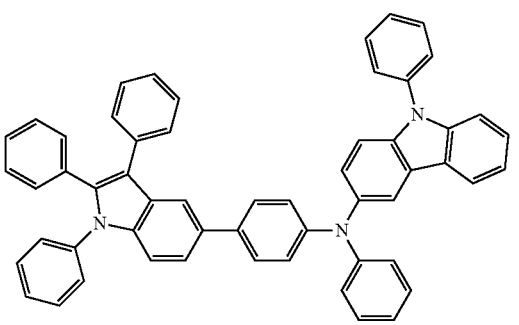

76
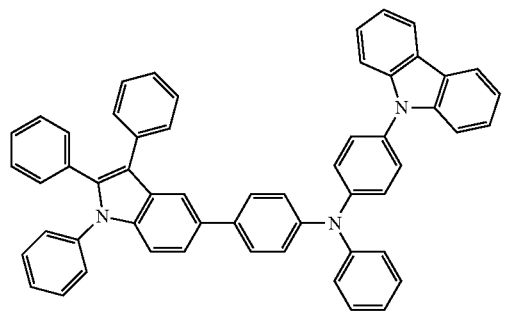
77
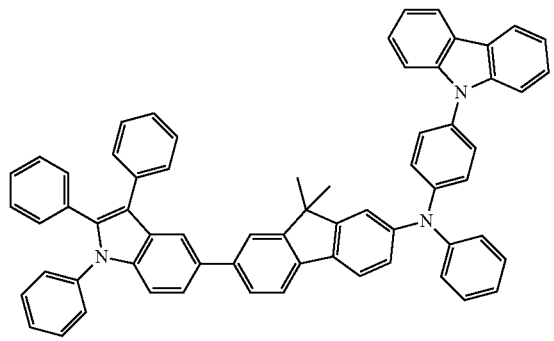
78
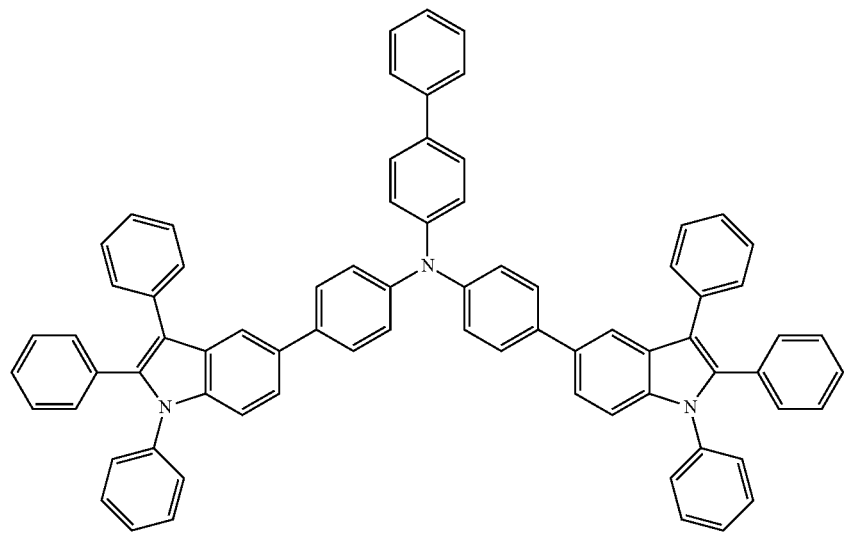
79
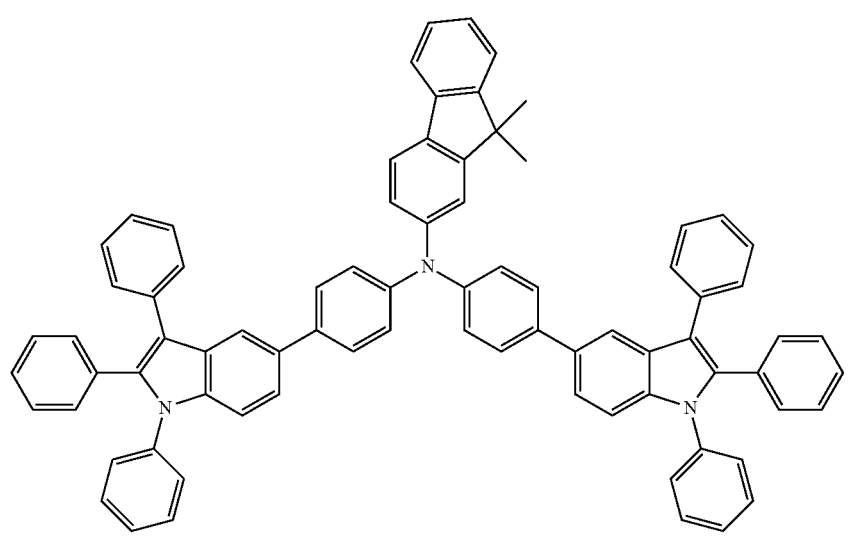

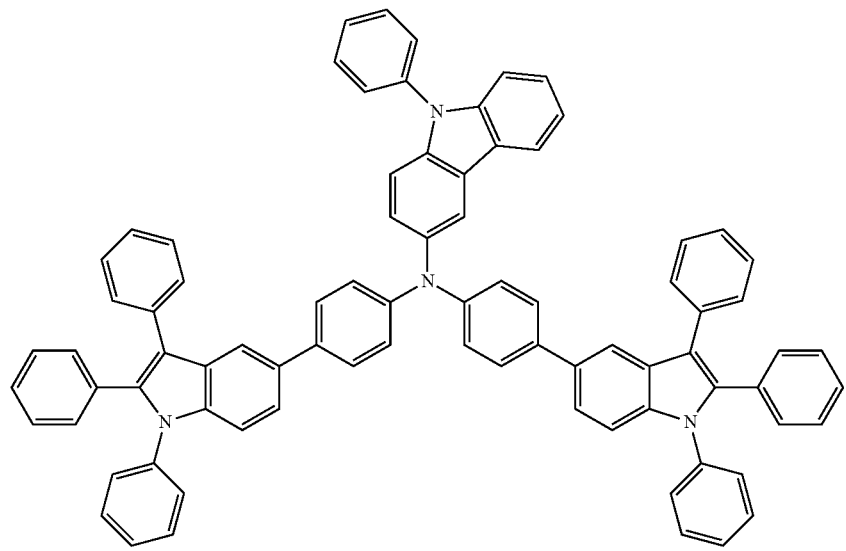
80
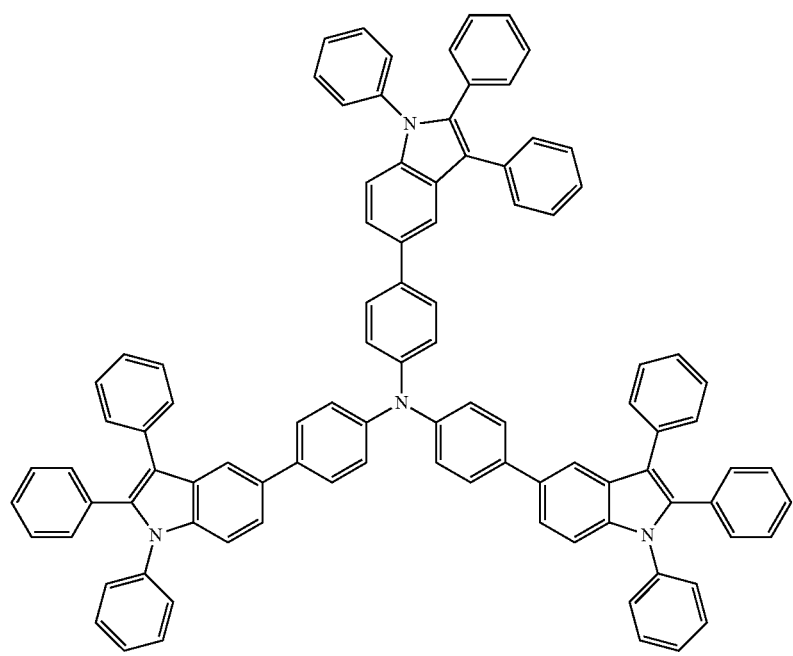
81

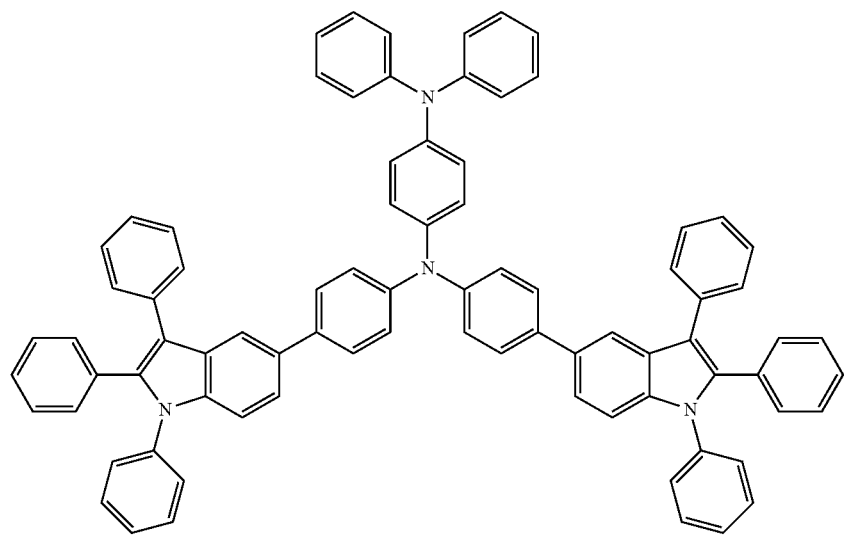

82

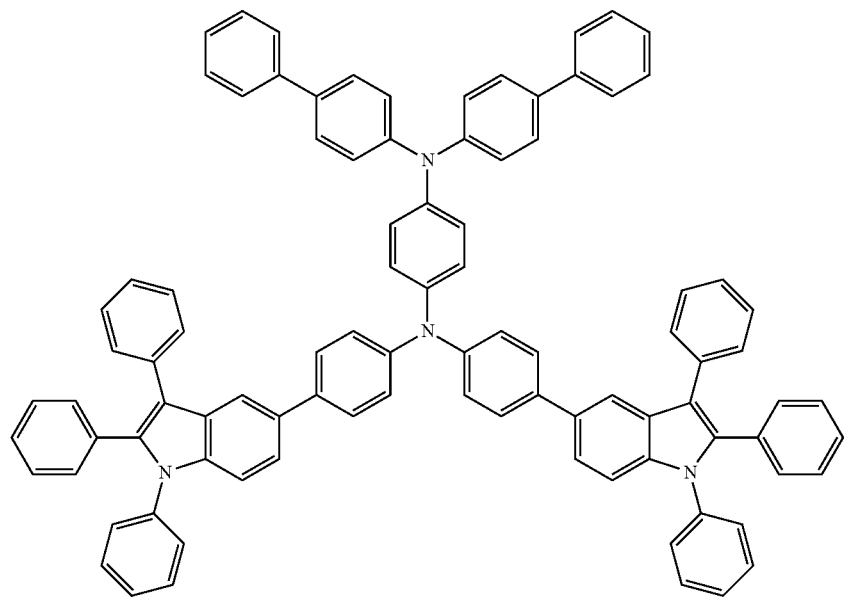

83

In some embodiments, for example, the heteroarylamine compound of Formula 1 is selected from Compound 1, Compound 2, Compound 8, Compound 29, Compound 32, Compound 52, Compound 58, and Compound 81.

According to other embodiments of the present invention, a method of synthesizing a heteroarylamine compound of Formula 1 is provided. Initially, benzophenone hydrazone, sodium butoxide, palladium diacetate and 2-dicyclohexylphospino-2',4',6'-triisopropylbiphenyl are added to a heteroarylamine compound represented by Formula 7 below. The components are mixed together and heated to obtain a compound represented by Formula 8 below.

Formula 7

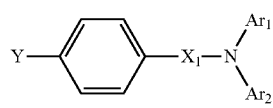

In Formula 7, $X_1$, $Ar_1$, and $Ar_2$ are as defined above in connection with Formula 1, and Y is a halogen atom selected from bromine, iodine, and chlorine.

Formula 8

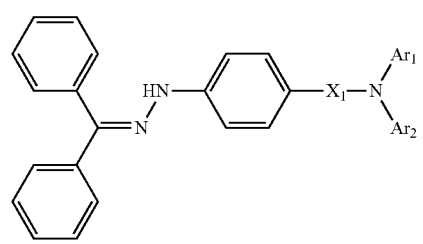

In Formula 8, $X_1$, $Ar_1$, and $Ar_2$ are as defined above in connection with Formula 1.

In the synthesis method, the amount of benzophenone hydrazone may be about 1.05 to about 1.2 moles based on 1 mole of the heteroarylamine compound of Formula 7. The amount of sodium butoxide may be about 1.2 to about 1.5 moles based on 1 mole of the heteroarylamine compound of Formula 7. In addition, the amount of palladium diacetate may be about 0.02 to about 0.05 moles, and the amount of 2-dicyclohexylphospino-2',4',6'-triisopropylbiphenyl may be about 0.02 to about 0.05 moles, based on 1 mole of the heteroarylamine compound of Formula 7.

The heating may be performed at a temperature of about 80 to about 100° C. When the heating temperature is within this range, a high yield of the compound of Formula 8 may be obtained.

Next, p-toluenesulfonic acid monohydrate, benzylphenylketone and a solvent are added to the compound of Formula 8, and the components are heated. When the reaction is completed, the reaction product is worked up to obtain the heteroarylamine compound of Formula 1. The heating for the reaction may be performed at a temperature of about 60 to about 100° C. When the heating temperature is within this range, a high yield of the heteroarylamine compound of Formula 1 may be obtained.

The amount of p-toluenesulfonic acid monohydrate may be about 1.5 to about 2.0 moles, and the amount of benzylphenylketone may be about 1.5 to about 2.0 moles, based on 1 mole of the compound of Formula 8.

According to other embodiments of the present invention, an organic light-emitting device includes a first electrode, a second electrode, and an organic layer between the first electrode and the second electrode. The organic layer includes at least one organic layer containing the heteroarylamine compound of Formula 1 described above. The heteroarylamine compound may be used exclusively or may be included in a mixture.

The at least one organic layer containing the heteroarylamine compound of Formula 1 may include a hole injection layer, a hole transport layer, or a single layer having both hole injection and hole transport capabilities. The at least one organic layer containing the heteroarylamine compound of Formula 1 may include an emission layer. The heteroarylamine compound of Formula 1 may be used as a host material for a blue, green, or red emission layer of a fluorescent or phosphorescent device.

In some embodiments, for example, the at least one organic layer containing the heteroarylamine compound represented by Formula 1 may include a hole injection layer or a hole transport layer.

The organic layer may include a hole injection layer, a hole transport layer, and an emission layer, wherein the hole injection layer or the hole transport layer may contain the heteroarylamine compound of Formula 1, and the emission layer may contain an anthracene compound.

Alternatively, the organic layer may include a hole injection layer, a hole transport layer and an emission layer, wherein the hole injection layer or the hole transport layer may contain the heteroarylamine compound of Formula 1, and the emission layer may contain an arylamine or heteroarylamine compound or a styryl compound.

The first electrode may be an anode, and the second electrode may be a cathode, but the reverse is also possible.

The organic light-emitting device described above may also include at least one layer selected from a hole injection layer, a hole transport layer, an electron blocking layer, an emission layer, a hole blocking layer, an electron transport layer and an electron injection layer. These organic layers may have double-layered structures.

An organic light-emitting device according to embodiments of the present invention may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. An organic light-emitting device according other embodiments may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure.

An organic light-emitting device according to embodiments of the present invention may have various structures, such as a top emission type organic light-emitting device structure or a bottom emission type organic light-emitting device structure.

According to embodiments of the present invention, a method of manufacturing an organic light-emitting device is provided. FIG. 1 illustrates the structure of an organic light-emitting device according to an embodiment of the present invention. Referring to FIG. 1, according to embodiments of the present invention, an organic light-emitting device includes a substrate, a first electrode (anode), a hole injection layer (HIL), a hole transport layer (HTL), an emission layer (EML), an electron transport layer (ETL), an electron injection layer (EIL), and a second electrode (cathode).

The first electrode is formed on the substrate by deposition or sputtering. The first electrode may be formed of a first electrode material having a high work function. The first electrode may be an anode or a cathode. The substrate may be any substrate conventionally used in organic light-emitting devices, and may be, for example, a glass substrate or a transparent plastic substrate having good mechanical strength, thermal stability, transparency, surface planarity, handling convenience, and water resistance. The first electrode material may include at least one material selected from indium tin oxide (ITO), indium zinc oxide (IZO), tin oxide ($SnO_2$), zinc oxide (ZnO), aluminum (Al), silver (Ag), and magnesium (Mg), which have good conductivity, and may form a transparent or reflective electrode.

A HIL may be formed on the first electrode by vacuum deposition, spin coating, casting, Langmuir Blodgett (LB) deposition, or the like. When the HIL is formed by vacuum deposition, the vacuum deposition conditions may vary according to the compound used to form the HIL and the desired structure and thermal properties of the HIL to be formed. In general, however, the vacuum deposition may be performed at a deposition temperature of about 100° C. to about 500° C., under a pressure of about $10^{-8}$ torr to about $10^{-3}$ torr, at a deposition speed of about 0.01 to about 100 Å/sec, and to a layer thickness of about 10 Å to about 5 µm.

When the HIL is formed by spin coating, the coating conditions may vary according to the compound used to form the HIL and the desired structure and thermal properties of the HIL to be formed. In general, however, the coating speed may be about 2000 rpm to about 5000 rpm, and the temperature for heat treatment (performed to remove the solvent after coating) may be about 80° C. to about 200° C.

The HIL material may include the heteroarylamine compound of Formula 1 described above. Alternatively, any known HIL material may be used. Nonlimiting examples of HIL materials include phthalocyanine compounds (such as copper phthalocyanine), star-burst type amine derivatives (such as TCTA, 4,4',4''-tris(3-methylphenylphenylamino) triphenylamine (m-MTDATA), N,N'-di(1-naphthyl)-N,N'-diphenylbenzidine) (NPB), TDATA, and 2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and (polyaniline)/poly(4-styrenesulfonate) (PANI/PSS).

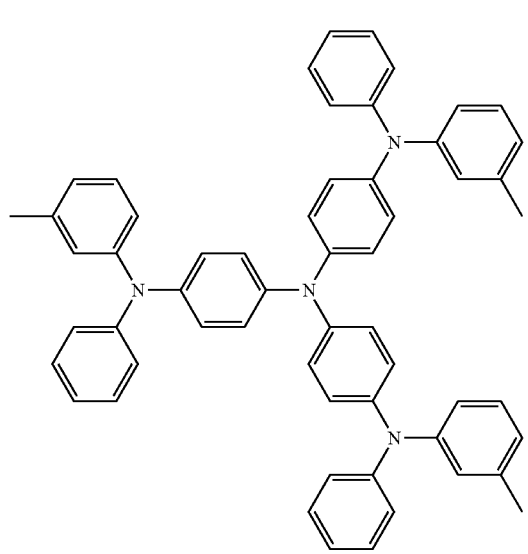

m-MTDATA

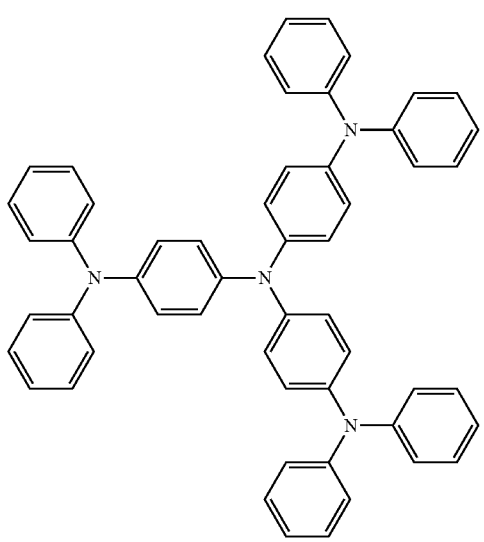

TDATA

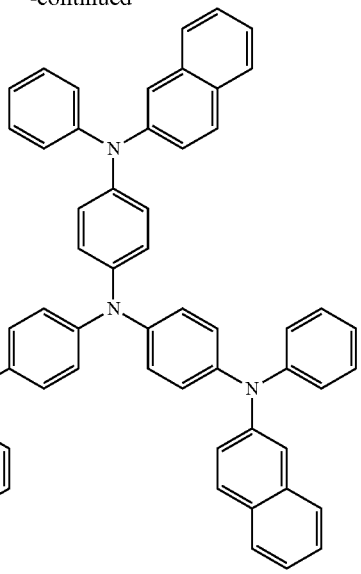

2-TNATA

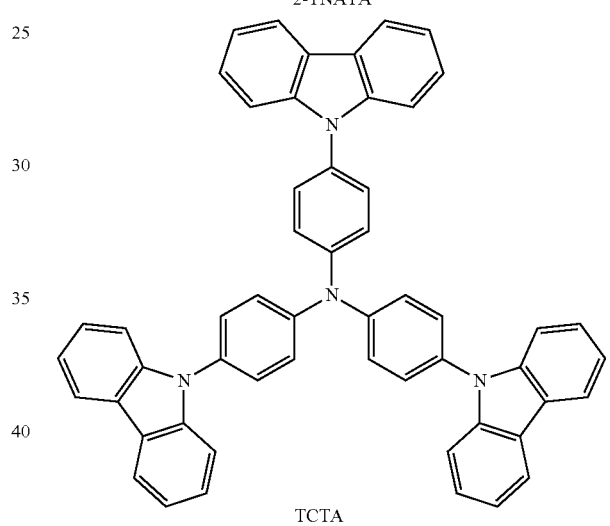

TCTA

The thickness of the HIL may be about 100 to about 10,000 Å. In some embodiments, for example, the thickness of the HIL is about 100 to about 1,000 Å. When the HIL has a thickness within these ranges, the HIL has good hole injection characteristics without increasing driving voltage.

A HTL may be formed on the HIL by vacuum deposition, spin coating, casting, LB deposition, or the like. When the HTL is formed by vacuum deposition or spin coating, the conditions for deposition and coating are similar to those for the formation of the HIL, although the conditions for the deposition and coating may vary according to the material used to form the HTL.

The HTL material may include the heteroarylamine compound of Formula 1 described above. Alternatively, when the heteroarylamine compound of Formula 1 is used as a material for the EML or HIL, the HTL may be formed of any suitable material for forming a HTL. Nonlimiting examples of suitable materials for the HTL include carbazole derivatives (such as N-phenylcarbazole and polyvinylcarbazole), and amine derivatives having condensed aromatic rings (such as 4,4'-bis[N-(1-naphthyl)-N-phenylamino]biphenyl (NPB), N,N'-bis(3-methylphenyl)-N,N'-diphenyl-[1,1-biphenyl]-4,4'-diamine (TPD)).

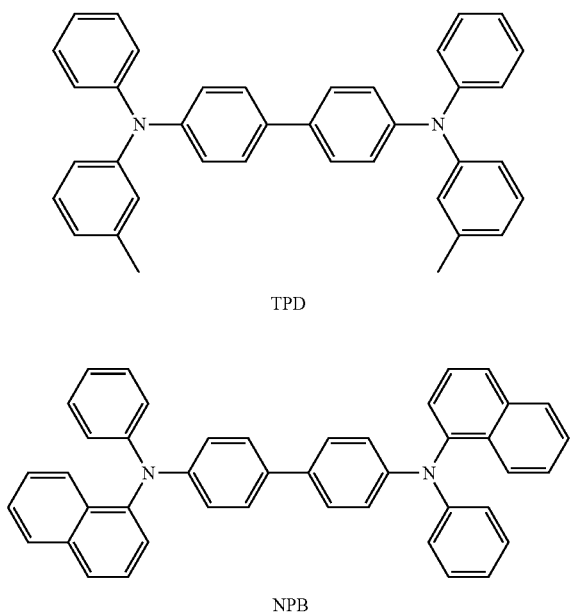

TPD

NPB

The thickness of the HTL may be about 50 to about 1,000 Å. In some embodiments, for example, the thickness of the HTL is about 100 to about 600 Å. When the HTL has a thickness within these ranges, the HTL has good hole transporting characteristics without substantially increasing driving voltage.

Optionally, an electron blocking layer may be formed on the HTL. The electron blocking layer blocks migration of electrons into the HTL. The electron blocking layer may include, for example, TATT represented by the following formula:

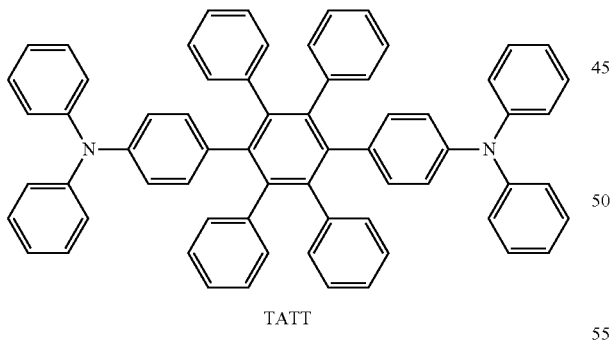

TATT

The thickness of the electron blocking layer may be about 50 to about 200 Å. When the electron blocking layer has a thickness within this range, the electron blocking layer has good electron blocking characteristics without substantially increasing driving voltage.

The EML is formed on the resultant structure. The EML may be formed by vacuum deposition, spin coating, casting, or LB deposition. When the EML is formed by vacuum deposition or spin coating, the conditions for deposition and coating are similar to those for the formation of the HIL, although the conditions for deposition and coating may vary according to the material used to form the EML.

The EML may include the heteroarylamine compound of Formula 1. The heteroarylamine compound of Formula 1 may be used as a host of the EML. Alternatively, when the heteroarylamine compound of Formula 1 is used to form the HIL or the HTL, the EML of the organic light-emitting device may be formed of any suitable light emitting material for forming the EML of an organic light-emitting device. Nonlimiting examples of suitable light-emitting materials for forming the EML include known hosts and dopants. Dopants used to form the EML may include either a fluorescent dopant or a phosphorescent dopant.

Nonlimiting examples of hosts include $Alq_3$, 4,4'-N,N'-dicarbazole-biphenyl (CPB), 9,10-di(naphthalene-2-yl)anthracene (ADN), distyrylarylene (DSA), arylamine and heteroarylamine compounds, anthracene compounds having symmetrical or asymmetrical structures, pyrene compounds having symmetrical or asymmetrical structures, spirofluorene compounds, and fluorene compounds.

Either a fluorescent dopant or a phosphorescent dopant may be used as a dopant for forming the EML. Nonlimiting examples of the fluorescent dopant include styryl compounds, arylamine or heteroarylamine compounds, styrylheteroarylamine compounds, and aminopyrene compounds. Nonlimiting examples of the phosphorescent dopant include $Ir(PPy)_3$ (PPy=phenylpyridine) (green), compound A represented by the following formula, $F_2Irpic$, RD 61 (which is a red phosphorescent dopant available from UDC), and metal-complex compounds including iridium (Ir), ruthenium (Ru), palladium (Pd), platinum (Pt), osmium (Os), or rhenium (Re) as a core metal.

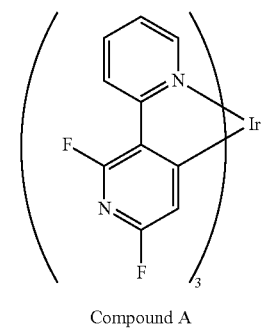

Compound A

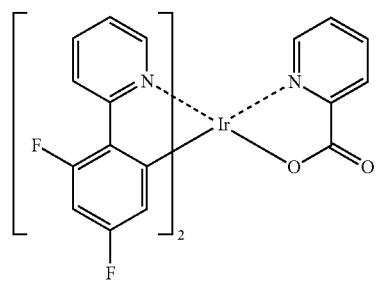

$F_2Irpic$

Nonlimiting examples of red dopants include platinum(II) octaethylporphyrin (PtOEP), $Ir(piq)_3$, $Btp_2Ir(acac)$, and DCJTB.

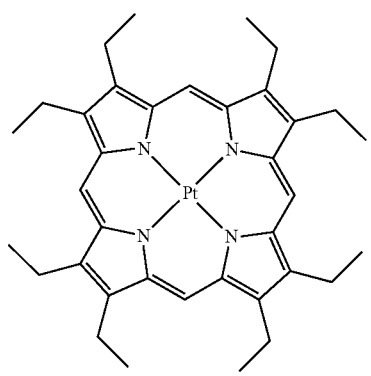

PtOEP

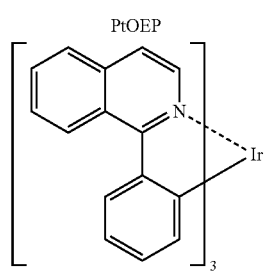

Ir(piq)₃

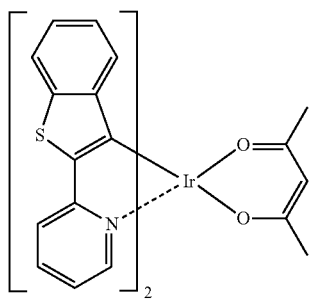

Btp₂Ir(acac)

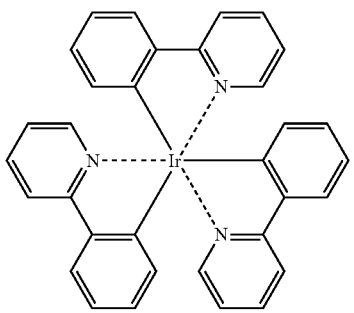

Ir(ppy)₃

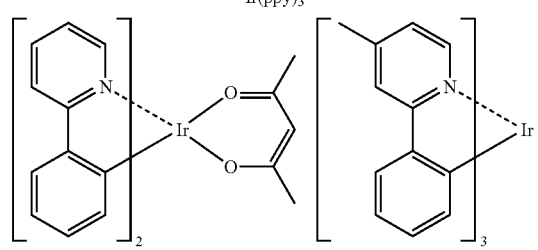

Ir(ppy)₂(acac)    Ir(mpyp)₃

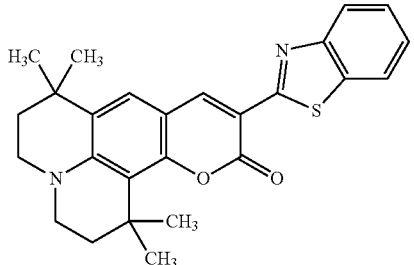

C545T

Nonlimiting examples of green dopants include Ir(ppy)₃ (where "ppy" denotes phenylpyridine), Ir(ppy)₂(acac), Ir(m-pyp)₃, and C545T.

Nonlimiting examples of blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl pherylene (TBP).

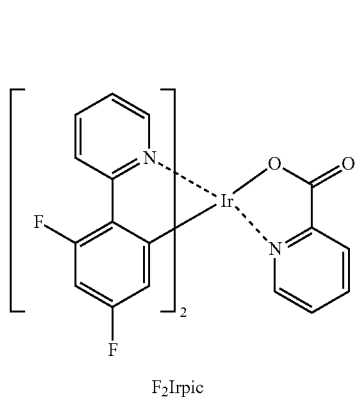

F₂Irpic

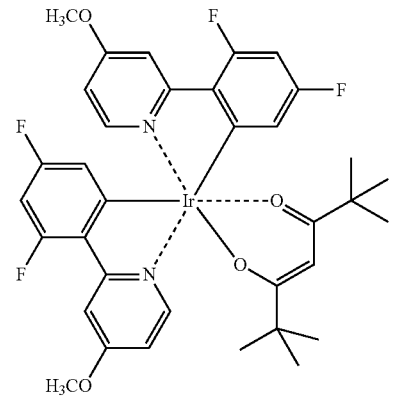

Ir(ppy)₃

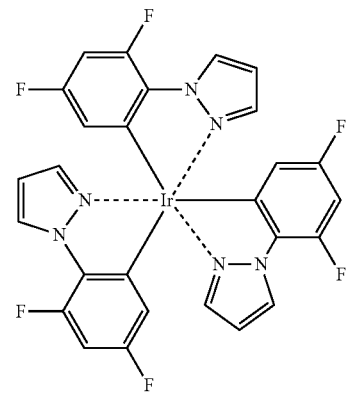

Ir(dfppz)₃

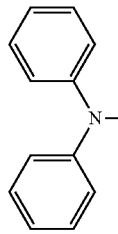

DPAVBi

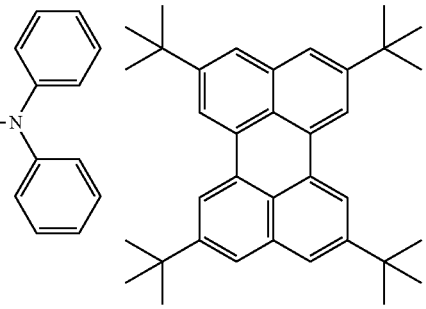

TBP

The amount of the dopant may be about 0.1 to about 20 parts by weight based on 100 parts by weight of the EML material, which is the total weight of the host and dopant. In some embodiments, for example, the amount of the dopant is about 0.5 to about 12 parts by weight based on 100 parts by weight of the EML material. When the amount of the dopant is within these ranges, concentration quenching may be substantially prevented.

The thickness of the EML may be about 100 to about 1000 Å. In some embodiments, for example, the thickness of the EML is about 200 to about 600 Å. When the thickness of the EML is within these ranges, good light emission characteristics may be obtained without increasing driving voltage.

When the EML includes a phosphorescent dopant, a hole blocking layer (HBL, not shown in FIG. 1) may be formed on the EML in order to prevent diffusion of triplet excitons or holes into the ETL. The HBL may be formed of any suitable material without limitation. Nonlimiting examples of suitable materials for the HBL include oxadiazole derivatives, triazole derivatives, phenanthroline derivatives, bis(2-methyl-8-quinolato)-(p-phenylphenolato)-aluminum (Balq), bathocuproine (BCP), and tris(N-arylbenzimidazole) (TPBI).

The thickness of the HBL may be about 50 to about 1000 Å. In some embodiments, for example, the thickness of the HBL is about 100 to about 300 Å. When the thickness of the HBL is within these ranges, good hole-blocking characteristics may be obtained without increasing driving voltage.

The ETL may be formed on the HBL or EML by vacuum deposition, spin coating, or casting. When the ETL is formed by vacuum deposition or spin coating, the deposition and coating conditions may be similar to those for formation of the HIL, although the deposition and coating conditions may vary according to the compound used to form the ETL.

The ETL may be formed of any suitable material without limitation. Nonlimiting examples of suitable materials for the ETL include quinoline derivatives, for example, tris(8-quinolinorate)aluminum (Alq3), TAZ, and Balq.

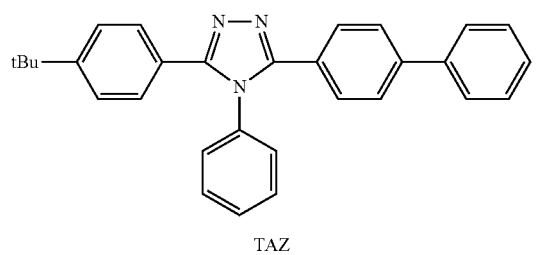

TAZ

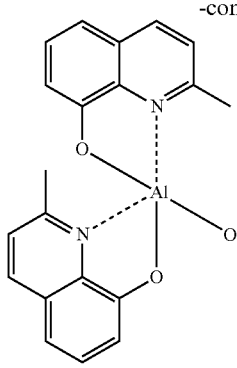

BAlq

The thickness of the ETL may be about 100 to about 1000 Å. In some embodiments, for example, the thickness of the ETL is about 100 to about 500 Å. When the ETL has a thickness within these ranges, the ETL may have good electron transport characteristics without substantially increasing driving voltage.

In addition, an electron injection layer (EIL) for facilitating the injection of electrons from the cathode may be formed on the ETL. Nonlimiting examples of materials for the EIL include $BaF_2$, LiF, NaCl, CsF, $Li_2O$, BaO, and Liq.

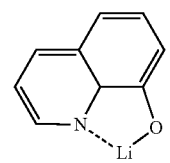

Liq

The deposition or coating conditions used to form the EIL may be similar to those used to form the HIL, although the deposition and coating conditions may vary according to the material used to form the EIL.

The thickness of the EIL may be about 1 to about 100 Å. In some embodiments, for example, the thickness of the EIL is about 5 to about 90 Å. When the EIL has a thickness within these ranges, the EIL may have good electron injection characteristics without substantially increasing driving voltage.

Finally, the second electrode may be formed on the EIL by vacuum deposition or sputtering. The second electrode may be a cathode or an anode. The material for forming the second electrode may be selected from metals, alloys, electrically conductive compounds, materials which have a low work function, and mixtures thereof. Nonlimiting examples of materials for the second electrode include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission type organic light-emitting device, a transparent cathode formed of a transparent material such as ITO or IZO may be used as the second electrode.

The organic light-emitting device according to embodiments of the present invention may be included in various types of flat panel display devices, such as in passive matrix organic light-emitting display devices or active matrix organic light-emitting display devices. When the organic light-emitting device is included in an active matrix organic light-emitting display device including a thin-film transistor, the first electrode on the substrate may function as a pixel electrode, and be electrically connected to a source electrode or a drain electrode of the thin-film transistor. Moreover, the organic light-emitting device may also be included in a flat panel display device having a double-sided screen.

According to embodiments of the present invention, at least one layer of the organic light-emitting device may be formed of the heteroarylamine compound of Formula 1 and can be formed using a deposition method or a wet method of coating a solution of the heteroarylamine compound of Formula 1.

The following examples are presented for illustrative purposes only, and do not limit the scope of the present invention.

Synthesis Example 1

Synthesis of Intermediate 1

7 g (30 mmol) of 2-bromobiphenyl, 7.62 g (45 mmol) of aminobiphenyl, 4.3 g (45 mmol) of t-BuONa, 0.55 g (0.6 mmol) of $Pd_2(dba)_3$, and 0.12 g (0.6 mmol) of $P(t-Bu)_3$ were dissolved in 100 mL of toluene and stirred at 90° C. for 3 hours.

After the reaction was completed, the reaction product was cooled to room temperature and extracted three times with distilled water and 100 ml of diethylether. An organic layer was collected and dried using magnesium sulfate to evaporate the solvent. The residue was separated and purified using silica gel column chromatography to obtain 8.77 g (yield: 91%) of intermediate 1. This compound was identified using high-resolution mass spectrometry (HR-MS). $C_{24}H_{19}N$ calc.: 321.1517; and found: 321.1519.

Synthesis Example 2

Synthesis of Intermediate 2

Intermediate 2 was synthesized with a yield of 87% in the same manner as Intermediate 1, except that 2-bromo-9,9-dimethylfluorene was used instead of 2-bromobiphenyl. This compound was identified using HR-MS. $C_{27}H_{23}N$ calc.: 361.1830; and found: 361.1833.

Synthesis Example 3

Synthesis of Intermediate 3

Intermediate 3 was synthesized with a yield of 85% in the same manner as Intermediate 2, except that 2-amino-9,9-dimethylfluorene was used instead of 4-aminobiphenyl. This compound was identified using HR-MS. $C_{30}H_{27}N$ calc.: 401.2143; and found: 401.2140.

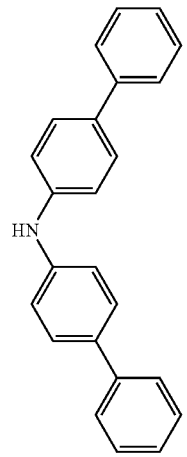

Intermediate 1

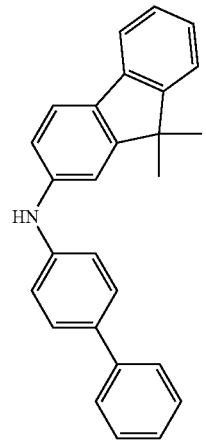

Intermediate 2

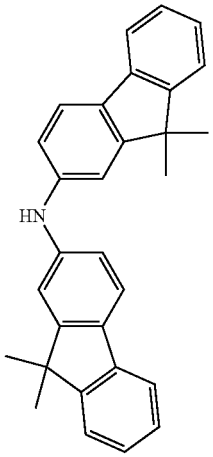

Intermediate 3

Synthesis Example 4

Synthesis of Intermediate 4

22.3 g (50 mmol) of 2,7-diiodo-9,9-dimethylfluorene, 3.21 g (10 mmol) of Intermediate 1, 2.88 g (30 mmol) of t-BuONa, 0.28 g (0.3 mmol) of $Pd_2(dba)_3$, and 0.6 g (0.3 mmol) of $P(t-Bu)_3$ were dissolved in 100 ml of toluene and stirred at 90°

C. for 3 hours. After the reaction was completed, the reaction product was cooled to room temperature and extracted three times with distilled water and 100 ml of diethylether. An organic layer was collected and dried using magnesium sulfate to evaporate the solvent. The residue was separated and purified using silica gel column chromatography to obtain 3 g of (yield: 47%) of Intermediate 4. This compound was identified using HR-MS. C39H30IN calc.: 639.1423; and found: 639.1419.

Synthesis Example 5

Synthesis of Intermediate 5

Intermediate 5 was synthesized with a yield of 52% in the same manner as Intermediate 4, except that 2,7-diiodophenanthrene was used instead of 2,7-diiodo-9,9-dimethylfluorene, and N-phenyl-2-naphthylamine was used instead of Intermediate 1. This compound was identified using HR-MS. $C_{30}H_{20}IN$ calc.: 521.0640; and found: 521.0637.

Intermediate 4

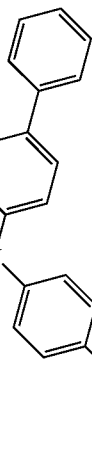

Intermediate 5

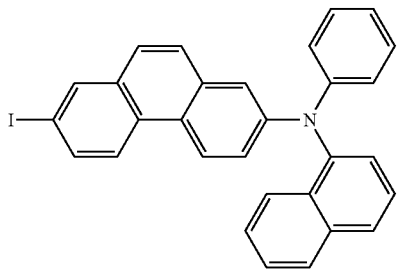

Synthesis Example 6

Synthesis of Intermediate 6

16.2 g (45 mmol) of 4-bromo-4'-iodo-biphenyl, 6.58 g (30 mmol) of N-phenyl-2-naphthylamine, 4.3 g (45 mmol) of t-BuONa, 0.55 g (0.6 mmol) of $Pd_2(dba)_3$, and 0.12 g (0.6 mmol) of $P(t-Bu)_3$ were dissolved in 100 mL of toluene and stirred at 90° C. for 3 hours. After the reaction was completed, the reaction product was cooled to room temperature and extracted three times with distilled water and 100 ml of diethylether. An organic layer was collected and dried using magnesium sulfate to evaporate the solvent. The residue was separated and purified using silica gel column chromatography to obtain 8.38 g (yield: 62%) of Intermediate 6. This compound was identified using HR-MS. $C_{28}H_{20}BrN$ calc.: 449.0779; and found: 449.0775.

Synthesis Example 7

Synthesis of Intermediate 7

Intermediate 7 was synthesized with a yield of 65% in the same manner as Intermediate 6, except that Intermediate 1 was used instead of N-phenyl-2-naphthylamine. This compound was identified using HR-MS. $C_{36}H_{26}BrN$ calc.: 551.1249; and found: 551.1246.

Synthesis Example 8

Synthesis of Intermediate 8

Intermediate 8 was synthesized with a yield of 68% in the same manner as Intermediate 6, except that Intermediate 2 was used instead of N-phenyl-2-naphthylamine. This compound was identified using HR-MS. $C_{39}H_{30}BrN$ calc.: 591.1562; and found: 591.1559.

Synthesis Example 9

Synthesis of Intermediate 9

3.66 g (30 mmol) of phenyl boronic acid, 38.4 g (60 mmol) of Intermediate 4, 1.7 g (1.5 mmol) of $Pd(PPh_3)_4$, and 20 g (150 mmol) of $K_2CO_3$ was dissolved in 100 ml of a mixed solution $THF/H_2O$ (2:1), and stirred at 80° C. for 5 hours. The reaction solution was extracted three times with 600 ml of diethylether. An organic layer was collected and dried using magnesium sulfate to evaporate the solvent. The residue was recrystallized with dichloromethane and normal hexane to obtain 13.04 g (yield: 65%) of Intermediate 9. This compound was identified using HR-MS. $C_{45}H_{34}BrN$ calc.: 667.1875; and found: 667.1873.

Synthesis Example 10

Synthesis of Intermediate 10

Intermediate 10 was synthesized with a yield of 58% in the same manner as Intermediate 9, except that Intermediate 5 was used instead of Intermediate 4. This compound was identified using HR-MS. $C_{36}H_{24}BrN$ calc.: 549.1092; and found: 549.1089.

Synthesis Example 11

Synthesis of Intermediate 11

Intermediate 11 was synthesized with a yield of 62% in the same manner as Intermediate 6, except that Intermediate 3 was used instead of N-phenyl-2-naphthylamine. $C_{42}H_{34}BrN$ calc.: 631.1875; and found: 631.1872.

Synthesis Example 12

Synthesis of Intermediate 12

Intermediate 12 was synthesized with a yield of 45% in the same manner as Intermediate 9, except that tris(4-bromophenyl) was used instead of Intermediate 4. This compound was identified using HR-MS. $C_{36}H_{24}Br_3N$ calc.: 706.9459; and found: 706.9455.

Intermediate 6
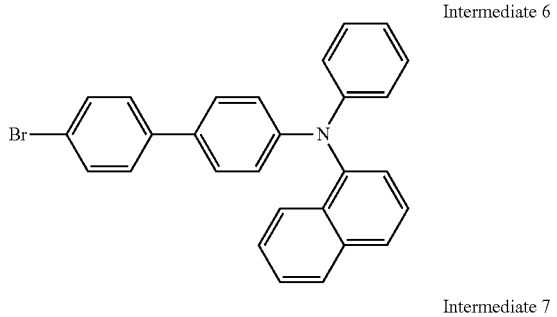

Intermediate 10
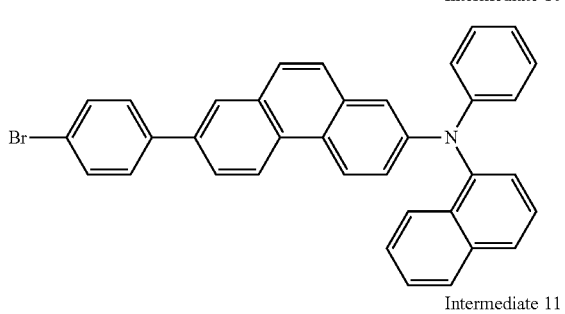

Intermediate 7
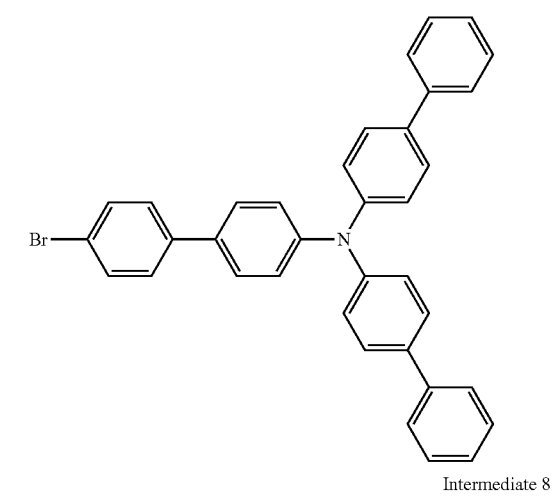

Intermediate 11
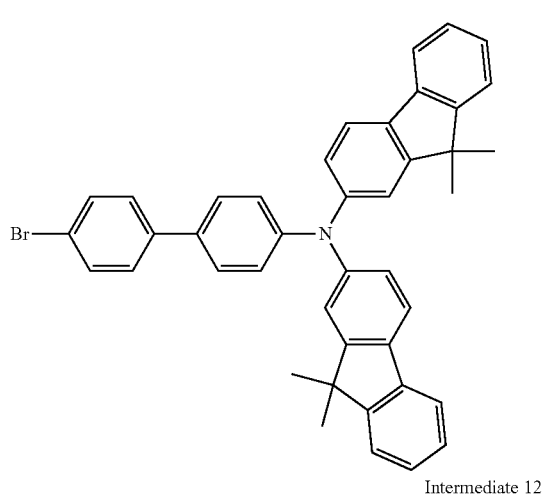

Intermediate 8
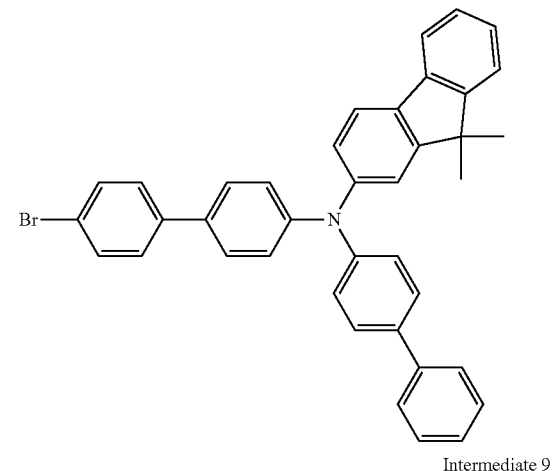

Intermediate 12
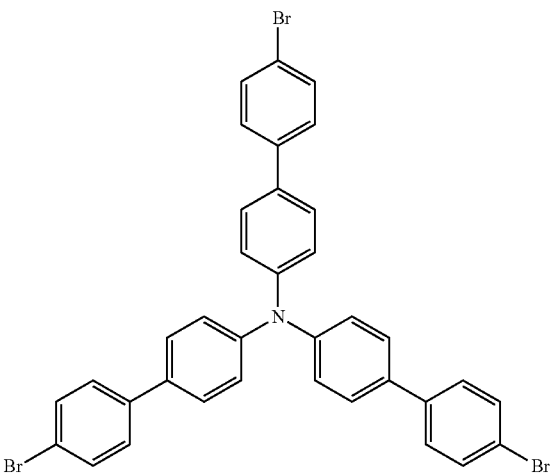

Intermediate 9
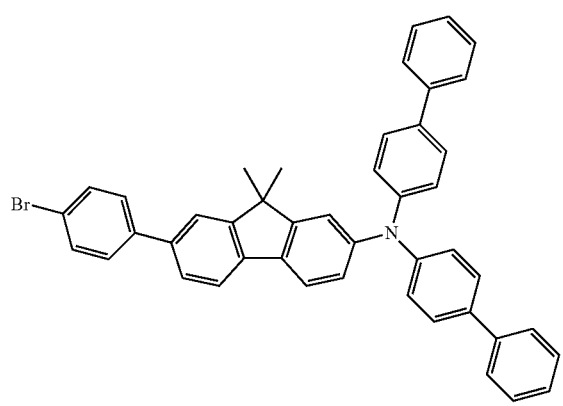

Synthesis Example 13

Synthesis of Intermediate 13

13.5 g (30 mmol) of Intermediate 6, 7.1 g (36 mmol) of benzophenone hydrazone, 4.3 g (45 mmol) of t-BuONa, 0.13 g (0.6 mmol) of Pd(OAc)$_2$, and 0.29 g (0.6 mmol) of 2-dicyclohexylphosphino-2',4',6'-triisopropylbiphenyl were dissolved in 60 mL of toluene and stirred at 90° C. for 3 hours. The reaction product was cooled to room temperature. Distilled water was added thereto and the product was extracted twice with 100 mL of diethylether and once with 100 mL of dichloromethane. An organic layer was collected and dried using magnesium sulfate, followed by filtration. The solvent was evaporated, and the residue was separated and purified using silica gel column chromatography to obtain 15.6 g (yield: 92%) of Intermediate 13. This compound was identified using HR-MS. $C_{41}H_{31}N_3$ calc.: 565.2518; and found: 565.2522.

Synthesis Example 14

Synthesis of Intermediate 14

Intermediate 14 was synthesized with a yield of 88% in the same manner as Intermediate 13, except that Intermediate 7 was used instead of Intermediate 6. This compound was identified using HR-MS. $C_{49}H_{37}N_3$ calc.: 667.2987; and found: 667.2990.

Synthesis Example 15

Synthesis of Intermediate 15

Intermediate 15 was synthesized with a yield of 84% in the same manner as Intermediate 13, except that Intermediate 8 was used instead of Intermediate 6. This compound was identified using HR-MS. $C_{52}H_{41}N_3$ calc.: 707.3300; and found: 707.3305.

Synthesis Example 16

Synthesis of Intermediate 16

Intermediate 16 was synthesized with a yield of 90% in the same manner as Intermediate 13, except that Intermediate 9 was used instead of Intermediate 6. This compound was identified using HR-MS. $C_{58}H_{45}N_3$ calc.: 783.3613; and found: 783.3615.

Synthesis Example 17

Synthesis of Intermediate 17

Intermediate 17 was synthesized with a yield of 85% in the same manner as Intermediate 13, except that Intermediate 10 was used instead of Intermediate 6. This compound was identified using HR-MS. $C_{49}H_{35}N_3$ calc.: 665.2831; and found: 665.2834.

Synthesis Example 18

Synthesis of Intermediate 18

Intermediate 18 was synthesized with a yield of 88% in the same manner as Intermediate 13, except that Intermediate 11 was used instead of Intermediate 6. This compound was identified using HR-MS. $C_{55}H_{45}N_3$ calc.: 747.3613; and found: 747.3616.

Synthesis Example 19

Synthesis of Intermediate 19

Intermediate 19 was synthesized with a yield of 76% in the same manner as that of Intermediate 13, except that Intermediate 12 was used instead of Intermediate 6. This compound was identified using HR-MS. $C_{75}H_{57}N_7$ calc.: 1055.4675; and found: 1055.4677.

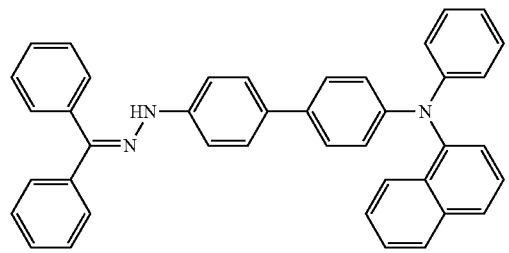

Intermediate 13

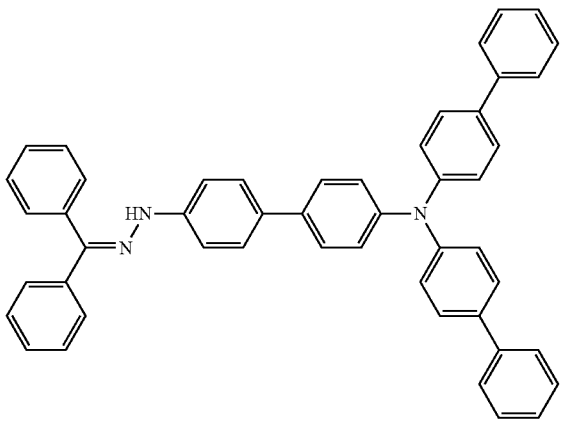

Intermediate 14

Intermediate 15
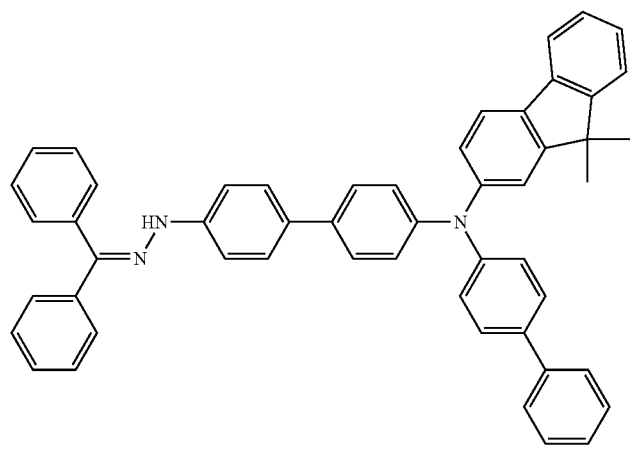
Intermediate 16
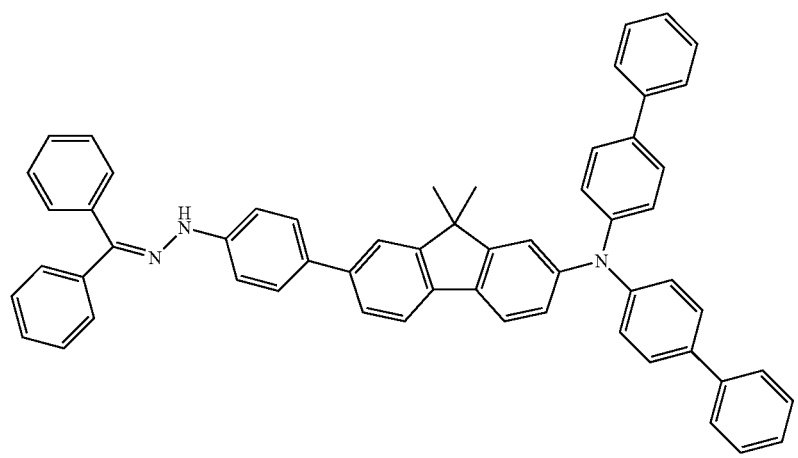
Intermediate 17
Intermediate 18
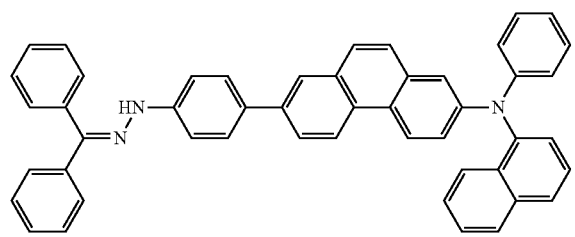
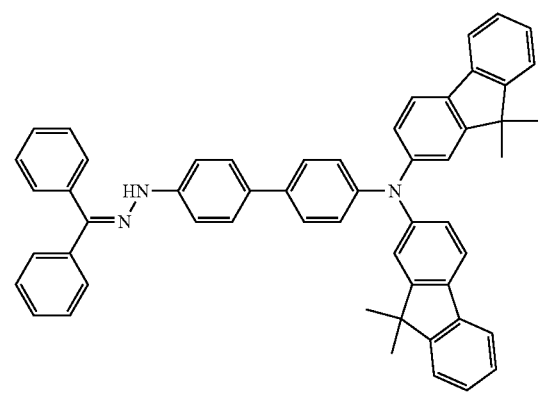

Intermediate 19

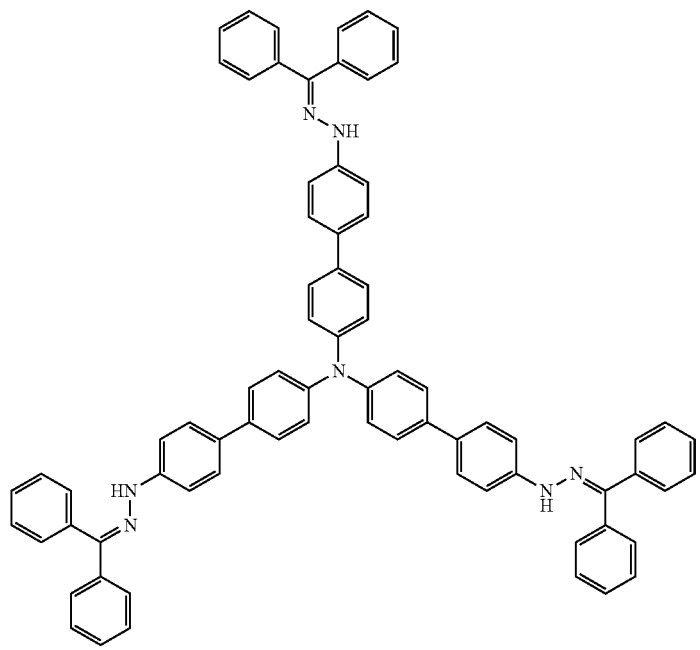

Synthesis Example 20

Synthesis of Intermediate 20

11.3 g (20 mmol) of Intermediate 13, 7.6 g (40 mmol) of p-toluenesulfonic acid monohydrate, 15.70 g (80 mmol) of benzylphenylketone were dissolved in 80 mL of ethanol and 80 mL of toluene and stirred at 110° C. for 24 hours. The reaction product was cooled to room temperature. Distilled water was added thereto and extracted twice with 100 mL of diethylether and twice with 100 mL of dichloromethane. An organic layer was collected and dried using magnesium sulfate, followed by filtration. The solvent was evaporated, and the residue was separated and purified using silica gel column chromatography to obtain 7.9 g (yield: 70%) of Intermediate 20. This compound was identified using HR-MS. $C_{42}H_{30}N_2$ calc.: 562.2409; and found: 562.2412.

Synthesis Example 21

Synthesis of Intermediate 21

Intermediate 21 was synthesized with a yield of 68% in the same manner as Intermediate 20, except that Intermediate 14 was used instead of Intermediate 13. This compound was identified using HR-MS. $C_{50}H_{36}N_2$ calc.: 664.2878; and found: 664.2881.

Synthesis Example 22

Synthesis of Intermediate 22

Intermediate 22 was synthesized with a yield of 76% in the same manner as Intermediate 20, except that Intermediate 15 was used instead of Intermediate 13. This compound was identified using HR-MS. $C_{53}H_{40}N_2$ calc.: 704.3191; and found: 704.3193.

Synthesis Example 23

Synthesis of Intermediate 23

Intermediate 23 was synthesized with a yield of 73% in the same manner as Intermediate 20, except that Intermediate 16 was used instead of Intermediate 13. This compound was identified using HR-MS. $C_{59}H_{44}N_2$ calc.: 780.3504; and found: 780.3508.

Synthesis Example 24

Synthesis of Intermediate 24

Intermediate 24 was synthesized with a yield of 65% in the same manner as Intermediate 20, except that Intermediate 17 was used instead of Intermediate 13. This compound was identified using HR-MS. $C_{50}H_{34}N_2$ calc.: 662.2722; and found: 662.2726.

Synthesis Example 25

Synthesis of Intermediate 25

Intermediate 25 was synthesized with a yield of 58% in the same manner as that of Intermediate 20, except that Intermediate 18 was used instead of Intermediate 13. This compound was identified using HR-MS. $C_{56}H_{44}N_2$ calc.: 744.3504; and found: 744.3504.

Synthesis Example 26

Synthesis of Intermediate 26

Intermediate 26 was synthesized with a yield of 48% in the same manner as that of Intermediate 20, except that Intermediate 19 was used instead of Intermediate 13. This compound was identified using HR-MS. $C_{78}H_{54}N_4$ calc.: 1046.4348; and found: 1046.4352.

Intermediate 20
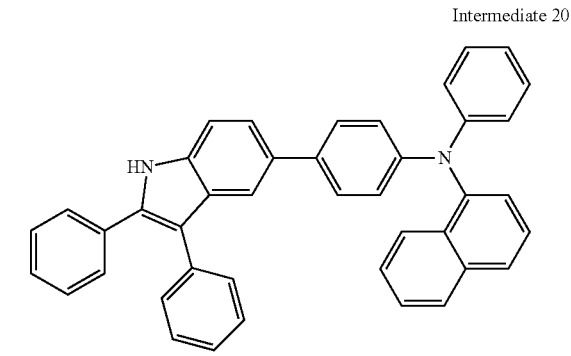
Intermediate 21
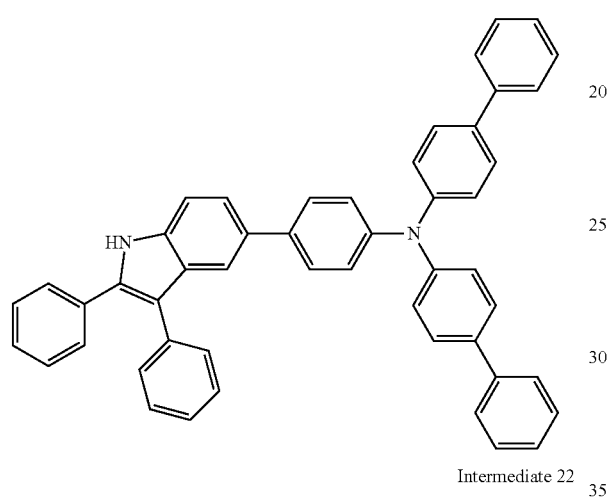
Intermediate 22
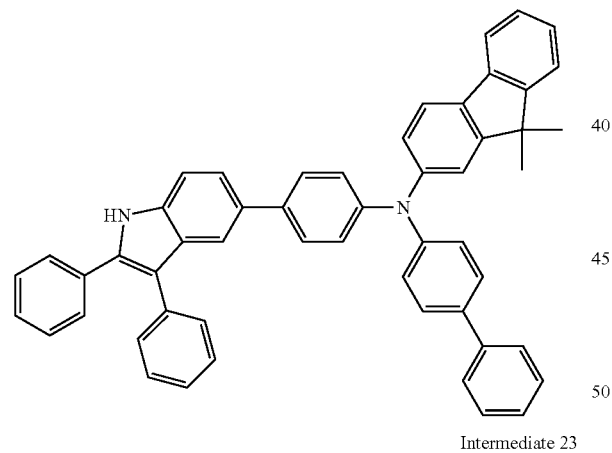
Intermediate 23
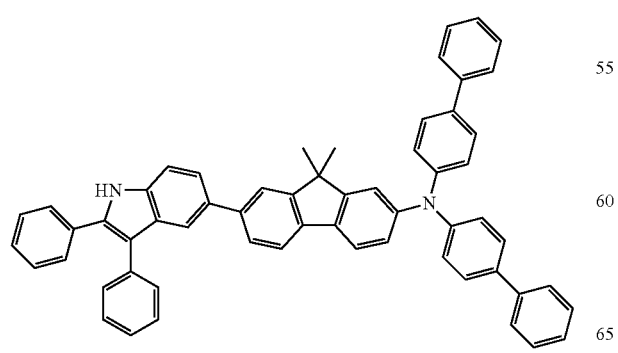
Intermediate 24
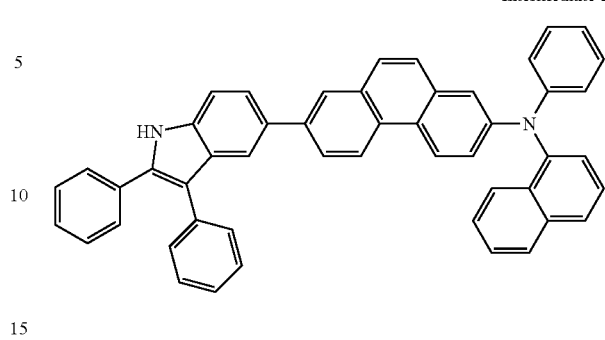
Intermediate 25
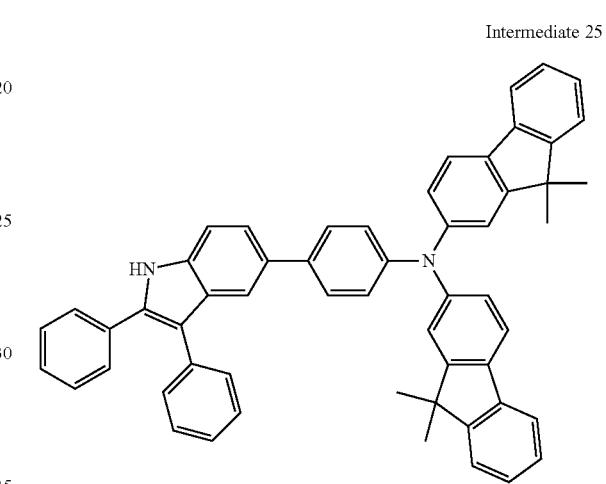
Intermediate 26
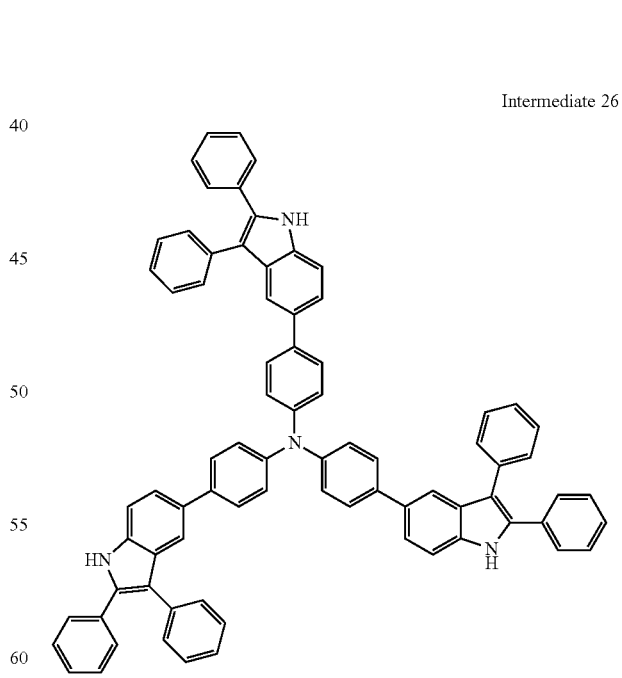

Synthesis Example 27

Synthesis of Compound 1

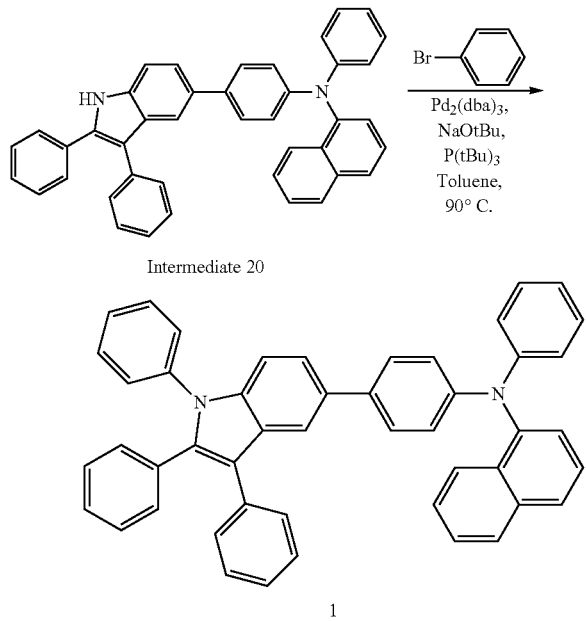

Figure 2:
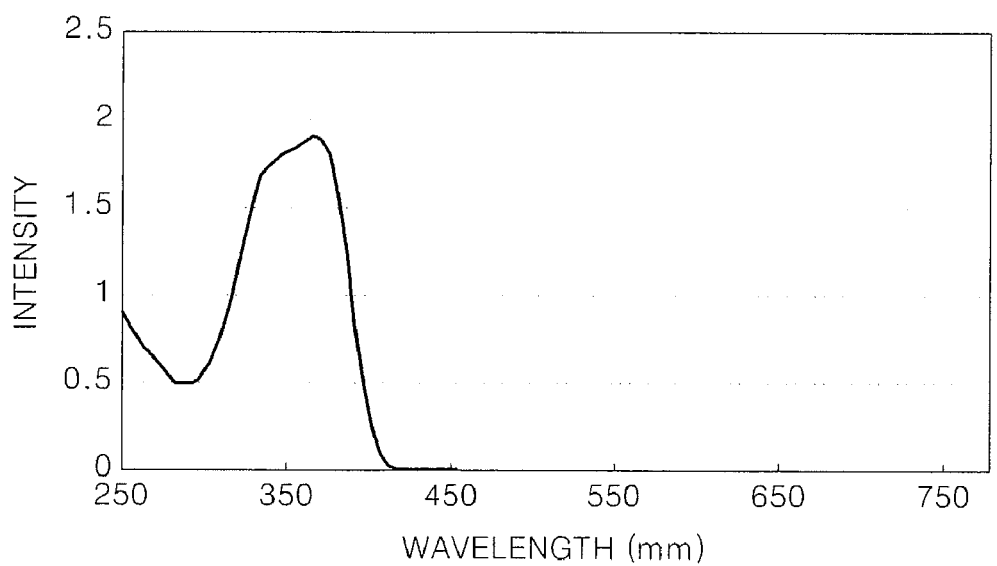
FIG. 2 is a graph of the absorption spectra of Compound 1 prepared according to Synthesis Example 27.
Figure 3:
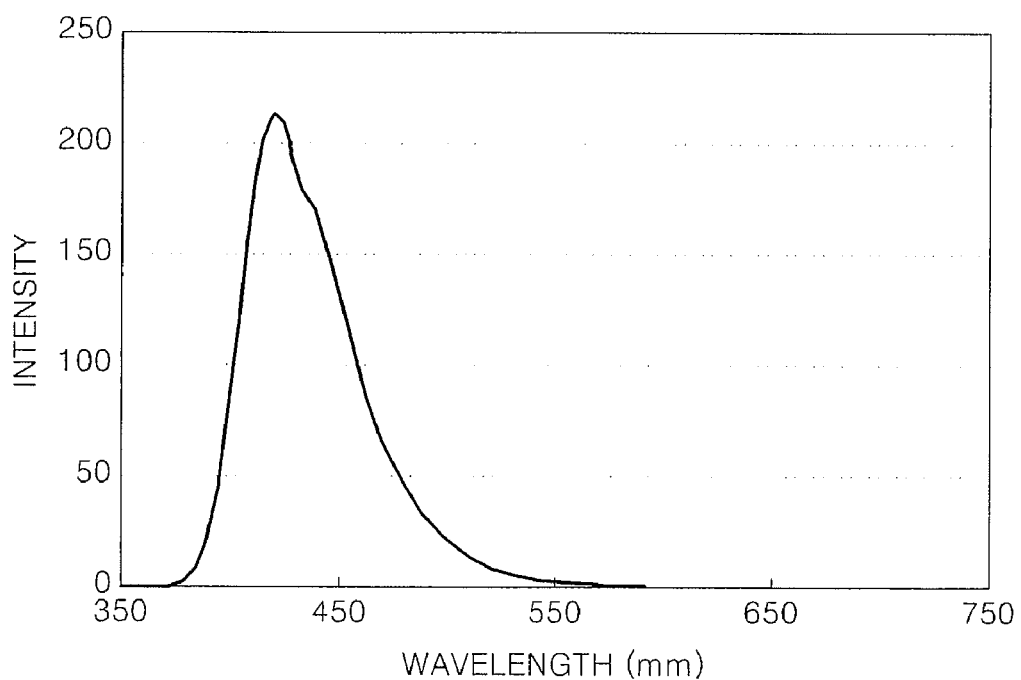
FIG. 3 is a graph of the emission spectra of Compound 1 prepared according to Synthesis Example 27.

5.63 g (10 mmol) of Intermediate 20, 1.88 g (12 mmol) of bromobenzene, 2.9 g (30 mmol) of t-BuONa, 366 mg (0.4 mmol) of $Pd_2(dba)_3$, and 80 mg (0.4 mmol) of $P(t-Bu)_3$ were dissolved in 60 ml of toluene and stirred at 90° C. for 3 hours. After the reaction was completed, the reaction product was cooled to room temperature and extracted three times with distilled water and 50 ml of diethylether. An organic layer was collected and dried using magnesium sulfate to evaporate the solvent. The residue was separated and purified using silica gel column chromatography to obtain 4.6 g (yield: 72%) of Compound 1. FIGS. 2 and 3 are graphs showing the absorption and emission spectra of Compound 1, respectively. $C_{48}H_{34}N_2$ calc.: 638.2722; found: 638.2721; $^1$H NMR (CDCl$_3$, 400 MHz) δ (ppm) 8.69 (d, 1H), 8.49 (dd, 1H), 7.85 (dd, 1H), 7.70-7.45 (m, 22H), 7.27 (dd, 2H), 7.12 (dt, 1H), 7.02 (d, 2H), 6.97 (dd, 1H), 6.83 (d, 2H).

Synthesis Example 28

Synthesis of Compound 2

Compound 2 was synthesized with a yield of 67% in the same manner as Compound 1, except that Intermediate 21 was used instead of Intermediate 20. This compound was identified using HR-MS. $C_{56}H_{40}N_2$ calc.: 740.3191; found: 740.3193; $^1$H NMR (CDCl$_3$, 400 MHz) δ (ppm) 8.68 (d, 1H), 7.77-7.74 (m, 3H), 7.67-7.65 (m, 4H), 7.62-7.35 (m, 26H), 7.12 (dd, 2H), 6.87 (dd, 4H).

Synthesis Example 29

Synthesis of Compound 8

Compound 8 was synthesized with a yield of 69% in the same manner as Compound 2, except that 1-bromonaphthalene was used instead of bromobenzene. $C_{60}H_{42}N_2$ calc.: 790.3348; found: 790.3350; $^1$H NMR (CDCl$_3$, 400 MHz) δ (ppm) 8.67 (d, 1H), 8.44 (dd, 1H), 7.76-7.73 (m, 2H), 7.70-7.64 (m, 4H), 7.55 (t, 2H), 7.50-7.32 (m, 28H), 6.94-6.89 (m, 4H).

Synthesis Example 30

Synthesis of Compound 29

Compound 29 was synthesized with a yield of 75% in the same manner as Compound 1, except that Intermediate 22 was used instead of Intermediate 20. This compound was identified using HR-MS. $C_{65}H_{48}N_2$ calc.: 856.3817; found: 856.3819; $^1$H NMR (CDCl$_3$, 400 MHz) δ (ppm) 8.69 (d, 1H), 7.98 (d, 1H), 7.85 (d, 2H), 7.70-7.65 (m, 4H), 7.63-7.53 (m, 4H), 7.47-7.20 (m, 22H), 7.05 (t, 1H), 6.93 (d, 2H), 6.87 (dd, 4H), 6.79 (dd, 1H), 1.96 (s, 6H).

Synthesis Example 31

Synthesis of Compound 32

Compound 32 was synthesized with a yield of 63% in the same manner as Compound 1, except that Intermediate 23 was used instead of Intermediate 20. This compound was identified using HR-MS. $C_{65}H_{48}N_2$ calc.: 856.3817; found: 856.3820; $^1$H NMR (CDCl$_3$, 400 MHz) δ (ppm) 8.65 (d, 1H), 7.85 (dd, 4H), 7.76 (dd, 4H), 7.63-7.36 (m, 20H), 7.23-7.13 (m, 6H), 7.10 (t, 1H), 6.98 (dd, 1H), 6.76 (d, 4H), 6.73 (dd, 1H), 1.94 (s, 6H).

Synthesis Example 32

Synthesis of Compound 52

Compound 52 was synthesized with a yield of 60% in the same manner as Compound 1, except that Intermediate 24 was used instead of Intermediate 20. This compound was identified using HR-MS. $C_{56}H_{38}N_2$ calc.: 738.3035; found: 738.3037; $^1$H NMR (CDCl$_3$, 400 MHz) δ (ppm) 8.66 (d, 1H), 8.63 (d, 1H), 8.55 (d, 1H), 8.53 (dd, 1H), 8.42 (d, 1H), 7.96 (s, 1H), 7.92 (dd, 1H), 7.89 (d, 1H), 7.71 (t, 1H), 7.65-7.35 (m, 19H), 7.23-7.12 (m, 6H), 6.99 (dt, 1H), 6.87 (d, 1H), 6.80 (d, 2H).

Synthesis Example 33

Synthesis of Compound 58

Compound 58 was synthesized with a yield of 68% in the same manner as Compound 1, except that Intermediate 25 was used instead of Intermediate 20. This compound was identified using HR-MS. $C_{62}H_{48}N_2$ calc.: 820.3817; found: 820.3818; $^1$H NMR (CDCl$_3$, 400 MHz) δ (ppm) 8.69 (d, 1H), 8.01 (d, 2H), 7.96 (dd, 4H), 7.80-7.32 (m, 19H), 7.23 (d, 2H), 7.19 (dd, 2H), 7.05 (dt, 2H), 6.89 (d, 2H), 6.80 (dd, 2H), 1.95 (s, 12H).

Synthesis Example 34

Synthesis of Compound 81

Compound 81 was synthesized with a yield of 53% in the same manner as Compound 1, except that Intermediate 26 was used instead of Intermediate 20. This compound was identified using HR-MS. $C_{96}H_{66}N_4$ calc.: 1274.5287; found:

1274.5292; ¹H NMR (CDCl₃, 400 MHz) δ (ppm) 8.65 (d, 3H), 7.83 (dd, 6H), 7.69-7.23 (m, 45H), 7.21 (dd, 6H), 6.83 (dd, 6H).

Example 1

An anode was prepared by cutting a Corning 15 Ωcm² (1200 Å) ITO glass substrate to a size of 50 mm×50 mm×0.7 mm, ultrasonically cleaning the glass substrate using isopropyl alcohol and pure water for 5 minutes each, and then irradiating with UV light for 30 minutes and exposing to ozone to clean. Then, the anode was mounted in a vacuum deposition apparatus.

2-TNATA was vacuum-deposited on the anode to a thickness of 600 Å to form an HIL, and Compound 1 as a hole transporting compound was vacuum-deposited on the HIL to a thickness of 300 Å to form a HTL.

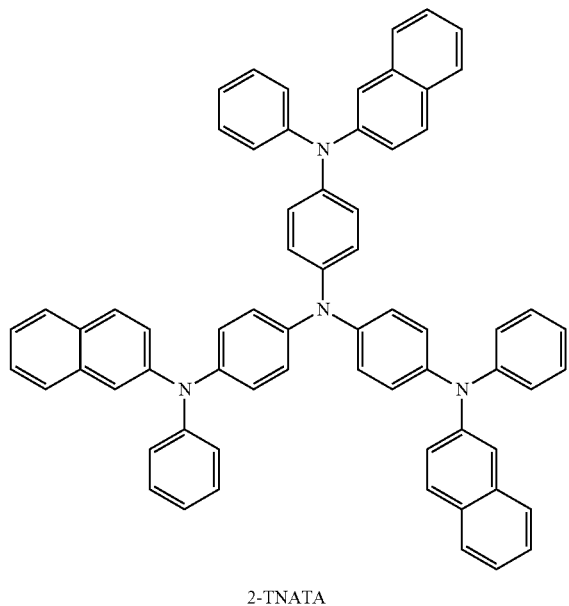

2-TNATA

Then, a green fluorescent host (Alq₃) and a green fluorescent dopant (C545T) were co-deposited at a weight ratio of 98:2 on the HTL to form an EML with a thickness of 300 Å.

Next, Alq₃ was deposited on the EML to a thickness of 300 Å to form an ETL, and LiF was deposited to a thickness of 10 Å on the ETL to form an EIL. Finally, Al was vacuum-deposited on the EIL to a thickness of 3000 Å to form a LiF/Al electrode (cathode), thereby completing the manufacture of an organic light-emitting device.

Example 2

An organic light-emitting device was manufactured as in Example 1, except that Compound 2 was used instead of Compound 1 to form the HTL.

Example 3

An organic light-emitting device was manufactured as in Example 1, except that Compound 8 was used instead of Compound 1 to form the HTL.

Example 4

An organic light-emitting device was manufactured as in Example 1, except that Compound 29 was used instead of Compound 1 to form the HTL.

Example 5

An organic light-emitting device was manufactured as in Example 1, except that Compound 32 was used instead of Compound 1 to form the HTL.

Example 6

An organic light-emitting device was manufactured as in Example 1, except that Compound 52 was used instead of Compound 1 to form the HTL.

Example 7

An organic light-emitting device was manufactured as in Example 1, except that Compound 58 was used instead of Compound 1 to form the HTL.

Example 8

An organic light-emitting device was manufactured as in Example 1, except that Compound 81 was used instead of Compound 1 to form the HTL.

Comparative Example 1

An organic light-emitting device was manufactured in the same manner as in Example 1, except that 4,4'-bis[N-(1-naphthyl)-N-phenylamino]biphenyl (NPB) was used instead of Compound 1 to form the HTL.

The organic light-emitting device had a driving voltage of 7.45V at a current density of 50 mA/cm², a luminance of 6,102 cd/m², color coordinates of (0.309, 0.642), and a luminescent efficiency of 12.2 cd/A.

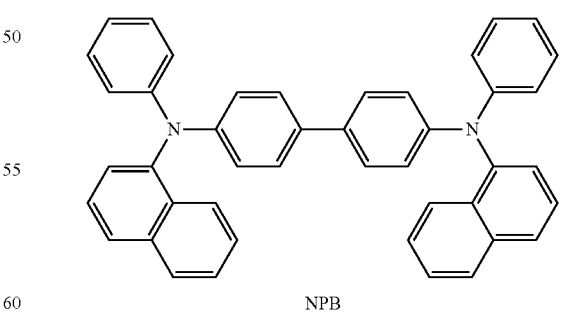

NPB

The driving voltage at a current density of 50 mA/cm², luminance, color coordinates, and luminescent efficiency of each of the organic light-emitting devices manufactured in Examples 1 through 6 and Comparative Example 1 were measured. The results are shown in Table 1 below.

TABLE 1

|  | HTL material | Driving voltage (V) | Luminance (cd/m$^2$) | Color coordinates | Luminescent efficiency |
|---|---|---|---|---|---|
| Example 1 | Compound 1 | 6.67 | 7834 | (0.310, 0.643) | 15.67 cd/A |
| Example 2 | Compound 2 | 6.5 | 8240 | (0.309.643) | 16.48 cdA |
| Example 3 | Compound 8 | 6.46 | 8154 | (0.310, 0.642) | 16.31 cd/A |
| Example 4 | Compound 29 | 6.37 | 8611 | (0.308, 0.642) | 17.22 cd/A |
| Example 5 | Compound 32 | 6.34 | 8196 | (0.310, 0.641) | 16.39 cd/A |
| Example 6 | Compound 52 | 6.78 | 7917 | (0.311, 0.644) | 15.83 cd/A |
| Example 7 | Compound 58 | 6.63 | 8203 | (0.309, 0.641) | 16.41 cd/A |
| Example 8 | Compound 81 | 6.82 | 7924 | (0.312, 0.643) | 15.85 cd/A |
| Comparative Example 1 | NPB | 7.45 | 6102 | (0.309, 0.642) | 12.2 cd/A |

Referring to Table 1, the organic light-emitting devices manufactured using the heteroarylamine compounds of Formula 1 according to embodiments of the present invention had driving voltages that were lower by 1 V or greater than the device in which NPB was used, and thus had higher efficiency and improved I-V-L characteristics. In particular, the lifetime characteristics were markedly improved by 100% or greater in the organic light-emitting devices according to Examples 1 through 8, as compared to the organic light-emitting device according to Comparative Example 1.

The half life-span at a current density of 100 mA/cm$^2$ of each of the organic light-emitting devices manufactured according to Examples 1 through 8 and Comparative Example 1 was measured. The results are shown in Table 2 below.

TABLE 2

| Examples | HTL material | Half life-span (hr @100 mA/cm$^2$) |
|---|---|---|
| Example 1 | Compound 1 | 514 hr |
| Example 2 | Compound 2 | 558 hr |
| Example 3 | Compound 8 | 480 hr |
| Example 4 | Compound 29 | 562 hr |
| Example 5 | Compound 32 | 614 hr |
| Example 6 | Compound 52 | 586 hr |
| Example 7 | Compound 58 | 453 hr |
| Example 8 | Compound 81 | 397 hr |
| Comparative Example 1 | NPB | 237 hr |

Referring to Table 2, the organic light-emitting devices according to Examples 1 through 8 had longer half life-spans than the organic light-emitting device according to Comparative Example 1.

The heteroarylamine compounds of Formula 1 have improved electrical characteristics and charge transporting capabilities, and thus may be used as at least one of a hole injecting material, a hole transporting material, and a material for emission layers. These materials are suitable for any color fluorescent and phosphorescent devices, such as red, green, blue, and white fluorescent and phosphorescent devices.

Organic light-emitting devices including organic layers containing the heteroarylamine compound of Formula 1 have high efficiency, low driving voltages, and high luminance.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heteroarylamine compound comprising a compound selected from the group consisting of compounds represented by Formulae 2 through 6 below:

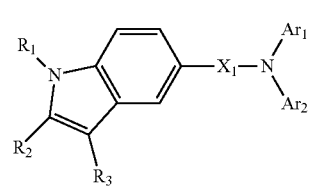

Formula 2

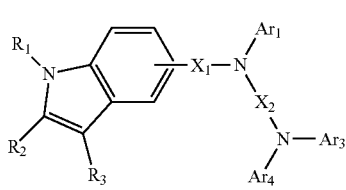

Formula 3

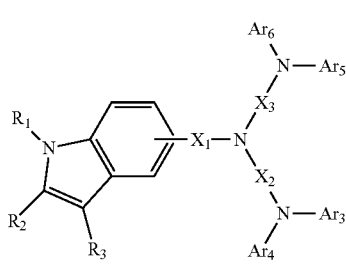

Formula 4

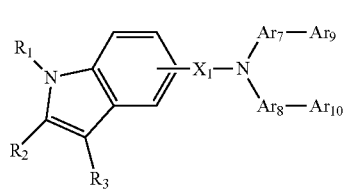

Formula 5

-continued

Formula 6

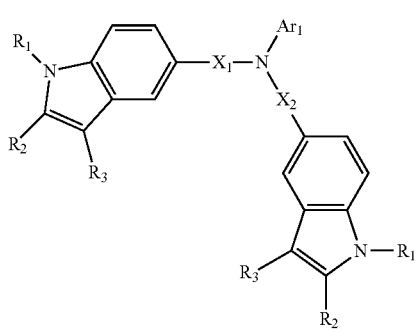

wherein:
each of $Ar_1$ through $Ar_{10}$ is independently selected from the group consisting of substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups;
each of $X_1$ through $X_3$ is independently selected from the group consisting of substituted and unsubstituted $C_6$-$C_{30}$ arylene groups, substituted and unsubstituted $C_4$-$C_{30}$ heteroarylene groups, and substituted and unsubstituted $C_6$-$C_{30}$ condensed polycyclic groups; and
each of $R_1$, $R_2$ and $R_3$ is independently selected from the group consisting of phenyl groups, 4-fluorophenyl groups, naphthalene groups, and biphenyl groups.

2. The heteroarylamine compound of claim 1, wherein each of $X_1$ through $X_3$ is independently selected from the group consisting of phenylene groups, biphenylene groups, terphenylene groups, quaterphenylene groups, naphthylene groups, anthracenylene groups, phenanthrylene groups, chrysenylene groups, pyrenylene groups, perylenylene groups, fluorenylene groups, thiophenylene groups, 1-phenylthiophenylene groups, 1,4-diphenylthiophenylene groups, benzothiophenylene groups, 1-phenylbenzothiophenylene groups, 1,8-diphenylbenzothiophenylene groups, furylene groups, 1-phenyldibenzothiophenylene groups, 1,8-diphenylthiophenylene groups, dibenzofuranylene groups, 1-phenyldibenzofuranylene groups, 1,8-diphenyldibenzofuranylene groups, and benzothiazolylene groups.

3. The heteroarylamine compound of claim 1, wherein each of $Ar_1$ through $Ar_{10}$ is selected from the group consisting of:
monocyclic to tricyclic aryl groups selected from the group consisting of phenyl groups, naphthyl groups, biphenyl groups, terphenyl groups, fluorenyl groups, and carbazolyl groups, and
monocyclic to tricyclic aryl groups substituted with one to three substituents selected from the group consisting of $C_1$-$C_5$ alkyl groups, $C_1$-$C_5$ alkoxy groups, cyano groups, amino groups, phenoxy groups, phenyl groups, and halogen atoms.

4. The heteroarylamine compound of claim 1, wherein each of $X_1$ through $X_3$ is independently selected from the group consisting of:

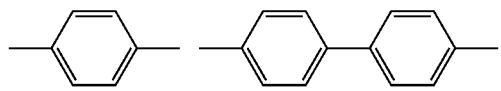

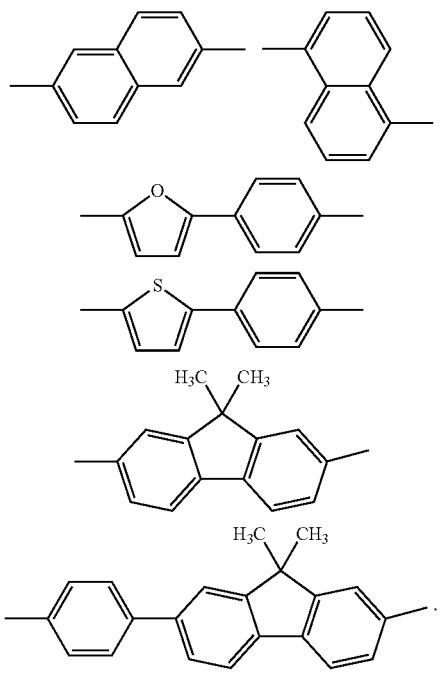

5. The heteroarylamine compound of claim 1, wherein each of $Ar_1$ through $Ar_{10}$ is independently selected from the group consisting of:

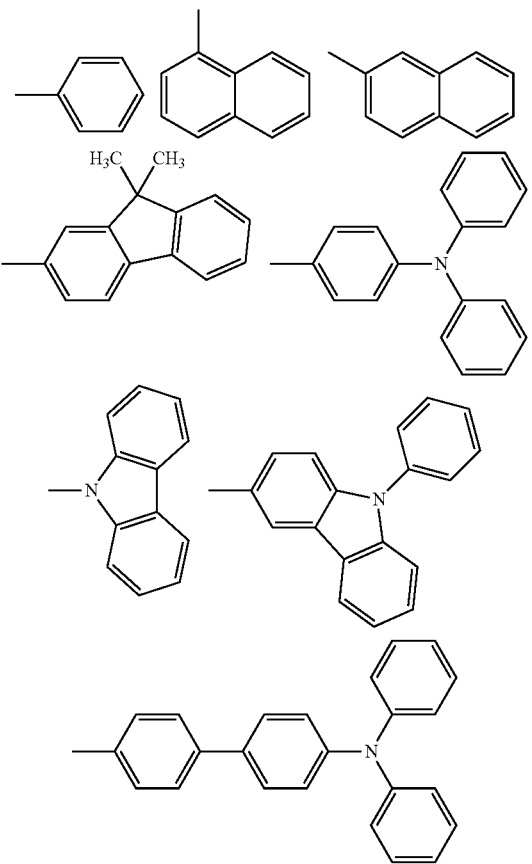

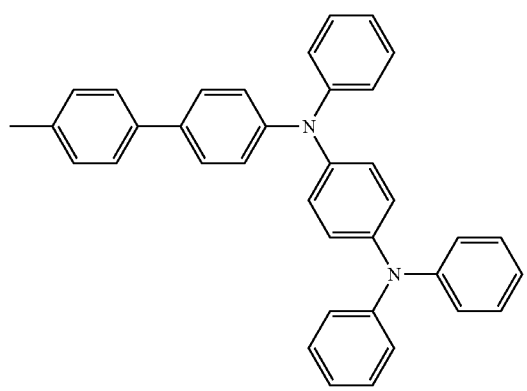
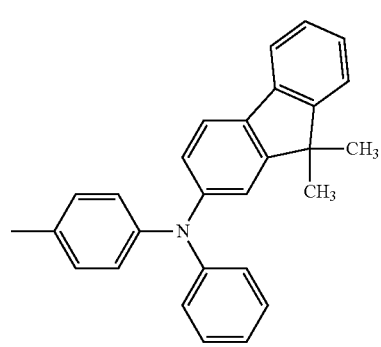
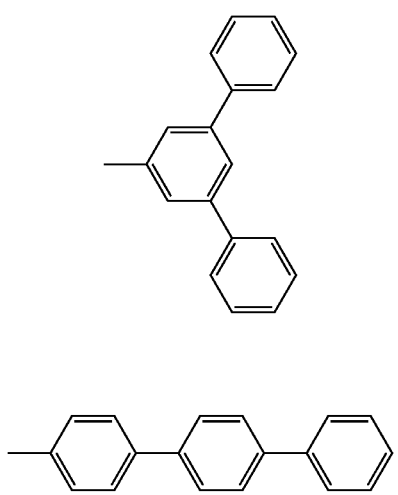
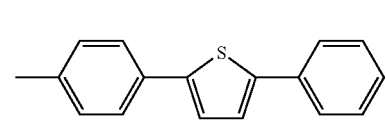
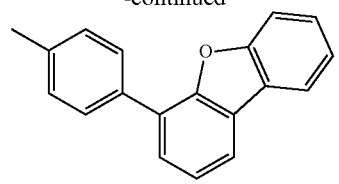
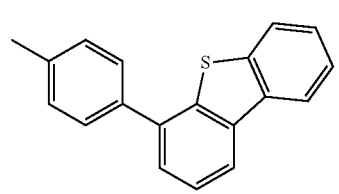
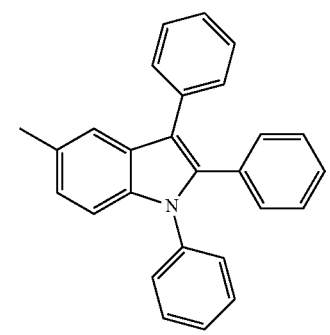
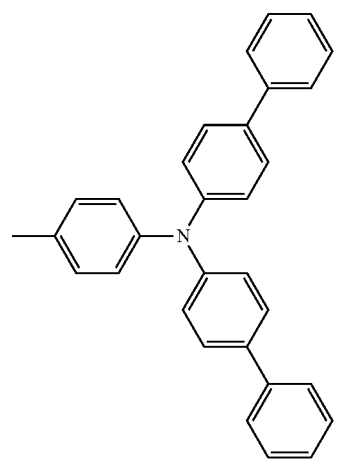
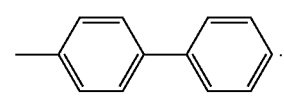
6. The heteroarylamine compound of claim 1, wherein the compound represented by one of Formulae 2 through 6 comprises a compound selected from the group consisting of Compounds 1, 2, 8, 29, 32, 52, 58 and 81:

1
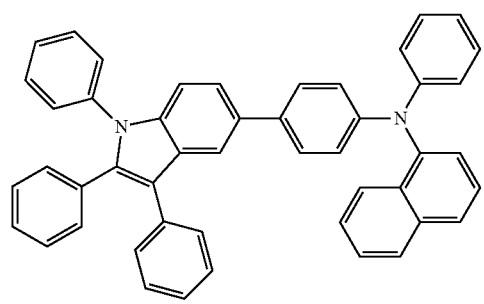
2
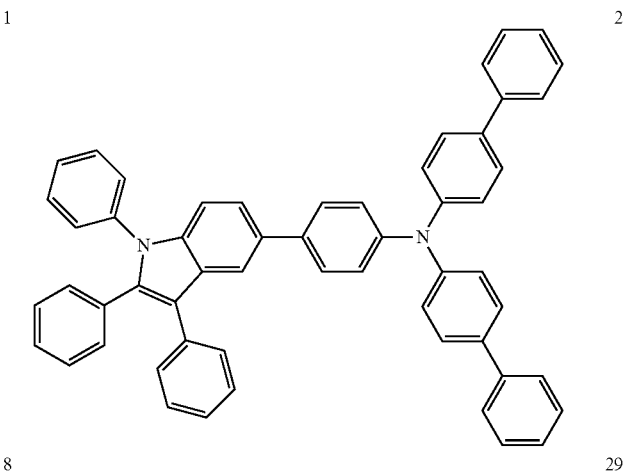
8
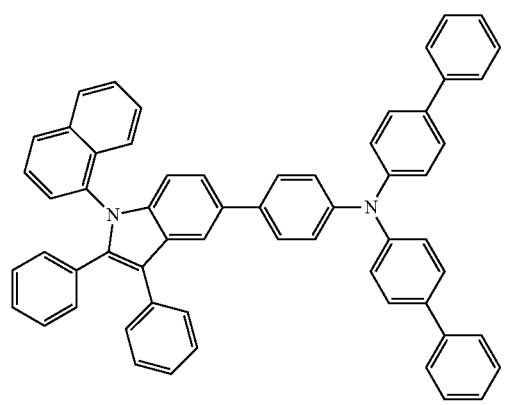
29
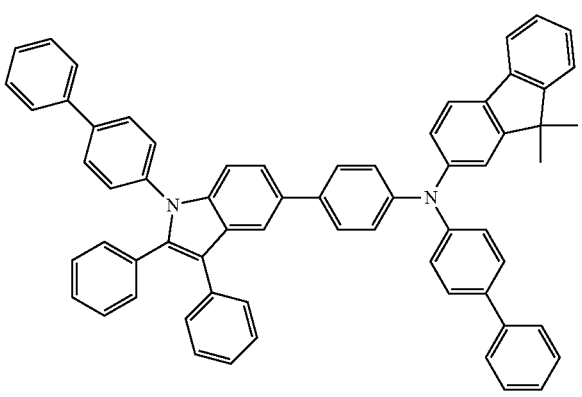
32
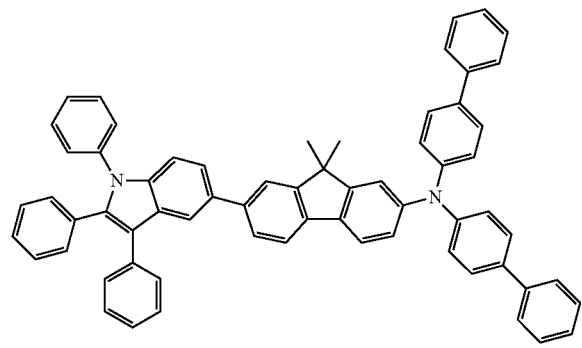
52
58
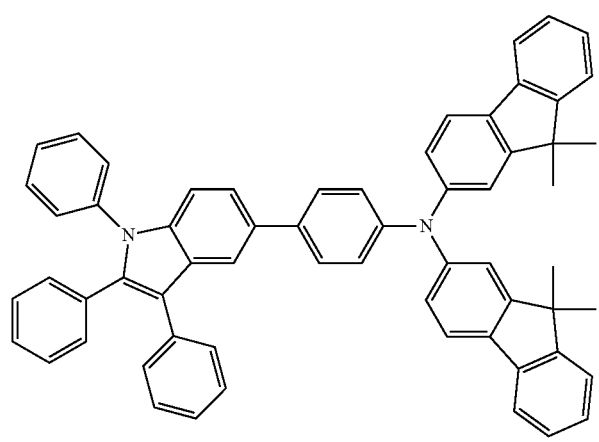

-continued

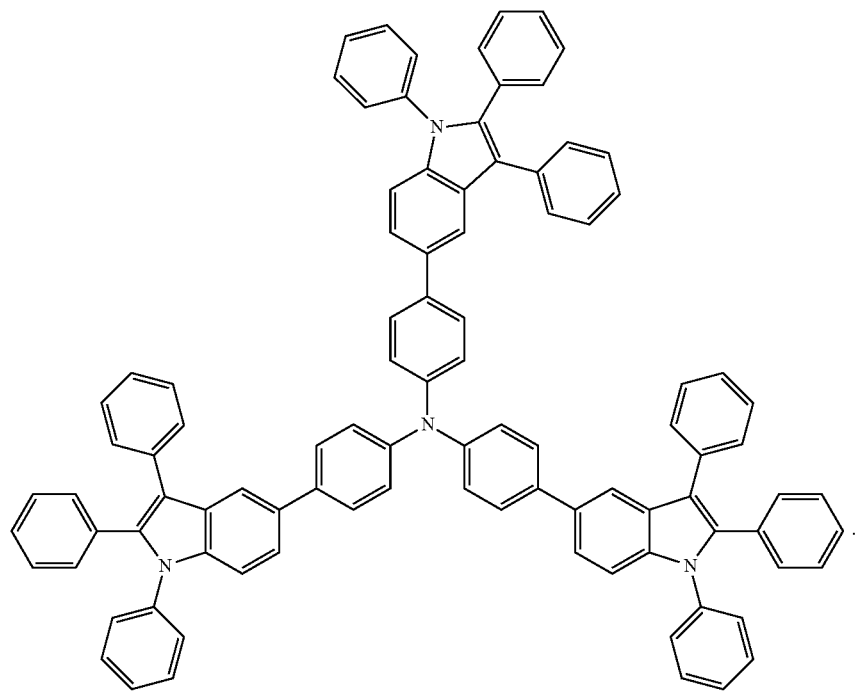

7. An organic light-emitting device comprising a first electrode, a second electrode, and an organic layer between the first electrode and the second electrode, wherein the organic layer comprises at least one organic layer comprising the heteroarylamine compound of claim 1.

8. The organic light-emitting device of claim 7, wherein the organic layer comprises a hole injection layer or a hole transport layer.

9. The organic light-emitting device of claim 7, wherein the organic layer comprises an emission layer or a single layer having hole injecting capability and hole transporting capability.

10. The organic light-emitting device of claim 7, wherein the organic layer comprises an emission layer, and the emission layer comprises the heteroarylamine compound of one of Formulae 2 through 6 as a host for a fluorescent or phosphorescent organic light-emitting device.

11. The organic light-emitting device of claim 7, wherein the organic layer comprises a hole injection layer, a hole transport layer, and an emission layer, wherein the hole injection layer or the hole transport layer comprises the heteroarylamine compound of one of Formulae 2 through 6, and the emission layer comprises an anthracene compound or an arylamine compound or a heteroarylamine compound or a styryl compound.

12. The organic light-emitting device of claim 7, wherein the organic layer comprises a hole injection layer, a hole transport layer, and an emission layer, wherein the hole injection layer or the hole transport layer comprises the heteroarylamine compound of one of Formula 2 through 6, and the emission layer comprises a red emission layer, a green emission layer, a blue emission layer, and a white emission layer, wherein at least one of the red emission layer, green emission layer, the blue emission layer and the white emission layer comprises a phosphorescent compound.

13. The organic light-emitting device of claim 7, wherein the organic layer comprises at least one layer selected from the group consisting of a hole injection layer, a hole transport layer, an electron blocking layer, an emission layer, a hole blocking layer, an electron transport layer, and an electron injection layer.

14. The organic light-emitting device of claim 13, wherein the organic light-emitting device comprises a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure.

15. A flat panel display device comprising the organic light-emitting device according to claim 7, wherein the first electrode of the organic light-emitting device is electrically connected to a source electrode or a drain electrode of a thin film transistor.

16. An organic light-emitting device comprising a first electrode, a second electrode, and an organic layer between the first electrode and the second electrode, wherein the organic layer comprises at least one layer comprising the heteroarylamine compound of claim 1, the at least one layer being foamed using a wet process.

* * * * *

UNITED STATES PATENT AND TRADEMARK OFFICE
CERTIFICATE OF CORRECTION

| | | |
|---|---|---|
| PATENT NO. | : 8,283,057 B2 | Page 1 of 1 |
| APPLICATION NO. | : 12/830646 | |
| DATED | : October 9, 2012 | |
| INVENTOR(S) | : Young-Kook Kim et al. | |

It is certified that error appears in the above-identified patent and that said Letters Patent is hereby corrected as shown below:

In the Claims

Column 90, Claim 16, line 59          Delete "foamed"
                                      Insert -- formed --

Signed and Sealed this
Fifteenth Day of July, 2014

Michelle K. Lee
*Deputy Director of the United States Patent and Trademark Office*